US012774353B2

(12) United States Patent
Gin et al.

(10) Patent No.: US 12,774,353 B2
(45) Date of Patent: Oct. 27, 2026

(54) LYOTROPIC GYROID MESOPHASE COMPOSITIONS, POLYMER COMPOSITIONS COMPRISING THE SAME, METHODS OF PREPARATION THEREOF, AND METHODS OF USING THE SAME

(71) Applicants: The Regents of the University of Colorado, a body corporate, Denver, CO (US); The Trustees Of The University Of Pennsylvania, Philadelphia, PA (US)

(72) Inventors: Douglas L. Gin, Longmont, CO (US); Patrick Li, Broomfield, CO (US); Chinedum Osuji, Gladwyne, PA (US); Omar Imran, Philadelphia, PA (US); Christopher Johnson, Philadelphia, PA (US); Samantha S. Dyer, Boulder, CO (US)

(73) Assignees: The Regents of the University of Colorado, a body corporate, Denver, CO (US); The Trustees Of The University Of Pennsylvania, Philadelphia, PA (US)

( * ) Notice: Subject to any disclaimer, the term of this patent is extended or adjusted under 35 U.S.C. 154(b) by 916 days.

(21) Appl. No.: 17/949,072

(22) Filed: Sep. 20, 2022

(65) Prior Publication Data

US 2023/0103984 A1 Apr. 6, 2023

Related U.S. Application Data

(60) Provisional application No. 63/246,143, filed on Sep. 20, 2021.

(51) Int. Cl.
*C08F 36/22* (2006.01)
*C07C 233/38* (2006.01)

(52) U.S. Cl.
CPC ............ *C08F 36/22* (2013.01); *C07C 233/38* (2013.01)

(58) Field of Classification Search
None
See application file for complete search history.

(56) References Cited

U.S. PATENT DOCUMENTS

| | | | | |
|---|---|---|---|---|
| 3,689,468 A * | 9/1972 | Cenci et al. | G03G 5/107 526/923 |
| 5,252,103 A * | 10/1993 | Kamata | D06P 1/66 8/606 |
| 11,261,276 B2 * | 3/2022 | Mukunoki | C08F 220/40 |
| 2009/0252875 A1 * | 10/2009 | Ishiji | C09D 17/002 427/256 |
| 2024/0058767 A1 * | 2/2024 | Osuji | B01D 61/08 |

FOREIGN PATENT DOCUMENTS

| | | | |
|---|---|---|---|
| EP | 06212579 A * | 8/1984 | |
| EP | 2339401 A1 * | 6/2011 | B41C 1/1008 |
| GB | 785992 A * | 11/1957 | |
| JP | 2019181345 A * | 10/2019 | |
| JP | 2020090636 A * | 6/2020 | |
| JP | 2025067291 A * | 4/2025 | |

OTHER PUBLICATIONS

Clough et al. (1984), Small angle scattering from ampholytic styrene ionomers†. Polym Eng Sci, 24: 385-390. (Year: 1984).*
Asghar , et al., "Predicting Sizes of Hexagonal and Gyroid Metal Nanostructures from Liquid Crystal Templating", ACS Nano, 9, 2015, 10970.
Carter , et al., "Glycerol-Based Bicontinuous Cubic Lyotropic Liquid Crystal Monomer System for the Fabrication of Thin-Film Membranes with Uniform Nanopores", Chem. Mater., 24, 2012, 4005.
Dischinger , et al., "Application of a lyotropic liquid crystal nanofiltration membrane for hydraulic fracturing flowback water: Selectivity and implications for treatment", J. Membr. Sci., 543, 2017, 319.
Feng , et al., "Precise nanofiltration in a fouling-resistant self-assembled membrane with water-continuous transport pathways", Sci. Adv., 5, eaav9308., 2019.
Gao , et al., "The facile construction of an anion exchange membrane with 3D interconnected ionic nano-channels", Chem. Commun., 53, 2017, 767.
Gin , et al., "Polymerized Lyotropic Liquid Crystal Assemblies for Materials Applications", Acc. Chem. Res., 34, 2001, 973.
Gin , et al., "Recent Advances in the Design of Polymerizable Lyotropic Liquid-Crystal Assemblies for Heterogeneous Catalysis and Selective Separations", Adv. Funct. Mater., 16, 2006, 865.
Hatakeyama , et al., "Nanoporous, Bicontinuous Cubic Lyotropic Liquid Crystal Networks via Polymerizable Gemini Ammonium Surfactants", Chem. Mater., 22, 2010, 4525.
Hoag , et al., "Cross-Linkable Liquid Crystal Monomers Containing Hydrocarbon 1,3-Diene Tail Systems", Macromolecules, 33, 2000, 8549.
Jennings , et al., "Nanoporous Polymer Networks Templated by Gemini Surfactant Lyotropic Liquid Crystals", Chem. Mater., 30, 2018, 185.
Kerr , et al., "New Type of Li Ion Conductor with 3D Interconnected Nanopores via Polymerization of a Liquid Organic Electrolyte-Filled Lyotropic Liquid-Crystal Assembly", J. Am. Chem. Soc., 131, 2009, 15972.

(Continued)

*Primary Examiner* — Sanza L. McClendon
(74) *Attorney, Agent, or Firm* — Saul Ewing LLP; Domingos J. Silva; Dennis Ostrovsky

(57) ABSTRACT

The present disclosure relates, in part, to compositions comprising the compound of Formula (I), and polymerized compositions thereof. In certain embodiments, the compositions further comprise at least one compound of Formula (IIa) and Formula (IIb). In another aspect, the present disclosure relates to methods of preparation of the polymer compositions of the present disclosure, the method comprising contacting the compound of Formula (I) and a photoinitiator in the presence of a solvent to form a gyroid mesophase gel and irradiating the gyroid mesophase gel with UV light. In certain embodiments, the contacting further comprises at least one compound of Formula (IIa) and Formula (IIb).

19 Claims, 24 Drawing Sheets

(56) References Cited

OTHER PUBLICATIONS

Kobayashi , et al., "Gyroid structured aqua-sheets with sub-nanometer thickness enabling 3D fast proton relay conduction", Chem. Sci., 10, 2019, 6245.
Kobayashi , et al., "Gyroid-Nanostructured All-Solid Polymer Films Combining High H+ Conductivity with Low H2 Permeability", Macromol. Rapid Commun., 2100115, 2021.
Lee , et al., "Polymerization of Nonlaellar Lipid Assemblies", J. Am. Chem. Soc., 117, 1995, 5573.
Liu , et al., "Cross-Linking Polymerization in Two-Dimensional Assemblies: Effect of the Reactive Group Site", Macromolecules, 32, 1999, 5519.
Liu , et al., "Synthesis and Polymerization of Heterobifunctional Amphiphiles to Cross-Link Supramolecular Assemblies", Macromolecules, 34, 2001, 465.
Lu , et al., "Crosslinked Bicontinuous Cubic Lyotropic Liquid-Crystal/ Butyl-Rubber Composites: Highly Selective, Breathable Barrier Materials for Chemical Agent Protection", Adv. Mater., 18, 2006, 3294.
Maekawa , et al., "Gyroid nanostructured soft membranes formed by controlling the degree of crosslinking polymerization of bicontinuous cubic liquid-crystalline monomers", Polym. J., 53, 2021, 463.
McGrath , et al., "Polymerisation of liquid crystalline phases in binary surfactant/water systems", Colloid Polym. Sci., 274, 1996, 316.
Mueller , et al., "Supramolecular Materials via Polymerization of Mesophases of Hydrated Amphiphiles", Chem. Rev., 102, 2002, 727.
Pindzola , et al., "Cross-Linked Normal Hexagonal and Bicontinuous Cubic Assemblies via Polymerizable Gemini Amphiphiles", J. Am. Chem. Soc., 125, 2003, 2940.
Pindzola , et al., "Polymerization of a Phosphonium Diene Amphiphile in the Regular Hexagonal Phase with Retention of Mesostructure", J. Am. Chem. Soc., 123, 2001, 4617.
Sisson , et al., "Novel Polymer Architectures via the Selective Polymerization of Lyotropic Liquid Crystals of Heterobifunctional Amphiphiles", J. Am. Chem. Soc., 120, 1998, 2322.
Srisiri , et al., "Stabilization of a Bicontinuous Cubic Phase from Polymerizable Monoacylglycerol and Diacylglycerol", Langmuir, 14, 1998, 1921.
Takeuchi , et al., "Induction of bicontinuous cubic liquid-crystalline assemblies for polymerizable amphiphiles via tailor-made design of ionic liquids", Chem. Commun., 52, 2016, 13861.
Wiesenauer , et al., "Nanoporous polymer materials based on self-organized, bicontinuous cubic lyotropic liquid crystal assemblies and their applications", Polym. J, 44, 2012, 461.
Wu , et al., "Highly Ordered Interconnected 1 nm Pores in Polymers Fabricated from Easily Accessible Gyroid Liquid Crystals", Macromolecules, ASAP Article. doi.org/10.1021/acs.macromol.1c00721, 2021.
Yang , et al., "Polymerized Bicontinuous Cubic Nanoparticles (Cubosomes) from a Reactive Monoacylglycerol", J. Am. Chem. Soc., 124, 2002, 13388.
Zhang , et al., "From Channel-Forming lonic Liquid Crystals Exhibiting Humidity-Induced Phase Transitions to Nanostructured Ion-Conducting Polymer Membranes", Adv. Mater., 25, 2013, 3543.
Zhang , et al., "Rapid Fabrication by Lyotropic Self-Assembly of Thin Nanofiltration Membranes with Uniform 1 Nanometer Pores", ACS Nano, 15, 2021, 8192.

* cited by examiner

Monomer 1

Monomer 1b

DDMA Crosslinker

2SP

*cis*-2M-HBr

*trans*-2M-HBr

LYOTROPIC GYROID MESOPHASE COMPOSITIONS, POLYMER COMPOSITIONS COMPRISING THE SAME, METHODS OF PREPARATION THEREOF, AND METHODS OF USING THE SAME

CROSS-REFERENCE TO RELATED APPLICATIONS

The present application claims priority under 35 U.S.C. § 119(e) to U.S. Provisional Patent Application No. 63/246,143, filed Sep. 20, 2021, which is incorporated herein by reference in its entirety.

STATEMENT REGARDING FEDERALLY SPONSORED RESEARCH OR DEVELOPMENT

This invention was made with government support under grant numbers CB 10872 awarded by DOD/DTRA, and grant numbers CBET 2010890 and DMR-1945966 awarded by the National Science Foundation. The government has certain rights in the invention.

BACKGROUND

Lyotropic liquid crystal (LLC) networks are nanostructured cross-linked polymer materials with periodic, molecular-size pores that have been found to be useful for important applications such as templated synthesis, heterogeneous catalysis, molecular-size filtration, vapor transport, and enhanced ion transport. LLC networks are prepared by designing reactive (e.g., polymerizable) organic amphiphiles (e.g., LLC monomers) that, upon mixing with a polar liquid such as water, phase-separate into ordered but fluid arrays with monodisperse, nanoscale hydrophobic and hydrophilic domains (i.e., LLC phases). The resulting LLC phases are soft gels that can then be converted into physically robust solid materials by crosslinking the monomers. When properly executed, such cross-linking preserves the ordered nanostructure of the LLC phase, resulting in an ordered polymer network with nanoscale structure. Typically, the cross-linking occurs in the hydrophobic domains formed by the polymerizable tails of the amphiphilic monomers, leaving the water-filled hydrophilic domains to act as open pores for molecular transport, uptake, or functional group localization/concentration.

LLC phases, and the nanoporous polymer materials formed from them, have a range of dimensionalities and symmetries, depending on the structure and packing of the phase-separated domains formed by the amphiphiles. Close-packed normal (Type I) or inverted (Type II) cylindrical micelles form the 1D hexagonal (H) phases; stacks of planar sheets form the 2D lamellar (L) phase; and 3D-interpenetrating hydrophilic and hydrophobic domains separated by a cubic bicontinuous layer form the bicontinuous cubic (Q) phases (which can also be Type I (normal) or Type II (inverted)). Although formation of a particular LLC phase is primarily dependent upon system composition, specific LLC phases can also be favored to form via amphiphile design or by modulating system temperature and pressure. Pore size within a targeted phase can also be modified to a limited degree by careful adjustment of the same parameters. In addition to phase structure and pore size tunability, it is also possible to incorporate additional capabilities into LLC networks by including functional groups on the amphiphile headgroups that make up the walls of the pores. The ability to control both phase architecture and nanopore environment is one of the hallmarks of LLC networks as a class of functional organic nanomaterials.

Although numerous cross-linked LLC materials are known, Q-phase networks in particular are highly sought after for molecular separation and uptake applications. This is because Q phases possess 3D-interconnected nanopores that do not require macroscopic pore alignment for good transport or access as in the case of lower-dimensionality LLC phases such as the H and L phases. Q-phase LLC networks have been demonstrated to be useful for breathable toxic agent vapor rejection, water desalination, and enhanced ion-transport. However, only a very limited number of intrinsically cross-linkable Q-phase LLC monomer platforms have been reported that can be cross-linked with phase retention.

Q phases are more sensitive than lower-dimensionality LLC phases and require specific amphiphile structural motifs and precise amphiphile/solvent compositions in order to achieve a phase. As a result, Q-phase network materials have typically been designed from rather elaborate monomer motifs (i.e., symmetric gemini amphiphiles, wedge-shaped amphiphiles, and traditional lipid-like amphiphiles) that require complex/costly syntheses and are difficult to scale up.

There is thus a need in the art for LLC polymer compositions which are prepared from simple monomers and methods of preparation thereof. The present disclosure addresses these needs.

BRIEF SUMMARY OF THE INVENTION

In one aspect, the present disclosure provides a composition comprising a compound of Formula (I), or a solvate, stereoisomer, or isotopologue thereof:

(I)

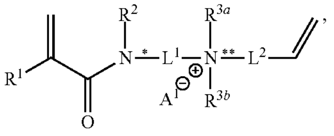

wherein $R^1$, $R^2$, $R^{3a}$, $R^{3b}$, $L^1$, $L^2$, and $A^1$ are defined elsewhere herein.

In certain embodiments, the composition further comprises at least one compound selected from the group consisting of:

(a) a compound of Formula (IIa), or solvate, stereoisomer, or isotopologue thereof:

(IIa)

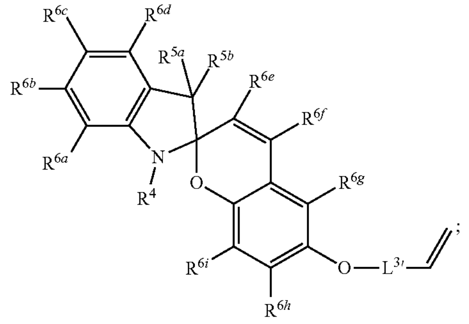

and (b) a compound of Formula (IIb), or solvate, stereoisomer, or isotopologue thereof:

(IIb)

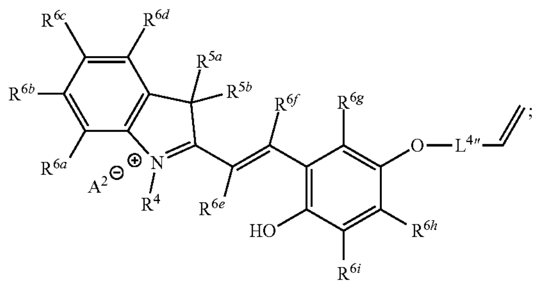

wherein $R^4$, $R^{5a}$, $R^{5b}$, $R^{6a}$, $R^{6b}$, $R^{6c}$, $R^{6d}$, $R^{6e}$, $R^{6f}$, $R^{6g}$, $R^{6h}$, $R^{6i}$, $L^3$, $L^4$, and $A^2$ are defined elsewhere herein.

In another aspect, the present disclosure provides a polymer composition comprising a polymerized product of the composition of the present disclosure, wherein the polymer composition comprises the reaction product of two or more compounds of Formula (I), wherein a covalent bond is formed between at least one alkene of a first compound of Formula (I) and at least one alkene of a second compound of Formula (I).

In another aspect, the present disclosure provides a polymer composition comprising a polymerized product of the composition of the present disclosure, wherein the polymer composition comprises the reaction product of two or more compounds selected from the group consisting of the compound of Formula (I), the compound of Formula (IIa), and/or the compound of Formula (IIb).

In another aspect, the present disclosure provides a method of preparing a polymer composition of the present disclosure, the method comprising:

(a) contacting the compound of Formula (I) and a photoinitiator in the presence of a solvent to provide a gyroid mesophase gel; and (b) irradiating the gyroid mesophase gel with UV light.

In another aspect, the present disclosure provides a method of preparing a polymer composition of the present disclosure, the method comprising:

(a) contacting the compound of Formula (I), the compound of Formula (IIa) and/or Formula (IIb), and a photoinitiator in the presence of a solvent to provide a gyroid mesophase gel; and (b) irradiating the gyroid mesophase gel with UV light.

BRIEF DESCRIPTION OF THE FIGURES

The drawings illustrate generally, by way of example, but not by way of limitation, various embodiments of the present application.

DETAILED DESCRIPTION OF THE INVENTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Description

Figure 9:
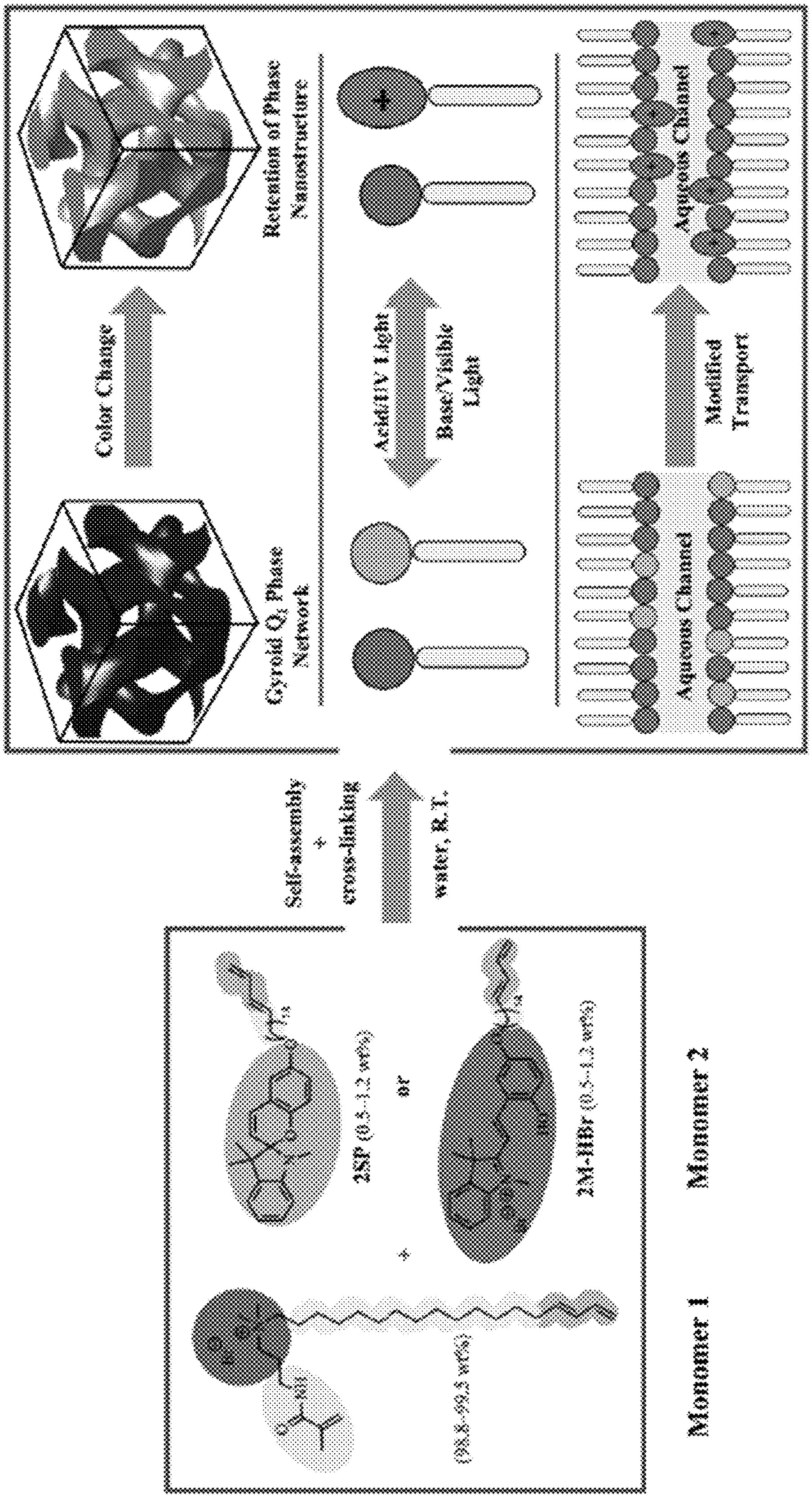
FIG. 9 provides structures of $Q_I$-phase-forming LLC monomer 1 and non-LLC-forming co-monomer platform 2 in spiropyran form (2SP) and its protonated merocyanine form (2M–HBr), comprising a hydrophilic region, hydrophobic region, polymerizable group, spiropyran group, and, in certain embodiments, a protonated merocyanine group. Various blends of (1+2SP) and (1+2M–HBr) self-assemble into gyroid type $Q_I$ phases that can be cross-linked in situ with retention of the phase order. The resulting nanoporous gyroid polymer networks undergo reversible physical changes in terms of color and unit cell dimensionality.
Figure 10A:
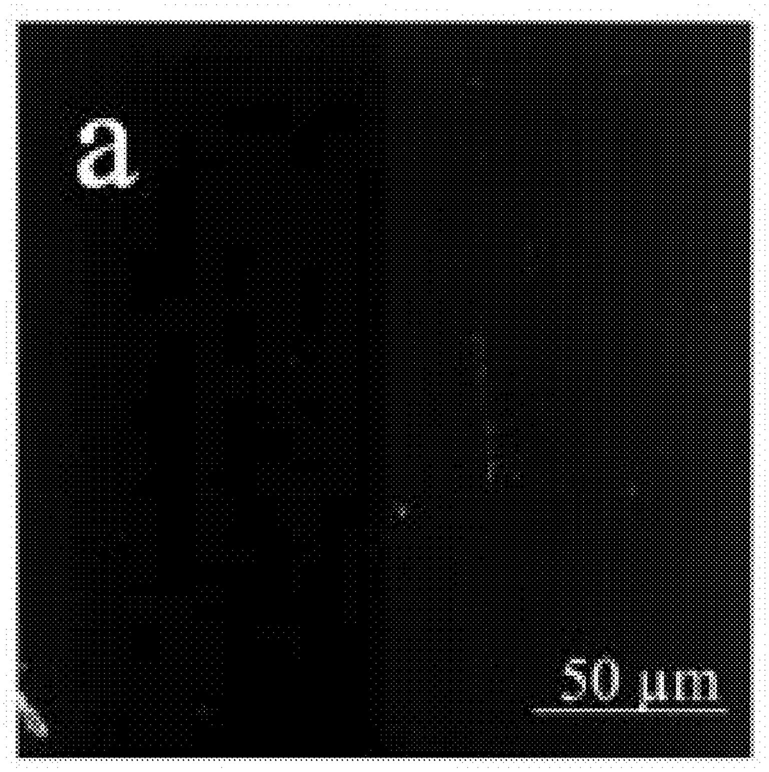
FIGS. 10A-10B provide PLM micrographs of the monomer mesophase (FIG. 10A) and a dry polymer film (FIG. 10B) observed between crossed polarizers.
Figure 10B:
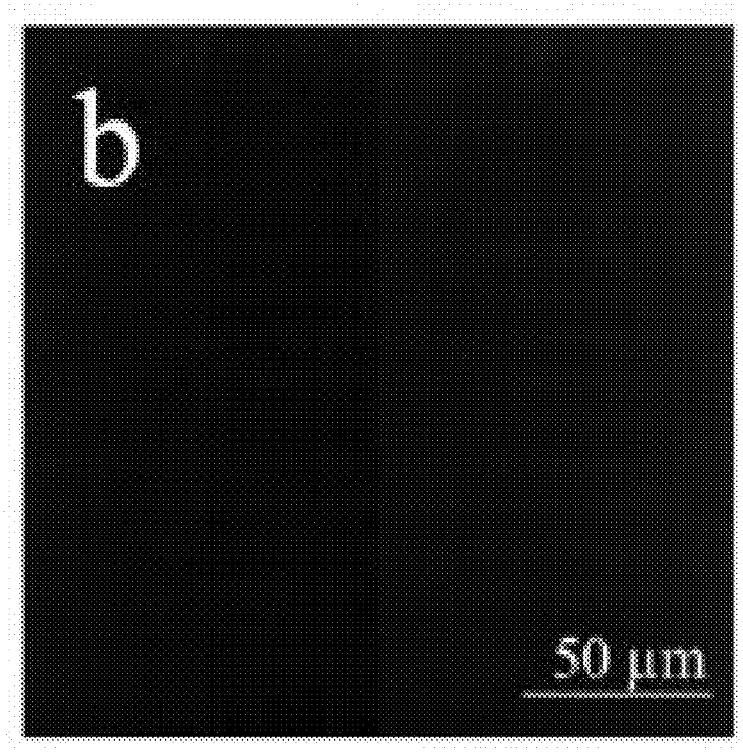
Figure 10C:
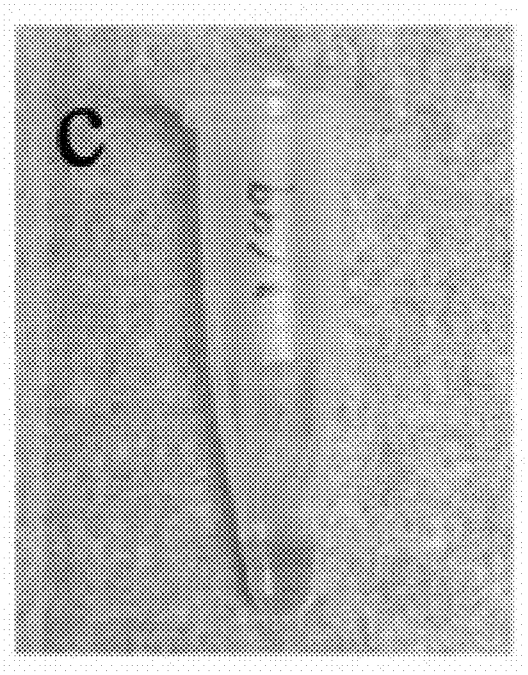
FIG. 10C provides a photo of the monomer mesophase blend pre-polymerization.
Figure 10D:
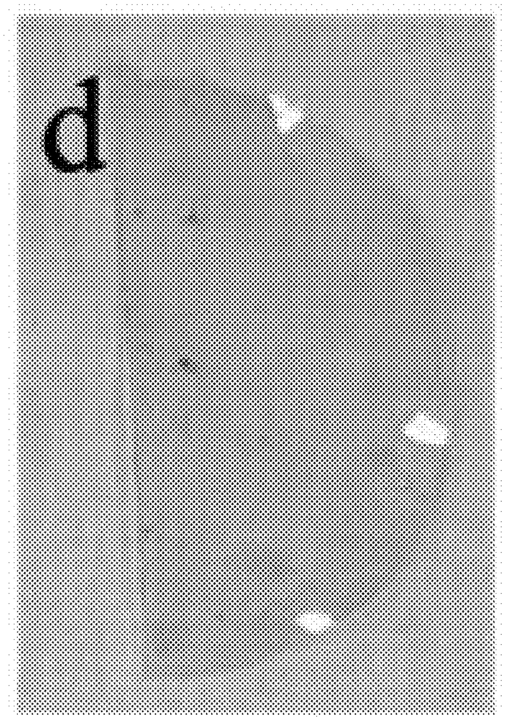
FIG. 10D provides a photo of the resulting cross-linked gyroid polymer film.
Figure 10E:
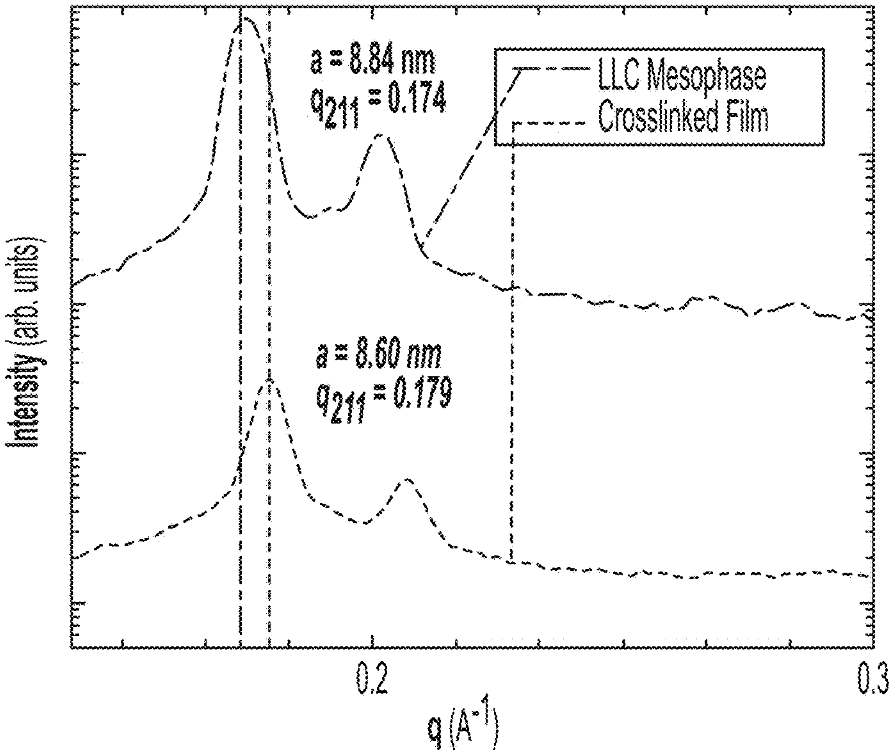
FIG. 10E provides a representative SAXS spectra of the monomer mesophase and cross-linked polymer films fabricated from 87.5/11.5/1.0 (w/w/w) monomer blend (1+2)/water/DMPA.

In one aspect, the present disclosure relates to the design and preparation of a a structurally simpler (i.e., single-head/single-tail), intrinsically cross-linkable Q phase-forming monomer motif (1) (FIG. 9). This monomer forms a Type I bicontinuous cubic (QI) phase with a gyroid-type unit cell. The resulting gyroid-type QI-phase polymer network formed from 1 exhibits excellent structural stability in a variety of aqueous and organic solvents, and like previous ionic Q LLC networks, is capable of molecular size and charge discrimination.

Because of this sensitivity to both environment and amphiphile chemical structure, Q-phase polymer networks, and mesogens, containing added functional properties or functional groups, other than polymerizable groups, are unprecedented. There have been no reported examples of a Q-phase network or monomer system with additional functional properties such as catalytic reactivity, response to external stimuli, or gated transport that have been demonstrated in lower-dimensionality LLC networks. Consequently, Q-phase networks have been limited to applications that rely solely on their bicontinuous nanopore architecture to perform molecular size separations, and/or charge discrimination if the monomers and pores are ionic.

One common avenue for introducing additional functional properties to materials is the inclusion of a stimuli-responsive group. For example, a convenient stimuli-responsive group that has been used in the design of polymer- and liquid-crystal-based functional materials is the spiropyran group, which is known for its unique chromic sensitivity to a variety of stimuli, including changes in pH, redox activity, temperature, and light. Specifically, spiropyran groups can reversibly convert from the uncharged spiropyran form (colorless) to the zwitterionic merocyanine form (red) in response to such changes in external conditions. Spiropyrans have also been incorporated into nanoparticles, biomolecules, metals, and polymer membranes to generate more responsive materials.

However, spiropyran-based responsive membranes, and functionalized responsive membranes in general, are typically fabricated via surface- or post-polymerization modification to introduce the functional groups. These modification strategies impart the desired responsive behavior, but the spiropyran groups added to a bulk material in this fashion can suffer from limitations arising from steric effects, aggregation, phase-separation, leaching, quenching, and reduced reactivity.

In another aspect, the present disclosure relates to the development and application of a spiropyran-containing Q-phase polymer network material that responds, within minutes, to changes in multiple external stimuli with retention of its phase architecture but with internal physical changes that allow it to be used in potential gated transport or responsive/sensing uptake applications. This gyroid-type QI-phase network is formed by blending and copolymerizing a new spiropyran-containing dopant monomer (2), in either its spiropyran (2SP) or protonated-merocyanine (2M–HBr) form, with QI-phase-forming, cross-linkable LLC monomer 1 (FIG. 9). The resulting nanoporous material was found to exhibit reversible color and gyroid unit cell dimensional changes with variations in external aqueous solution and vapor pH.

Correspondingly, the rate of water vapor transport through films of this material was modulated in response to such changes. Furthermore, preliminary studies indicate that the same $Q_I$ network material can be triggered with UV light in the presence of aq. $Pb^{2+}$ ions to irreversibly bind the $Pb^{2+}$ ions an stabilize the photo-generated colored merocyanine form, thereby allowing it to act as a potential colorimetric sorbent or gated-response material for certain types of metal ions. Thus, in one aspect, this disclosure relates to the discovery and development of unprecedented, functionalized Q-phase polymer networks with added functional properties.

Thus, in one aspect, the present disclosure provides a novel intrinsically cross-linkable surfactant motif for the formation of nanoporous polymer films with a gyroid Q-phase structure. SAXS and POM data confirm the successful retention of the gyroid nanostructure in the cross-linked polymer films. The benefit of having two polymerizable groups (as opposed to one) on the monomer is illustrated by comparing the long-term stability of the polymeric films upon water exposure. The solvent and temperature stabilities of the fabricated gyroid films indicate their potential for separations applications. Additionally, the transport performance (i.e., effective pore size based on rejection, and water permeability) of the fabricated gyroid films has been studied. The results motivate further study and optimization of this platform based on a novel LLC monomer motif.

Further, in another aspect, the present disclosure provides a functional bicontinuous gyroid polymer network material that responds to multiple external stimuli with retention of the porous nanostructure. This system consists of a small amount of a novel spiropyran-containing dopant monomer (2) that upon blending and cross-linking with a previously reported gyroid-phase-forming LLC monomer (1) yields a stimuli-responsive gyroid-type $Q_I$ network. Bulk films of this nanoporous polymer retain the gyroid structure while reversibly responding to changes in external solution and vapor pH via changes in color and unit cell dimensions as the spiropyran groups near the nanopores interconvert to their protonated-merocyanine form. This behavior allows the material to self-modulate its transport properties in situations such as diffusion and detection of HCl vapor. Upon UV irradiation, the spiropyran groups can also photoisomerize to the colored unprotonated-merocyanine form and irreversibly bind with aq. $Pb^{2+}$ ions, thereby allowing the polymer to act as a colorimetric sorbent for this metal ion.

This unique material may be fabricated into supported thin films with numerous applications. For example, it has been proposed that by altering the monomer composition and/or temperature to access other LLC mesophases of membrane interest (e.g., the $H_I$ phase) or by reducing the thickness of the original gyroid films, new molecular-size-selective film materials can be developed that have the intrinsic ability to visually detect and restrict the flow of hazardous vapors of interest for breathable chemical vapor barrier applications. In further embodiments, the phase space of the (1+2) system may be probed to increase the loading of the spiropyran monomer dopant tolerated within the gyroid phase so as to enhance the unit cell construction properties of the Q networks. In further embodiments, chemical modification and tuning of this system may allow future development of a reversible ion-uptake system in which cations of interest can be reversibly complexed within the network upon external light exposure.

Definitions

The term "about" as used herein can allow for a degree of variability in a value or range, for example, within 10%, within 5%, or within 1% of a stated value or of a stated limit of a range, and includes the exact stated value or range.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, $—CH═C═CCH_2$, $—CH═CH(CH_3)$, $—CH═C(CH_3)_2$, $—C(CH_3)═CH_2$, $—C(CH_3)═CH(CH_3)$, $—C(CH_2CH_3)═CH_2$, cyclohexenyl, cyclopentenyl, cyclohexadienyl, butadienyl, pentadienyl, and hexadienyl among others.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkylene" or "alkylenyl" as used herein refers to a bivalent saturated aliphatic radical (e.g., $—CH_2—$, $—CH_2CH_2—$, and $—CH_2CH_2CH_2—$, etc.). In certain embodiments, the term may be regarded as a moiety derived from an alkene by opening of the double bond or from an alkane by removal of two hydrogen atoms from the same (e.g., $—CH_2—$) different (e.g., $—CH_2CH_2—$) carbon atoms.

The term "alkenylenyl" as used herein refers to a bivalent radical containing at least one carbon-carbon double bond and optionally a saturated aliphatic moiety (e.g., $—CH═H—$, $—CH_2CH═CH—$, etc.). Thus, a $C_2$ alkenylenyl would have the structure $—CH═CH—$, a $C_3$ alkenylenyl would have the structure $—CH_2CH═CH—$, a $C_4$ alkenylenyl would have the structure $—CH_2CH_2CH═CH—$ or $—CH═CH—CH═CH—$, and so on.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to $—C≡CH$, $—C≡C(CH_3)$, $—C≡C(CH_2CH_3)$, $—CH_2C≡CH$, $—CH_2C≡C(CH_3)$, and $—CH_2C≡C(CH_2CH_3)$ among others.

The term "amine" as used herein refers to primary, secondary, and tertiary amines having, e.g., the formula $N(group)_3$ wherein each group can independently be H or non-H, such as alkyl, aryl, and the like. Amines include but are not limited to $R—NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, $—NHR$, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "atm" as used herein refers to a pressure in atmospheres under standard conditions. Thus, 1 atm is a pressure of 101 kPa, 2 atm is a pressure of 202 kPa, and so on.

The term "counter anion" as used herein refers to include any counter anions of inorganic and organic acids. Exemplary anions include, but are not limited to bromide, chloride, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl(2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heteroarylalkyl" as used herein refers to alkyl groups as defined herein in which a hydrogen or carbon bond of an alkyl group is replaced with a bond to a heteroaryl group as defined herein.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl ($C_1$), ethyl ($C_2$), propyl ($C_3$), or butyl ($C_4$), and $(C_0-C_b)$hydrocarbyl means in certain embodiments there is no hydrocarbyl group.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "monovalent" as used herein refers to a substituent connecting via a single bond to a substituted molecule. When a substituent is monovalent, such as, for example, F or Cl, it is bonded to the atom it is substituting by a single bond.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, $OC(O)N(R)_2$, CN, $CF_3$, $OCF_3$, R, C(O), methylenedioxy, ethylenedioxy, $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, C(=NOR)R, and substituted or unsubstituted $(C_1-C_{100})$hydrocarbyl, wherein R can be hydrogen (in examples that include other carbon atoms) or a carbon-based moiety, and wherein the carbon-based moiety can be substituted or unsubstituted.

The term "room temperature" as used herein refers to a temperature of about 15° C. to 28° C.

The term "solvent" as used herein refers to a liquid that can dissolve a solid, liquid, or gas. Non-limiting examples of solvents are silicones, organic compounds, water, alcohols, ionic liquids, and supercritical fluids.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$) hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

Compositions

In one aspect, the present disclosure provides a composition comprising a compound of Formula (I), or a solvate, stereoisomer, salt, or isotopologue thereof:

(I)

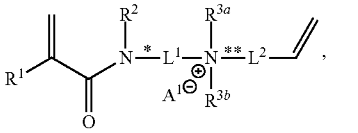

wherein:

$R^1$ is selected from the group consisting of hydrogen, halogen, CN, NO$_2$, optionally substituted C$_1$-C$_6$ alkyl, optionally substituted C$_1$-C$_6$ alkoxy, optionally substituted C$_6$-C$_{10}$ aryl, and optionally substituted C$_5$-C$_{10}$ heteroaryl;

$R^2$ is independently selected from the group consisting of hydrogen, halogen, CN, NO$_2$, optionally substituted C$_1$-C$_6$ alkyl, optionally substituted C$_1$-C$_6$ alkoxy, optionally substituted C$_6$-C$_{10}$ aryl, and optionally substituted C$_5$-C$_{10}$ heteroaryl;

$R^{3a}$ and $R^{3b}$ are each independently selected from the group consisting of hydrogen, halogen, CN, NO$_2$, optionally substituted C$_1$-C$_6$ alkyl, optionally substituted C$_1$-C$_6$ alkoxy, optionally substituted C$_6$-C$_{10}$ aryl, and optionally substituted C$_5$-C$_{10}$ heteroaryl;

$L^1$ is selected from the group consisting of optionally substituted C$_1$-C$_{10}$ alkylenyl and optionally substituted C$_2$-C$_{10}$ alkenylenyl;

$L^2$ is selected from the group consisting of optionally substituted C$_1$-C$_{100}$ alkylenyl and optionally substituted C$_2$-C$_{100}$ alkenylenyl; and $A^1$ is a counter anion.

In certain embodiments, $R^1$ is CH$_3$.

In certain embodiments, $R^2$ is H.

In certain embodiments, $R^{3a}$ is CH$_3$. In certain embodiments, $R^{3b}$ is CH$_3$.

In certain embodiments, $L^1$ is *—CH$_2$CH$_2$CH$_2$—. In certain embodiments, $L^1$ is *—(CH$_2$)—. In certain embodiments, $L^1$ is *—(CH$_2$)$_2$—. In certain embodiments, $L^1$ is *—(CH$_2$)$_3$—. In certain embodiments, $L^1$ is *—(CH$_2$)$_4$—. In certain embodiments, $L^1$ is *—(CH$_2$)$_5$—. In certain embodiments, $L^1$ is *—(CH$_2$)$_6$—. In certain embodiments, $L^1$ is *—(CH$_2$)$_7$—. In certain embodiments, $L^1$ is *—(CH$_2$)$_8$—. In certain embodiments, $L^1$ is *—(CH$_2$)$_9$—. In certain embodiments, $L^1$ is *—(CH$_2$)$_{10}$—. The open valence marked * in $L^1$ is attached to the corresponding * in the compound of Formula (I) as defined herein.

In certain embodiments, $L^2$ is —(CH$_2$)$_{14}$CH=CH—. In certain embodiments, $L^2$ is —(CH$_2$)$_{1-20}$CH=CH—. In certain embodiments, $L^2$ is —(CH$_2$)$_{20-40}$CH=H—. In certain embodiments, $L^2$ is —(CH$_2$)$_{40-60}$CH=CH—. In certain embodiments, $L^2$ is —(CH$_2$)$_{60-80}$CH=CH—. In certain embodiments, $L^2$ is —(CH$_2$)$_{80-99}$CH=CH—. The open valence marked  in $L^2$ is attached to the corresponding  in the compound of Formula (I) as defined herein.

In certain embodiments, $A^1$ is bromide. In certain embodiments, $A^1$ is chloride. In certain embodiments, $A^1$ is iodide. In certain embodiments, $A^1$ is triflate. In certain embodiments, $A^1$ is acetate. In certain embodiments, $A^1$ is p-toluenesulfonate.

In certain embodiments, the compound of Formula (I) is:

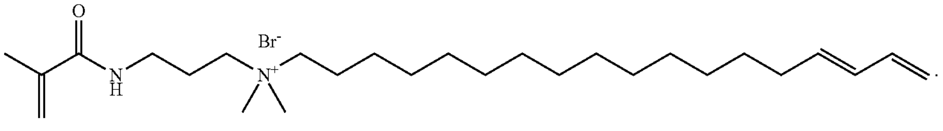

In certain embodiments, the compound of Formula (I) comprises about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the composition by weight (w/w %). In certain embodiments, the compound of Formula (I) comprises less than about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the composition by weight (w/w %). In certain embodiments, the compound of Formula (I) comprises more than about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the composition by weight (w/w %).

In certain embodiments, the composition further comprises a solvent. In certain embodiments, the solvent is water. In certain embodiments, the water is deionized water. In certain embodiments, the water comprises a salt, such an alkali chloride or alkali bromide, for example, NaCl and LiCl.

In certain embodiments, the solvent comprises about 5, 6, 7, 8, 9, 10, 11, 12, 13, 14, or about 15% of the composition by weight (w/w %). In certain embodiments, the solvent comprises less than about 5, 6, 7, 8, 9, 10, 11, 12, 13, 14, or about 15% of the composition by weight (w/w %). In certain embodiments, the solvent comprises more than about 5, 6, 7, 8, 9, 10, 11, 12, 13, 14, or about 15% of the composition by weight (w/w %).

In certain embodiments, the compound of Formula (I) and the water have a ratio selected from the group consisting of about 80:11, 81:11, 82:11, 83:11, 84:11, 85:11, 86:11, 87:11, 88:11, 89:11, 90:11, 91:11, 92:11, 93:11, 94:11, or about 95:11 by weight.

In certain embodiments, the compound of Formula (I) and the water have a ratio selected from the group consisting of less than about 80:11, 81:11, 82:11, 83:11, 84:11, 85:11, 86:11, 87:11, 88:11, 89:11, 90:11, 91:11, 92:11, 93:11, 94:11, or about 95:11 by weight.

In certain embodiments, the compound of Formula (I) and the water have a ratio selected from the group consisting of more than about 80:11, 81:11, 82:11, 83:11, 84:11, 85:11, 86:11, 87:11, 88:11, 89:11, 90:11, 91:11, 92:11, 93:11, 94:11, or about 95:11 by weight.

In certain embodiments, the compound of Formula (I) and the water have a ratio selected from the group consisting of about 87.5:11.5, 88:11, and 84:11 by weight.

In certain embodiments, the compound of Formula (I) and the water have a ratio selected from the group consisting of less than about 87.5:11.5, 88:11, and 84:11 by weight.

In certain embodiments, the compound of Formula (I) and the water have a ratio selected from the group consisting of more than about 87.5:11.5, 88:11, and 84:11 by weight.

In certain embodiments, the composition further comprises a compound of Formula (IIa), or solvate, stereoisomer, salt, or isotopologue thereof:

(IIa)

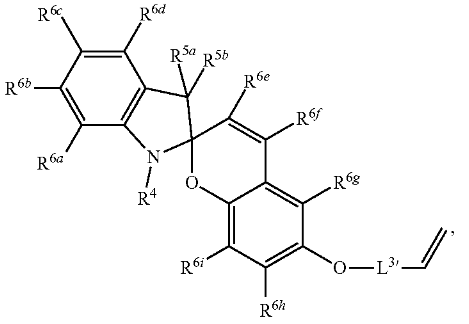

wherein:

each occurrence of $R^4$ is selected from the group consisting of H, optionally substituted $C_1$-$C_6$ alkyl, optionally substituted $C_3$-$C_8$ cycloalkyl, optionally substituted $C_2$-$C_8$ heterocycloalkyl, optionally substituted $C_6$-$C_{10}$ aryl, and optionally substituted $C_5$-$C_{10}$ heteroaryl;

each occurrence of $R^{5a}$ and $R^{5b}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

each occurrence of $R^{6a}$, $R^{6b}$, $R^{6c}$, $R^{6d}$, $R^{6e}$, $R^{6f}$, $R^{6g}$, $R^{6h}$, and $R^{6i}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^3$ and $L^4$ are each independently selected from the group consisting of optionally substituted $C_1$-$C_{100}$ alkylenyl and optionally substituted $C_2$-$C_{100}$ alkenylenyl; and $A^2$ is a counter anion.

In certain embodiments, the composition further comprises a compound of Formula (IIb), or solvate, stereoisomer, salt, or isotopologue thereof:

(IIb)

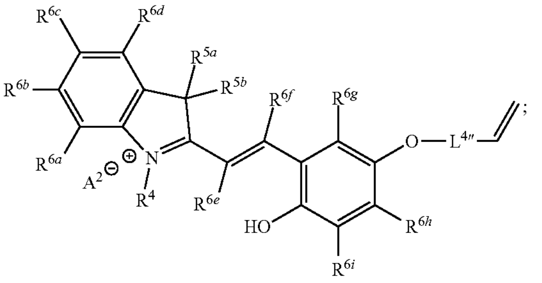

wherein:

each occurrence of $R^4$ is selected from the group consisting of H, optionally substituted $C_1$-$C_6$ alkyl, optionally substituted $C_3$-$C_8$ cycloalkyl, optionally substituted $C_2$-$C_8$ heterocycloalkyl, optionally substituted $C_6$-$C_{10}$ aryl, and optionally substituted $C_5$-$C_{10}$ heteroaryl;

each occurrence of $R^{5a}$ and $R^{5b}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

each occurrence of $R^{6a}$, $R^{6b}$, $R^{6c}$, $R^{6d}$, $R^{6e}$, $R^{6f}$, $R^{6g}$, $R^{6h}$, and $R^{6i}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^3$ and $L^4$ are each independently selected from the group consisting of optionally substituted $C_1$-$C_{100}$ alkylenyl and optionally substituted $C_2$-$C_{100}$ alkenylenyl; and $A^2$ is a counter anion.

In certain embodiments, the composition further comprises the compound of Formula (IIa) and the compound of Formula (IIb). In certain embodiments, the composition comprises a mixture of the compound of Formula (IIa) and the compound of Formula (IIb).

In certain embodiments, $R^4$ is $CH_3$.

In certain embodiments, $R^{5a}$ is $CH_3$. In certain embodiments, $R^{5b}$ is $CH_3$.

In certain embodiments, $R^{6a}$ is H. In certain embodiments, $R^{6b}$ is H. In certain embodiments, $R^{6c}$ is H. In certain embodiments, $R^{6d}$ is H. In certain embodiments, $R^{6e}$ is H. In certain embodiments, $R^{6f}$ is H. In certain embodiments, $R^{6g}$ is H. In certain embodiments, $R^{6h}$ is H. In certain embodiments, $R^{6i}$ is H.

In certain embodiments, $L^3$ is $—(CH_2)_{14}CH═CH$-'. In certain embodiments, $L^3$ is $—(CH_2)_{1\text{-}20}CH═CH$-'. In certain embodiments, $L^3$ is $—(CH_2)_{20\text{-}40}CH═CH$-'. In certain embodiments, $L^3$ is $—(CH_2)_{40\text{-}60}CH═CH$-'. In certain embodiments, $L^3$ is $—(CH_2)_{60\text{-}80}CH═CH$-'. In certain embodiments, $L^3$ is **$—(CH_2)_{80\text{-}99}CH═CH$-'. The open valence marked ' in $L^3$ is attached to the corresponding ' in the compound of Formula (IIa) as defined herein.

In certain embodiments, $L^4$ is $—(CH_2)_{14}CH═CH—$. ". In certain embodiments, $L^4$ is $—(CH_2)_{1\text{-}20}CH═CH$-". In certain embodiments, $L^4$ is $—(CH_2)_{20\text{-}40}CH═CH$-". In certain embodiments, $L^4$ is $—(CH_2)_{40\text{-}60}CH═CH$-". In certain embodiments, $L^4$ is $—(CH_2)_{60\text{-}80}CH═CH$-". In certain embodiments, $L^4$ is **$—(CH_2)_{80\text{-}99}CH═CH$-". The open valence marked " in $L^4$ is attached to the corresponding " in the compound of Formula (IIb) as defined herein.

In certain embodiments, $A^2$ is bromide. In certain embodiments, $A^2$ is chloride. In certain embodiments, $A^2$ is iodide. In certain embodiments, $A^2$ is triflate. In certain embodiments, $A^2$ is acetate. In certain embodiments, $A^2$ is p-toluenesulfonate.

In certain embodiments, in the compound of Formula (IIa), $L^3$ is $—(CH_2)_nCH═CH$-', wherein n is 6. In certain embodiments, in the compound of Formula (IIa), $L^3$ is $—(CH_2)_nCH═CH$-', wherein n is 7. In certain embodiments, in the compound of Formula (IIa), $L^3$ is $—(CH_2)_nCH═CH$-', wherein n is 8. In certain embodiments, in the compound of Formula (IIa), $L^3$ is $—(CH_2)_nCH═CH$-', wherein n is 9. In certain embodiments, in the compound of Formula (IIa), $L^3$ is $—(CH_2)_nCH═CH$-', wherein n is 10. In certain embodiments, in the compound of Formula (IIa), $L^3$ is $—(CH_2)_nCH═CH$-', wherein n is 11. In certain embodiments, in the compound of Formula (IIa), $L^3$ is $—(CH_2)_nCH═CH$-', wherein n is 12. In certain embodiments, in the compound of Formula (IIa), $L^3$ is $—(CH_2)_nCH═CH$-', wherein n is 13. In certain embodiments, in the compound of Formula (IIa), $L^3$ is $—(CH_2)_nCH═CH$-', wherein n is 14. In certain embodiments, in the compound of Formula (IIa), $L^3$ is $—(CH_2)_nCH═CH$-', wherein n is 15. In certain embodiments, in the compound of Formula (IIa), $L^3$ is $—(CH_2)_nCH═CH$-', wherein n is 16. In certain embodiments, in the compound of Formula (IIa), $L^3$ is $—(CH_2)_nCH═CH$-', wherein n is 17. In certain embodiments, in the compound of Formula (IIa), $L^3$ is $—(CH_2)_nCH═CH$-', wherein n is 18. In certain embodiments, in the compound of Formula (IIa), $L^3$ is $—(CH_2)_nCH═CH$-', wherein n is 19. In certain embodiments, in the compound of Formula (IIa), $L^3$ is $—(CH_2)_nCH═CH$-', wherein n is 20.

In certain embodiments, in the compound of Formula II(b), $L^4$ is $—(CH_2)_nCH═CH$-", wherein n is 6. In certain embodiments, in the compound of Formula (IIb), $L^4$ is $—(CH_2)_nCH═CH$-", wherein n is 7. In certain embodiments, in the compound of Formula (IIb), $L^4$ is $—(CH_2)_nCH═CH$-", wherein n is 8. In certain embodiments, in the compound of Formula (IIb), $L^4$ is $—(CH_2)_nCH═CH$-", wherein n is 9. In certain embodiments, in the compound of Formula (IIb), $L^4$ is $—(CH_2)_nCH═CH$-", wherein n is 10. In certain embodiments, in the compound of Formula (IIb), $L^4$ is $—(CH_2)_nCH═CH$-", wherein n is 11. In certain embodiments, in the compound of Formula (IIb), $L^4$ is $—(CH_2)_nCH═CH$-", wherein n is 12. In certain embodiments, in the compound of Formula (IIb), $L^4$ is $—(CH_2)_nCH═CH$-", wherein n is 13. In certain embodiments, in the compound of Formula (IIb), $L^4$ is $—(CH_2)_nCH═CH$-", wherein n is 14. In certain embodiments, in the compound of Formula (IIb), $L^4$ is $—(CH_2)_nCH═CH$-", wherein n is 15. In certain embodiments, in the compound of Formula (IIb), $L^4$ is $—(CH_2)_nCH═CH$-", wherein n is 16. In certain embodiments, in the compound of Formula (IIb), $L^4$ is $—(CH_2)_nCH═CH$-", wherein n is 17. In certain embodiments, in the compound of Formula (IIb), $L^4$ is $—(CH_2)_nCH═CH$-", wherein n is 18. In certain embodiments, in the compound of Formula (IIb), $L^4$ is $—(CH_2)_nCH═CH$-", wherein n is 19. In certain embodiments, in the compound of Formula (IIb), $L^4$ is $—(CH_2)_nCH═CH$-", wherein n is 20.

In certain embodiments, the compound of Formula (IIa) is:

(IIa)

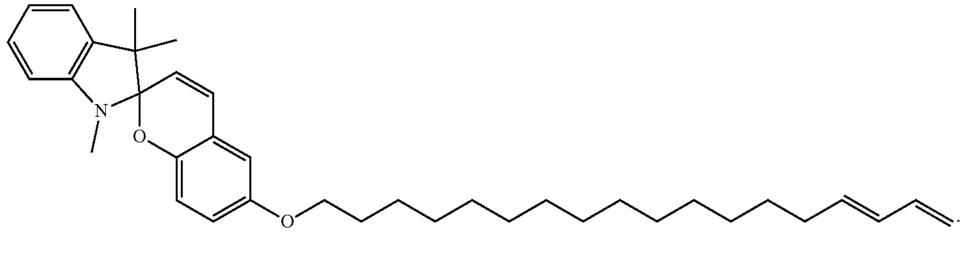

In certain embodiments, the compound of Formula (IIb) is:

(IIb)

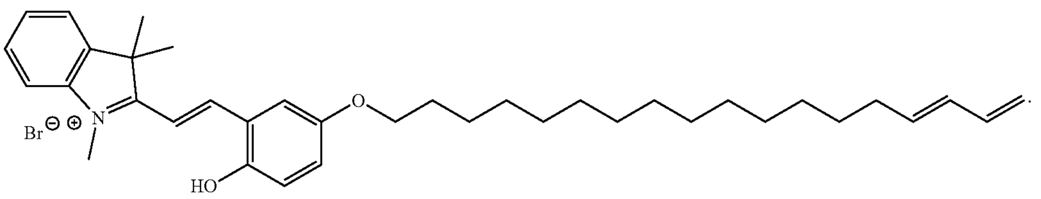

In certain embodiments, the compound of Formula (IIa) and/or Formula (IIb) comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIa) and/or Formula (IIb) comprises less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIa) and/or Formula (IIb) comprises more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIa) comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIa) comprises less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIa) comprises more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIb) comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIb) comprises less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIb) comprises more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (I) and the compound of Formula (IIa) and/or Formula (IIb) have a ratio of about 80:1, 81:1, 82:1, 83:1, 84:1, 85:1, 86:1, 87:1, 88:1, 89:1 90:1 by weight. In certain embodiments, the compound of Formula (I) and the compound of Formula (IIa) and/or Formula (IIb) have a ratio of less than about 80:1, 81:1, 82:1, 83:1, 84:1, 85:1, 86:1, 87:1, 88:1, 89:1 90:1 by weight. In certain embodiments, the compound of Formula (I) and the compound of Formula (IIa) and/or Formula (IIb) have a ratio of more than about 80:1, 81:1, 82:1, 83:1, 84:1, 85:1, 86:1, 87:1, 88:1, 89:1 90:1 by weight.

In certain embodiments, the compound of Formula (I) and the compound of Formula (IIa) and/or Formula (IIb) have a ratio of about 86.5:1 by weight (w/w %). In certain embodiments, the compound of Formula (I) and the compound of Formula (IIa) and/or Formula (IIb) have a ratio less than of about 86.5:1 by weight (w/w %). In certain embodiments, the compound of Formula (I) and the compound of Formula (IIa) and/or Formula (IIb) have a ratio of more than about 86.5:1 by weight (w/w %).

In certain embodiments, the compound of Formula (I) and the compound of Formula (IIa) have a ratio of about 86.5:1 by weight (w/w %). In certain embodiments, the compound of Formula (I) and the compound of Formula (IIa) have a ratio less than of about 86.5:1 by weight (w/w %). In certain embodiments, the compound of Formula (I) and the compound of Formula (IIa) have a ratio of more than about 86.5:1 by weight (w/w %).

In certain embodiments, the compound of Formula (I) and the compound of Formula (IIb) have a ratio of about 86.5:1 by weight (w/w %). In certain embodiments, the compound of Formula (I) and the compound of Formula (IIb) have a ratio less than of about 86.5:1 by weight (w/w %). In certain embodiments, the compound of Formula (I) and the compound of Formula (IIb) have a ratio of more than about 86.5:1 by weight (w/w %).

In moieties or substituents designated as optionally substituted herein, the optional substitution, in certain embodiments, is selected from the group consisting of F, Cl, Br, I, OR, $OC(O)N(R)_2$, CN, NO, $NO_2$, $ONO_2$, azido, $CF_3$, $OCF_3$, R, O (oxo), S (thiono), C(O), S(O), $N(R)_2$, SR, SOR, $SO_2R$, $SO_2N(R)_2$, $SO_3R$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, where R is at each occurrence independently selected from the group consisting of H an $C_{1-10}$ alkyl.

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound(s) described herein, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compound(s) described herein can exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compound(s) described herein are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}c$, $^{13}C$, $^{14}C$, $^{36}Cl$, $^{18}F$, $^{123}I$, $^{125}I$, $^{13}N$, 15N, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

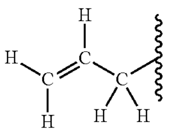
allyl

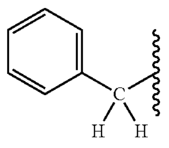
Bn

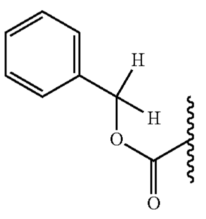
Cbz

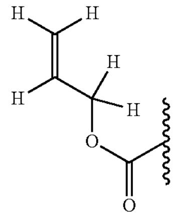
Alloc

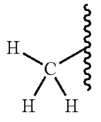
Me

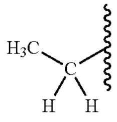
Et

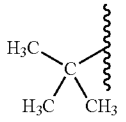
t-butyl

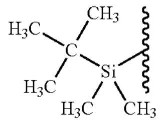
TBDMS

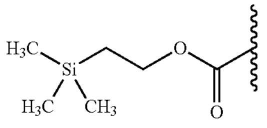
Teoc

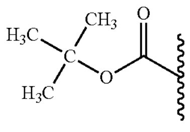
Boc

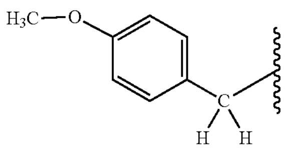
PMB

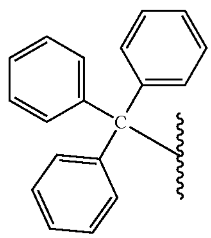
trityl

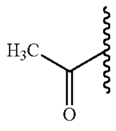
acetyl

-continued

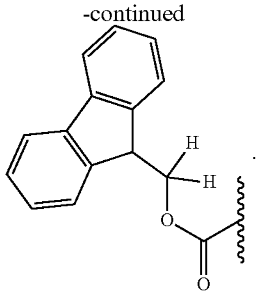
FMOC

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Polymer Compositions

In another aspect, the present disclosure provides a polymer composition comprising a polymerized product of a compound of Formula (I), or a solvate, stereoisomer, salt, or isotopologue thereof:

(I)

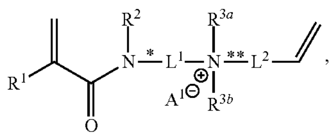

wherein:

$R^1$ is selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^2$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^{3a}$ and $R^{3b}$ are each independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^1$ is selected from the group consisting of optionally substituted $C_1$-$C_{10}$ alkylenyl and optionally substituted $C_2$-$C_{10}$ alkenylenyl;

$L^2$ is selected from the group consisting of optionally substituted $C_1$-$C_{100}$ alkylenyl and optionally substituted $C_2$-$C_{100}$ alkenylenyl; and $A^1$ is a counter anion.

In certain embodiments, $R^1$ is $CH_3$.

In certain embodiments, $R^2$ is H.

In certain embodiments, $R^{3a}$ is $CH_3$. In certain embodiments, $R^{3b}$ is $CH_3$.

In certain embodiments, $L^1$ is *—$CH_2CH_2CH_2$—. In certain embodiments, $L^1$ is *—$(CH_2)$—. In certain embodiments, $L^1$ is *—$(CH_2)_2$—. In certain embodiments, $L^1$ is *—$(CH_2)_4$—. In certain embodiments, $L^1$ is *—$(CH_2)_5$—. In certain embodiments, $L^1$ is *—$(CH_2)_6$—. In certain embodiments, $L^1$ is $*—(CH_2)_7—$. In certain embodiments, $L^1$ is $*—(CH_2)_8—$. In certain embodiments, $L^1$ is $*—(CH_2)_9—$. In certain embodiments, $L^1$ is $*—(CH_2)_{10}—$.

In certain embodiments, $L^2$ is $—(CH_2)_{14}CH{=}CH—$. In certain embodiments, $L^2$ is $—(CH_2)_{1\text{-}20}CH{=}CH—$. In certain embodiments, $L^2$ is $—(CH_2)_{20\text{-}40}CH{=}CH—$. In certain embodiments, $L^2$ is $—(CH_2)_{40\text{-}60}CH{=}CH—$. In certain embodiments, $L^2$ is $—(CH_2)_{60\text{-}80}CH{=}CH—$. In certain embodiments, $L^2$ is $—(CH_2)_{80\text{-}99}CH{=}CH—$.

In certain embodiments, $A^1$ is bromide. In certain embodiments, $A^1$ is chloride. In certain embodiments, $A^1$ is iodide. In certain embodiments, $A^1$ is triflate. In certain embodiments, $A^1$ is acetate. In certain embodiments, $A^1$ is p-toluenesulfonate.

In certain embodiments, the compound of Formula (I) is:

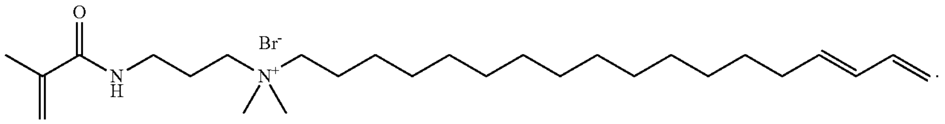 [SMILES: C=C/C=C/CCCCCCCCCCCCCC[N+](C)(C)CCCNC(=O)C(=C)C ; [Br-]]

In certain embodiments, the compound of Formula (I) comprises about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the composition by weight (w/w %). In certain embodiments, the compound of Formula (I) comprises less than about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the composition by weight (w/w %). In certain embodiments, the compound of Formula (I) comprises more than about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the composition by weight (w/w %).

In certain embodiments, the composition further comprises a solvent. In certain embodiments, the solvent is water. In certain embodiments, the water is deionized water. In certain embodiments, the water comprises a salt, including but not limited to NaCl and LiCl.

In certain embodiments, the solvent comprises about 5, 6, 7, 8, 9, 10, 11, 12, 13, 14, or about 15% of the composition by weight (w/w %). In certain embodiments, the solvent comprises less than about 5, 6, 7, 8, 9, 10, 11, 12, 13, 14, or about 15% of the composition by weight (w/w %). In certain embodiments, the solvent comprises more than about 5, 6, 7, 8, 9, 10, 11, 12, 13, 14, or about 15% of the composition by weight (w/w %).

In certain embodiments, the compound of Formula (I) and the water have a ratio selected from the group consisting of about 80:11, 81:11, 82:11, 83:11, 84:11, 85:11, 86:11, 87:11, 88:11, 89:11, 90:11, 91:11, 92:11, 93:11, 94:11, or about 95:11 by weight.

In certain embodiments, the compound of Formula (I) and the water have a ratio selected from the group consisting of less than about 80:11, 81:11, 82:11, 83:11, 84:11, 85:11, 86:11, 87:11, 88:11, 89:11, 90:11, 91:11, 92:11, 93:11, 94:11, or about 95:11 by weight.

In certain embodiments, the compound of Formula (I) and the water have a ratio selected from the group consisting of more than about 80:11, 81:11, 82:11, 83:11, 84:11, 85:11, 86:11, 87:11, 88:11, 89:11, 90:11, 91:11, 92:11, 93:11, 94:11, or about 95:11 by weight.

In certain embodiments, the compound of Formula (I) and the water have a ratio selected from the group consisting of about 87.5:11.5, 88:11, and 84:11 by weight.

In certain embodiments, the compound of Formula (I) and the water have a ratio selected from the group consisting of less than about 87.5:11.5, 88:11, and 84:11 by weight.

In certain embodiments, the compound of Formula (I) and the water have a ratio selected from the group consisting of more than about 87.5:11.5, 88:11, and 84:11 by weight.

In certain embodiments, the polymer composition comprises the reaction product of two or more compounds of Formula (I), wherein a covalent bond is formed between at least one alkene of a first compound of Formula (I) and at least one alkene of a second compound of Formula (I).

In certain embodiments, wherein the polymer comprises a plurality of nanoholes. In certain embodiments, the nanoholes have a diameter of about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm. In certain embodiments, the nanoholes have a diameter of less than about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm. In certain embodiments, the nanoholes have a diameter of more than about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm.

In certain embodiments, the polymer comprises an aqueous lyotropic liquid crystal (LLC) phase.

In certain embodiments, the LLC phase comprises a gyroid bicontinuous cubic (Q-phases) morphology.

In another aspect, the present disclosure provides a polymer composition comprising a polymerized product of:

(a) a compound of Formula (I), or a solvate, stereoisomer, salt, or isotopologue thereof:

(I)

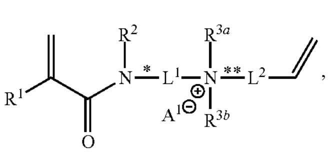

wherein:

$R^1$ is selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^2$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^{3a}$ and $R^{3b}$ are each independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^1$ is selected from the group consisting of optionally substituted $C_1$-$C_{10}$ alkylenyl and optionally substituted $C_1$-$C_{10}$ alkenylenyl;

$L^2$ is selected from the group consisting of optionally substituted $C_1$-$C_{100}$ alkylenyl and optionally substituted $C_2$-$C_{100}$ alkenylenyl;

$A^1$ is a counter anion; and (b) a compound of Formula (IIa), or solvate, stereoisomer, salt, or isotopologue thereof:

(IIa)

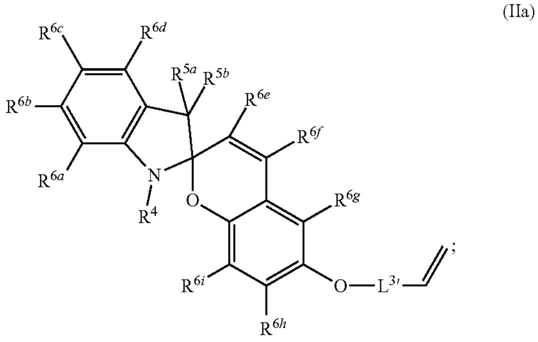

(c) a compound of Formula (IIb), or solvate, stereoisomer, salt, or isotopologue thereof:

(IIb)

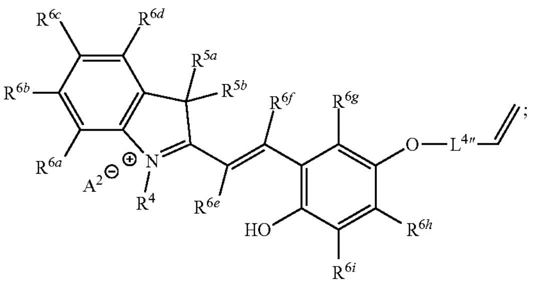

wherein:

each occurrence of $R^4$ is selected from the group consisting of H, optionally substituted $C_1$-$C_6$ alkyl, optionally substituted $C_3$-$C_8$ cycloalkyl, optionally substituted $C_2$-$C_8$ heterocycloalkyl, optionally substituted $C_6$-$C_{10}$ aryl, and optionally substituted $C_5$-$C_{10}$ heteroaryl;

each occurrence of $R^{5a}$ and $R^{5b}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

each occurrence of $R^{6a}$, $R^{6b}$, $R^{6c}$, $R^{6d}$, $R^{6e}$, $R^{6f}$, $R^{6g}$, $R^{6h}$, and $R^{6i}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^3$ and $L^4$ are each independently selected from the group consisting of optionally substituted $C_1$-$C_{100}$ alkylenyl and optionally substituted $C_2$-$C_{100}$ alkenylenyl; and $A^2$ is a counter anion.

In certain embodiments, the composition further comprises the compound of Formula (IIa) and the compound of Formula (IIb). In certain embodiments, the composition comprises one of the compound of Formula (IIa) and the compound of Formula (IIb).

In certain embodiments, $R^4$ is $CH_3$.

In certain embodiments, $R^{5a}$ is $CH_3$. In certain embodiments, $R^{5b}$ is $CH_3$.

In certain embodiments, $R^{6a}$ is H. In certain embodiments, $R^{6b}$ is H. In certain embodiments, $R^{6c}$ is H. In certain embodiments, $R^{6d}$ is H. In certain embodiments, $R^{6e}$ is H. In certain embodiments, $R^{6f}$ is H. In certain embodiments, $R^{6g}$ is H. In certain embodiments, $R^{6h}$ is H. In certain embodiments, $R^{6i}$ is H.

In certain embodiments, $L^3$ is $—(CH_2)_{14}CH{=}CH$-'. In certain embodiments, $L^3$ is $—(CH_2)_{1\text{-}20}CH{=}CH$-'. In certain embodiments, $L^3$ is $—(CH_2)_{20\text{-}40}CH{=}CH$-'. In certain embodiments, $L^3$ is $—(CH_2)_{40\text{-}60}CH{=}CH$-'. In certain embodiments, $L^3$ is $—(CH_2)_{60\text{-}80}CH{=}CH$-'. In certain embodiments, $L^3$ is **$—(CH_2)_{80\text{-}99}CH{=}CH$-'.

In certain embodiments, $L^4$ is $—(CH_2)_{14}CH{=}CH—$. ". In certain embodiments, $L^4$ is $—(CH_2)_{1\text{-}20}CH{=}CH$-". In certain embodiments, $L^4$ is $—(CH_2)_{20\text{-}40}CH{=}CH$-". In certain embodiments, $L^4$ is $—(CH_2)_{40\text{-}60}CH{=}CH$-". In certain embodiments, $L^4$ is $—(CH_2)_{60\text{-}80}CH{=}CH$-". In certain embodiments, $L^4$ is **$—(CH_2)_{80\text{-}99}CH{=}CH$-".

In certain embodiments, $A^2$ is bromide. In certain embodiments, $A^2$ is chloride. In certain embodiments, $A^2$ is iodide. In certain embodiments, $A^2$ is triflate. In certain embodiments, $A^2$ is acetate. In certain embodiments, $A^2$ is p-toluenesulfonate.

In certain embodiments, the compound of Formula (IIa) is:

(IIa)

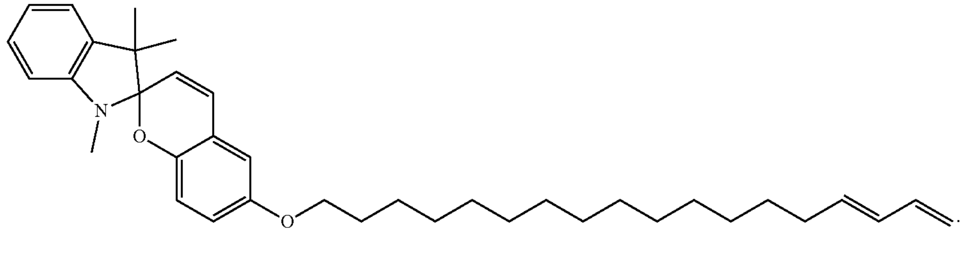

In certain embodiments, the compound of Formula (IIb) is:

(IIb)

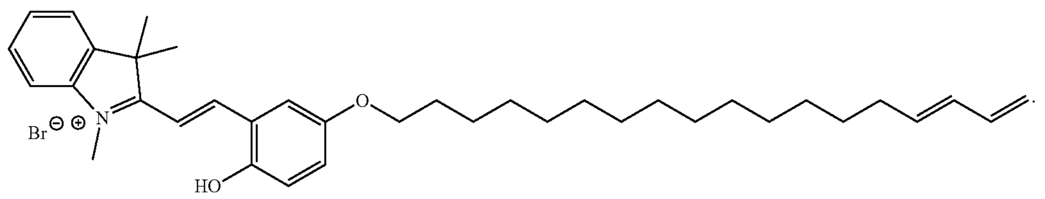

In certain embodiments, the compound of Formula (IIa) and/or Formula (IIb) comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIa) and/or Formula (IIb) comprises less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIa) and/or Formula (IIb) comprises more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIa) comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIa) comprises less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIa) comprises more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (IIb) comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIb) comprises less than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %). In certain embodiments, the compound of Formula (IIb) comprises more than about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or about 5.0% of the composition by weight (w/w %).

In certain embodiments, the compound of Formula (I) and the compound of Formula (IIa) and/or Formula (IIb) have a ratio of about 80:1, 81:1, 82:1, 83:1, 84:1, 85:1, 86:1, 87:1, 88:1, 89:1 90:1 by weight. In certain embodiments, the compound of Formula (I) and the compound of Formula (IIa) and/or Formula (IIb) have a ratio of less than about 80:1, 81:1, 82:1, 83:1, 84:1, 85:1, 86:1, 87:1, 88:1, 89:1 90:1 by weight. In certain embodiments, the compound of Formula (I) and the compound of Formula (IIa) and/or Formula (IIb) have a ratio of more than about 80:1, 81:1, 82:1, 83:1, 84:1, 85:1, 86:1, 87:1, 88:1, 89:1 90:1 by weight.

In certain embodiments, the compound of Formula (I) and the compound of Formula (IIa) and/or Formula (IIb) have a ratio of about 86.5:1 by weight (w/w %). In certain embodiments, the compound of Formula (I) and the compound of Formula (IIa) and/or Formula (IIb) have a ratio less than of about 86.5:1 by weight (w/w %). In certain embodiments, the compound of Formula (I) and the compound of Formula (IIa) and/or Formula (IIb) have a ratio of more than about 86.5:1 by weight (w/w %).

In certain embodiments, the compound of Formula (I) and the compound of Formula (IIa) have a ratio of about 86.5:1 by weight (w/w %). In certain embodiments, the compound of Formula (I) and the compound of Formula (IIa) have a ratio less than of about 86.5:1 by weight (w/w %). In certain embodiments, the compound of Formula (I) and the compound of Formula (IIa) have a ratio of more than about 86.5:1 by weight (w/w %).

In certain embodiments, the compound of Formula (I) and the compound of Formula (IIb) have a ratio of about 86.5:1 by weight (w/w %). In certain embodiments, the compound of Formula (I) and the compound of Formula (IIb) have a ratio less than of about 86.5:1 by weight (w/w %). In certain embodiments, the compound of Formula (I) and the compound of Formula (IIb) have a ratio of more than about 86.5:1 by weight (w/w %).

In certain embodiments, the polymer composition comprises the reaction product of two or more compounds selected from the group consisting of the compound of Formula (I), the compound of Formula (IIa), and/or the compound of Formula (IIb), wherein each of the following apply:

(a) a covalent bond is formed between at least one alkene of a first compound of Formula (I) and at least one alkene of a second compound of Formula (I);

(b) a covalent bond is formed between at least one alkene of the compound of Formula (I) and at least one alkene of the compound of Formula (IIa) or the compound of Formula (IIb).

In certain embodiments, the polymer comprises a plurality of nanoholes. In certain embodiments, the nanoholes have a diameter of about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm. In certain embodiments, the nanoholes have a diameter of less than about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm. In certain embodiments, the nanoholes have a diameter of more than about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm.

In certain embodiments, the polymer comprises an aqueous lyotropic liquid crystal (LLC) phase.

In certain embodiments, the LLC phase comprises a gyroid bicontinuous cubic (Q-phases) morphology.

In certain embodiments, polymer composition is responsive to external stimuli.

In certain embodiments, the external stimuli is at least one selected from the group consisting of pH changes, UV irradiation, and/or $Pb^{2+}$ ions.

In certain embodiments, the response is selected from the group consisting of changes in color and changes in unit cell dimensions.

In certain embodiments, Q-phase polymer network materials described herein that contain the compound of Formula (IIa), the compound of Formula (IIb), or a mixture of compounds of Formula (IIa) and Formula (IIb) that is/are cross-linked with the compound of Formula (I) exhibit surprising and unexpected properties. In certain embodiments, the Q-phase networked material described herein unexpectedly has at least one additional functional property that is distinct from or is in addition to its ability to perform molecular size separations and/or charge discrimination.

Without being bound by theory, the Q-phase polymer network materials described herein have unexpected properties at least because Q phases are more sensitive than lower-dimensionality LLC phases and require specific amphiphile structural motifs and precise amphiphile/solvent compositions in order to achieve a phase, and thus functional groups or structures that have properties aside from molecular size separation and/or charge discrimination could be expected to disrupt the Q-phase.

In certain embodiments, the Q-phased polymer networked materials described herein surprisingly respond (within minutes) to changes in multiple external stimuli with retention of its phase architecture but with internal physical changes that allow it to be used in potential gated transport or in responsive/sensing uptake applications.

Methods

In another aspect, the present disclosure provides a method of preparing a polymer composition of the present disclosure, the method comprising:

(a) contacting the compound of Formula (I) and a photoinitiator in the presence of a solvent to provide a gyroid mesophase gel; and (b) irradiating the gyroid mesophase gel with UV light.

In certain embodiments, the photoinitiator is selected from the group consisting of 2,2-dimethoxy-2-phenylacetophenone (DMPA) and 2-hydroxy-4'-(2-hydroxyethoxy)-2-methylpropiophenone (HHMP).

In certain embodiments, the solvent is water.

In certain embodiments, the compound of Formula (I), photoinitiator, and solvent have a ratio of about 87.5:11.5:1, 88:11:1, and 84:11:1 by weight (w/w %).

In another aspect, the present disclosure provides a method of preparing a polymer composition of the present disclosure, the method comprising:

(a) contacting the compound of Formula (I), the compound of Formula (IIa) and/or Formula (IIb), and a photoinitiator in the presence of a solvent to provide a gyroid mesophase gel; and (b) irradiating the gyroid mesophase gel with UV light.

In certain embodiments, the photoinitiator is selected from the group consisting of 2,2-dimethoxy-2-phenylacetophenone (DMPA) and 2-hydroxy-4'-(2-hydroxyethoxy)-2-methylpropiophenone (HHMP).

In certain embodiments, the solvent is water.

In certain embodiments, the compound of Formula (I); the compound of Formula (IIa), Formula (IIb), or a mixture thereof; photoinitator; and solvent have a ratio of about 86.5:1:11.5:1 by weight. In certain embodiments, the compound of Formula (I); the compound of Formula (IIa), Formula (IIb), or a mixture thereof; photoinitiator; and solvent have a ratio of less than about 86.5:1:11.5:1 by weight. In certain embodiments, the compound of Formula (I); the compound of Formula (IIa), Formula (IIb), or a mixture thereof; photoinitiator; and solvent have a ratio of more than about 86.5:1:11.5:1 by weight.

In another aspect, the present disclosure provides a method of separating analytes in a solution by size, the method comprising contacting a solution comprising one or more analytes and the polymer composition of the present disclosure. In certain embodiments, the method of separating analytes comprises contacting passing an influent solution comprising one or more analytes through the polymer composition of the present disclosure, thereby generating an effluent. In certain embodiments, the effluent comprises analytes with a diameter exceeding about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm. In certain embodiments, the analytes having a diameter of about 0.5, 0.6, 0.7, 0.8, 0.9, 1.1, 1.2, 1.3, 1.4, 1.5, 1.6, 1.7, 1.8, 1.9, 2.0, 2.1, 2.2, 2.3, 2.4, or about 2.5 nm are at least partially removed from the influent (i.e., absent and/or reduced abundance in the effluent).

In another aspect, the present disclosure provides a method of at least partially sequestering $Pb^{2+}$ ions in a solution, the method comprising contacting a solution comprising $Pb^{2+}$ ions and the polymer composition of the present disclosure. In certain embodiments, the polymer composition of the present disclosure comprises a polymerized product of at least one of the compound of Formula (IIa) and the compound of Formula (IIb).

In another aspect, the present disclosure provides a method of detecting an acidic pH, the method comprising observing at least one selected from the group consisting of a color change and a change in unit cell dimension of a polymer composition of the present disclosure upon contact with at least one selected from the group consisting of an aqueous solution and an aqueous vapor. In certain embodiments, the polymer composition of the present disclosure comprises a polymerized product of at least one of the compound of Formula (IIa) and the compound of Formula (IIb). In certain embodiments, contact with the aqueous solution and/or aqueous vapor results in a change in color and/or unit cell dimension of the polymer composition if the aqueous solution and/or aqueous vapor are acidic.

EXAMPLES

Various embodiments of the present application can be better understood by reference to the following Examples which are offered by way of illustration. The scope of the present application is not limited to the Examples given herein.

Materials and Methods

Instrumentation

NMR spectra were obtained using a Bruker Avance-III 300 NMR spectrometer (300 MHz for $^1H$, 75 MHz for $^{13}C$). Chemical shifts are reported in parts per million relative to the solvent residual signal ($CDCl_3$, δH=7.26 ppm, δC=77.16 ppm). FTIR spectra (neat) were recorded using an Agilent Cary 630 FTIR instrument single-reflection horizontal ATR accessory with a diamond crystal. The high-resolution mass spectra were obtained on a Waters SYNAPT G2 High-Definition Mass Spectrometry System at the University of Colorado Boulder Central Analytical Mass Spectrometry Facility. Lyotropic liquid-crystalline (LLC) mixtures were homogenized, as needed, using an IEC Centra-CL2 centrifuge. Elemental analysis was performed by Galbraith Laboratories, Inc. High-resolution SAXS spectra obtained on samples in vacuo were measured using a Xenocs Xeuss 2.0 system in the Dual Source and Environmental X-ray Scattering (DEXS) Facility at the University of Pennsylvania. For this Xenocs Xeuss 2.0 system, a GeniX3D Cu source with a wavelength of λ=1.54 Å was used, with a sample-to-detector distances of 363 mm and 1210 mm. Samples were measured independently to ensure equivalent exposure to vacuum. Silver behenate was used as a standard for calibrating the SAXS sample-to-detector distance, and film samples were packed between Kapton windows. Foxtrot software was used for azimuthal integration of scattering patterns into 1-D plots of scattering intensity (I) vs. q, where q=4π sin(θ)/λ, and the scattering angle is 2θ. Lower-resolution SAXS spectra for samples under ambient conditions were measured using a Rigaku S-Max-3000 instrument configured with Cu Kα radiation source with a wavelength of λ=1.54 Å and an accessible range of scattering vectors (q) from 0.015 to 0.25 Å-1 in the Osuji group at the University of Pennsylvania. Polarized light microscopy (PLM) studies were performed at the University of Colorado Boulder using a Leica DMRXP polarizing light microscope equipped with a Q-Imaging MicroPublisher 3.3 RTV digital camera, a Linkam LTS 350 thermal stage, and a Linkam CI 94 temperature controller. Automatic temperature profiles and image captures were performed using Linkam Linksys32 software. Radical photopolymerizations at the University of Colorado Boulder were conducted using a Spectroline XX-15A 365 nm UV lamp (8.5 mW $cm^{-2}$ at the sample surface). UV light fluxes at the sample surface were measured using a Spectroline DCR-100X digital radiometer equipped with a DIX-365 UV-A sensor. Radical photopolymerizations at the University of Pennsylvania were conducted using a 100-W Sunspot SM system. The lamp emission spectrum was distributed in the wavelength range between 250-450 nm, with peak intensity at 365 nm. Light irradiation of samples for the 2SP to 2M photo-isomerization studies were performed using an OmniCure® Series 1000 mercury arc lamp with a 250-450 nm filter option (100 W output). SEM images for porous supports were captured using a FEI Quanta 600 Mark II Environmental Scanning Electron Microscope, with access provided by the Singh Center at the University of Pennsylvania. UV-visible absorption spectra were taken using a HP8452A diode array UV-Vis Spectrometer (equipped with a 1 cm quartz cuvette for solution phase measurements and a 1 cm custom-made quartz film holder for polymer film measurements) at the University of Colorado Boulder.

Materials and General Procedures

Chromium(VI) oxide, pyridine, tert-butyllithium (1.6 M in pentane), hydrogen bromide (48 wt. % in $H_2O$), borane-tetrahydrofuran complex solution (1.0 M in THF), ω-pentadecalactone (98%), 2,2-dimethoxy-2-phenylacetophenone (99%), sulfuric acid, N-3-(dimethylamino)propylmethacrylamide, triethanolamine (98%), 3,5-di-tert-4-butylhydroxytoluene, 1-bromohexadecane (97%), anhydrous N,N-dimethylformamide (99.8%), and Florisil® (<200 mesh) were purchased from Sigma-Aldrich and used as received unless otherwise specified. N,N,N',N',-Tetramethylethylenediamine (98%), allyltrimethylsilane (98%), and 2-isopropoxy-4,4,5,5-tetramethyl-1,3,2-dioxaborolane (98%) were purchased from TCI America and used as received unless otherwise specified. 1',3',3'-Trimethyl-6-hydroxyspiro(2H-1-benzopyran-2,2'-indoline) (99%) was purchased from VWR and used as received unless otherwise specified. Aluminum oxide (neutral, act. I, 50-200 μm) and silica gel (normal-phase, 200×400 mesh) were purchased from Sorbent Technologies. Celite™ 545, hydrochloric acid, anhydrous magnesium sulfate, anhydrous potassium carbonate, sodium chloride, and sodium hydroxide (all ACS Reagents) were purchased from Fisher Scientific and used as received. All reaction solvents were obtained from Sigma-Aldrich and were purified/dehydrated via vacuum distillation and then degassed by repeated freeze-pump-thaw cycles and stored under Ar. All chemical syntheses were carried out under a dry Ar atmosphere using standard Schlenk line techniques unless otherwise noted. Polyacrylonitrile (PAN) membrane supported on porous PET was purchased from Sterlitech. NMR spectra were obtained using a Bruker Avance-III 300 NMR spectrometer (300 MHz for $^1H$, 75 MHz for $^{13}C$). Chemical shifts are reported in parts per million relative to the solvent residual signal (DMSO, $\delta_H$=2.50 ppm, $\delta_C$=39.52 ppm). FTIR spectra (neat) were recorded on an Agilent Cary 630 FTIR instrument single-reflection horizontal ATR accessory with diamond crystal. Elemental analysis was performed by Galbraith Laboratories, Inc.

Other Mesophase Additives

All other materials used in mesophase formulation were purchased from Sigma-Aldrich and used as received. A cross-linker additive 1,10-decanediol dimethacrylate (DDMA) was used for a mesophase formulation discussed in FIG. 3*a* of the main manuscript. The standard radical photo-initiator used for most mesophase formulations was 2,2-dimethoxy-2-phenylacetophenone (DMPA). In certain embodiments, 2-hydroxy-4'-(2-hydroxyethoxy)-2-methylpropiophenone (HHMP) was the photo-initiator used for mesophase formulation instead of DMPA.

General Mesophase Formulation Procedure

In a 1.5-mL microcentrifuge tube, 100 μL of 2,2-dimethoxy-2-phenylacetophenone (DMPA) solution (1 wt % DMPA in ethyl acetate) were pipetted. The solvent was evaporated via vacuum, leaving ca. 1 mg DMPA initiator coated on the vial walls and base. Monomer powder (typically 87.5 mg) was measured into the vial, after which 11.5 μL of water were pipetted into the vial, for a total of 100 mg of vial contents.

The tubes at were centrifuged at 14500 rpm for ca. 1 h. After the centrifugation, the tubes were left in a 70° C. drying oven in the dark for 2 min, after which the contents of the tubes were manually mixed with a blunt needle. After these steps, the tubes were returned to the centrifuge for another ca. 1-h run at the same speed. This sequence of steps was repeated 2-4 times until a uniformly transparent, high-viscosity gyroid mesophase gel was formed in the centrifuge tubes.

TABLE 1

| Compositions of the double-gyroid mesophases | | | | |
|---|---|---|---|---|
| Sample | Monomer (wt %) | Water (wt %) | DMPA (wt %) | DDMA crosslinker (wt %) |
| 1 | 87.5 | 11.5 | 1 | 0 |
| 1b | 88 | 11 | 1 | 0 |
| 1b/DDMA | 84 | 11 | 1 | 4 |

Polymer Film Fabrication Procedure 20-50 mg of the gyroid mesophase gel was sandwiched between two clean glass slides, and then pressed until the gel spread to a sufficiently large area (typically >4 $cm^2$). On occasion a bench/shop vise was used to spread the high viscosity mesophase gel over a sufficiently large area between the glass slides.

The samples were placed in a chamber with nitrogen purge and UV-cross-linked by exposure to a beam from a 100-W Sunspot SM system. The lamp emission spectrum is distributed in the wavelength range between 250-450 nm, with the peak intensity at 365 nm. After UV exposure for 3 h, cross-linked gyroid films were obtained between the glass slides. A razor blade was used to remove sections of the polymer gyroid films from the glass substrate.

Polarized Optical Microscopy (POM)

The unpolymerized mesophase gels and the corresponding polymerized films were observed under crossed polarizers using a Zeiss Axiovert 200 M inverted microscope with a CCD camera accessory connected to a computer.

Small Angle X-Ray Scattering (SAXS)

SAXS were measured using a Xenocs Xeuss 2.0 system in the Dual Source and Environmental X-ray Scattering (DEXS) facility at the University of Pennsylvania. A GeniX3D Cu source with a wavelength of $\lambda$=1.54 Å was used, with a typical sample to detector distance of 37.5 cm providing a range of accessible scattering vectors (q) from 0.016 to 1.4 $Å^{-1}$. Silver behenate was used as a standard for calibrating the sample-to-detector distance. Both monomer gel and polymerized film samples were packed between Kapton windows. Foxtrot software was used for azimuthal integration of scattering patterns into 1-D plots of scattering intensity (I) versus q. The lattice parameter a of the double-gyroid unit cell was calculated from the q-values of the (211) peaks in the 1D plots via the relation $a=(2\pi\sqrt{6})/q$. For temperature-dependent SAXS measurements, a polymer film was placed on a Linkam heating stage (Model Number L-HFSX350). The stage was heated from 30° C. to 210° C. with a heating scan rate of 10° C./min, and X-ray spectra were obtained at every 15° C. within the temperature range.

Fourier-Transform Infrared (FTIR) Spectroscopy

FTIR spectra (neat) were recorded using an Agilent Cary 630 FTIR instrument single-reflection horizontal ATR accessory with diamond crystal.

Charged Dye Solute Adsorption Experiments

Gyroid polymer films (approximately 1 $cm^2$ in area) with weights ranging from 6 to 9 mg were immersed in 40-mL volumes of aqueous dye solutions and shaken on a laboratory vortex mixer for 72 h to encourage dye uptake. The following aq. concentrations were used for the various dyes: Methylene Blue (15 μM), Methyl Orange (15 μM), Rose Bengal (15 μM), and Reactive Red 120 (75 μM). After 72 h, the polymer films were removed from the dye solutions and photographed. The percent change in the absorbances of the dye solutions at the 0- and 72-h marks were measured from a Cary 300 UV-Vis spectrophotometer operated in transmission mode using a dual-beam configuration.

Uncharged Solute Filtration Experiments

A thick gyroid film (ca. 100 μm) was installed in a high-pressure stirred cell (HP4750 Stirred Cell). Active membrane area was ca. 2 $cm^2$ (membrane diameter of 1.6 cm). An aqueous Vitamin B12 feed solution (0.05 wt %, 370 μM) was permeated through the membrane at an applied pressure of 500 psig (35 bar). The first 1 mL of permeate was discarded, and the second 1 mL was collected for measurement. VB12 rejection was quantified by the absorbance differences measured between the feed and permeate solutions with a Cary 300 UV-Vis spectrophotometer.

Calculation of the Pore Dimensions in a Double-Gyroid $Cub_{bi}$/Q Phase Membrane Calculations of the water channel dimensions in a normal-type double-gyroid phase require estimates of lattice parameter a (obtained from SAXS), as well as volume fraction estimates for the lipid and water domains. We assume that the $Br^-$ counterions associated with monomer 1 are present in the water channels. However, it is expected that $Br^-$ ions are present near the pore walls, and further that they act as 'hard spheres' to some degree, effectively constricting the pore dimension. To estimate this effect, in the subsequent calculations we include 50% of the $Br^-$ volume fraction in the lipid volume ($\O_{mem}$) and 50% in the water channel volume.

Lipid and Water Domain Volume Fraction Calculation

TABLE 2

| Molecular weight and densities of monomer 1 components | | | |
|---|---|---|---|
| Component | MW (Da) | Wt % | Density (g/mL) |
| Lipid Part (1) | 419.72 | 84 | 0.9 (assumed) |
| $Br^-$ ion | 79.9 | 16 | 3.1 |

TABLE 3

| Volume fraction calculations for various monomer 1 mesophase compositions | | | |
|---|---|---|---|
| Mesophase | $H_I$ | $Q_I$ | L |
| a (nm) | 4.87 | 8.55 | 3.31 |
| Monomer 1 (wt %) | 70 | 88.5 | 93 |
| Water (wt %) | 30 | 11.5 | 7 |
| Monomer 1 lipid part (wt %) | 58.8 | 74.34 | 78.1 |
| Monomer 1 $Br^-$ ion (wt %) | 11.2 | 14.16 | 14.9 |
| Monomer 1 lipid part (vol %) | 66 | 83.7 | 88.0 |
| Monomer 1 $Br^-$ ion (vol %) | 3.7 | 4.6 | 4.9 |
| Water (vol %) | 30.3 | 11.7 | 7.1 |

LLC Monomer Blending/Homogenization Prior to $Q_I$ Monomer Mesophase Formation

Monomer 2 (in either the 2SP or 2M–HBr form) was added to a pre-tared 1.5-dram vial. The actual mass of 2 was recorded, and the vial containing 2 was tared. The required amount of 1 was calculated and then added to the vial. The mass of 1 was recorded, and the final weight percentages were calculated for 1 and 2. The vial was then sealed and centrifuged at 4000 rpm for 10 min or until most of the solids were on the bottom of the vial. The resulting powder was then hand-mixed in air with a microspatula until homogeneous. The vial was sealed under an inert Ar atmosphere and allowed to equilibrate in the refrigerator (12° C.) overnight prior to use.

Preparation and Phase Identification of Gyroid-Type QI-Phase Blends of Monomers 1+2

Radical photo-initiator 2,2-dimethoxy-2-phenylacetophenone (DMPA) (0.50 mg) was added to a pre-tared Eppendorf tube. A 10-μL gastight syringe was conditioned/cleaned first with acetone, then with DI water. DI water (5.75 mg) was then injected into the Eppendorf tube. The homogenized blend of monomers 1+2 (in either the 2SP or 2M–HBr form) (43.71 mg, prepared as described elsewhere herein) was carefully added to the tared Eppendorf tube, and the final mass of the monomer blend was recorded. The final weight percentages were calculated to confirm that approximately a 1.0 DMPA/11.5 DI $H_2O$/87.5 monomers (1+1.0 wt % 2) blend (w/w/w) was achieved. The Eppendorf tube was sealed and centrifuged at 4000 rpm for 30 min, and the mixture was then hand-mixed with a blunt needle making sure to not scrape the sides of the tube. The Eppendorf tube was then sealed and centrifuged at 4000 rpm for 1 h or until homogeneous. Formation of a Q phase by the resulting (1+2)/water/DMPA mixture at RT (22° C.) was identified qualitatively via PLM analysis (i.e., observance of a black optical texture under cross polarizers) and quantitatively via SAXS analysis (i.e., observance of principal diffraction peaks in the ratio $1/\sqrt{6}:1/\sqrt{8}$ indicative of Q and/or gyroid LLC phases). In addition, the formed monomer mesophase was very viscous and completely optically transparent under normal light, both of which are also characteristic of Q LLC phases. Since the major monomer in this mixture (1) was found to form a gyroid-type $Q_I$ phase with added water and DMPA under similar conditions via partial phase diagram elucidation/structure characterization, it can be assumed that the same type of Q phase is formed upon blending-in a small amount of monomer 2 (i.e., 0.5-1.2 wt % of 2 relative to 1). Unfortunately, preliminary phase diagram elucidation of this (1+2)/water/DMPA system did not show the formation of a L phase. The presence of a central L phase would be needed to directly assign a Type I (normal) or II (inverted) phase configuration to the observed gyroid-type Q phase, depending on whether the Q phase appears on the water-excessive or water-deficient side of the L phase.

Fabrication of Bulk Gyroid Films of Cross-Linked (1+2)

Figure 16:
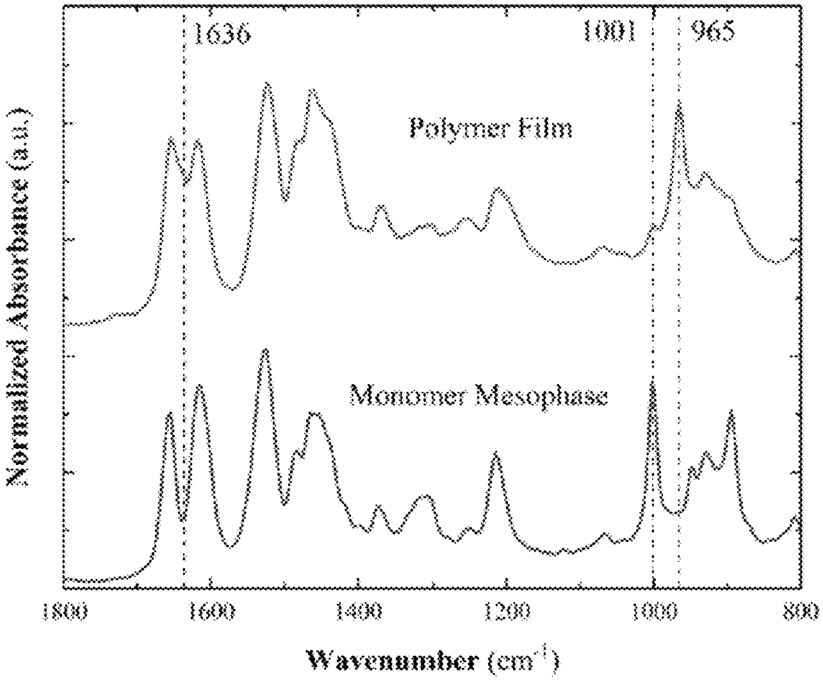
FIG. 16 provides a graph depicting a representative FT-IR spectra showing that the polymerizable 1,3-diene tails on 1 and 2 exhibit near-quantitative conversion (i.e., disappearance of band at 1001 $cm^{-1}$ and appearance of a new band at 965 $cm^{-1}$) and UV photo-initiated radical polymerization. The relative increase in intensity of the 1636 $cm^{-1}$ band indicates good conversion of the methacrylamide polymerizable group on 1.

The gyroid-type $Q_I$-phase monomer mixture (prepared as described above) was sandwiched between two pieces of clean Mylar film, placed between two clamped fused silica plates. The sample was then placed in a chamber with nitrogen purge and then irradiated with 365 nm light for 3 h at RT (22° C.). After irradiation, a clean razor blade was then used to carefully remove the bulk film from the sandwiched Mylar sheets. FT-IR spectroscopy confirmed the near complete conversion of the polymerizable groups (FIG. 16). Retention of the $Q_I$ phase in the resulting cross-linked polymer film was confirmed qualitatively via PLM and quantitatively via SAXS analysis as described in the previous section. (Note: Although both 2SP or 2M–HBr could be blended with 1 to form a stable gyroid phase, the coloration of the resulting cross-linked $Q_I$ film indicated that the dominant dopant form was 2SP instead of 2M–HBr. The shift of 2M–HBr to 2SP during the film fabrication process was likely a result of the water used for mesophase formation diluting the acid previously used to promote the 2M–HBr state).

Probing the Thermal Stability of Bulk Gyroid Films of Cross-Linked (1+2)

Figure 17:
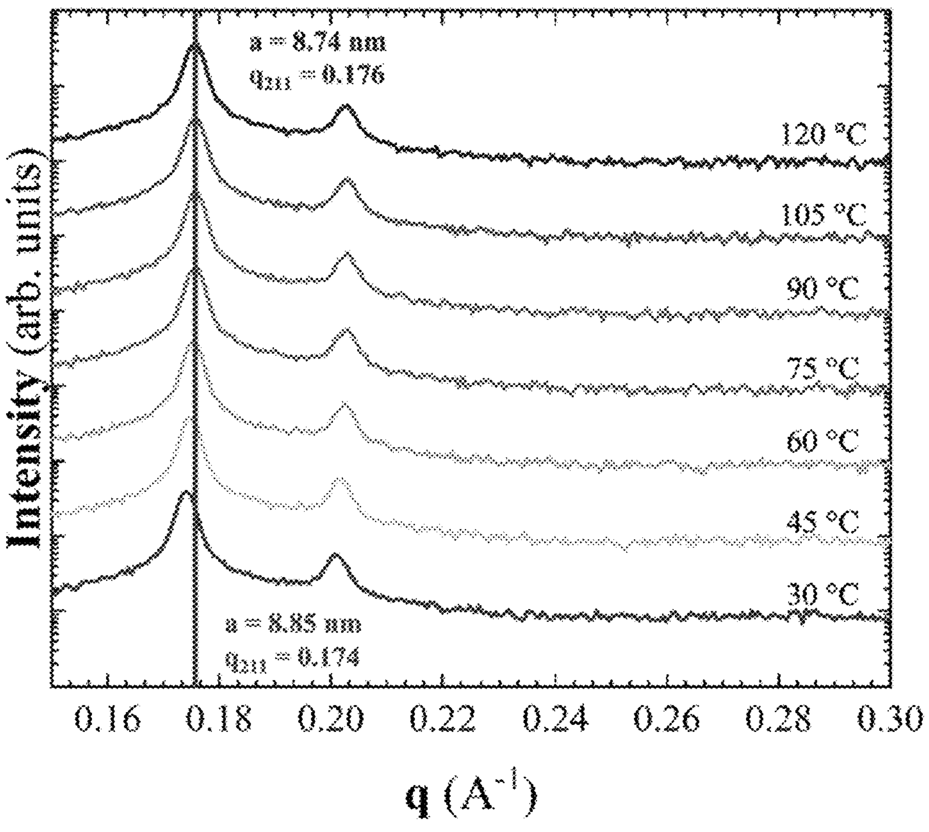
FIG. 17 provides SAXS plots showing the stability of the gyroid nanostructure in a piece of bulk gyroid film of cross-linked (1+2) at elevated temperatures. The slight shift in a at higher temperatures is attributed to dehydration of the polymer film.

For temperature-dependent SAXS measurements, a cross-linked bulk gyroid film of (1+2) were prepared as described above and then placed on a Linkam heating stage (Model Number L-HFSX350). The stage was heated from 30° C. to 120° C. with a heating scan rate of 3° C./min, 15 min equilibration/annealing time upon reaching the set temperature, followed by a 15-min SAXS capture time. SAXS spectra were obtained of the film sample at every 15° C. within the temperature range. FIG. 17 shows the SAXS spectra of these heat-treated films, indicating that the gyroid structure is effectively unchanged and stable up to 120° C. The slight shift in a value at higher temperatures is attributed to slight dehydration of the polymer film.

Probing the Acid Sensitivity and Response of Bulk Gyroid Films of Cross-Linked (1+2)

Bulk cross-linked gyroid $Q_I$ films of (1+2) (prepared as described elsewhere herein) were cut into ca. 1.0 mg strips and placed into 2.5 mL of DI water with 0.5-200 μL of 0.422 M aq. HBr added to the solution. The samples were then vortexed at 300 rpm for 12-24 h. The polymer film was gently removed from the vial and dried with a KimWipe for SAXS analysis.

Procedure for Determining Lack of Monomer Leaching and Reversibility of Spiropyran to Protonated-Merocyanine Conversion in Bulk Gyroid Films of Cross-linked (1+2)

Figure 20:
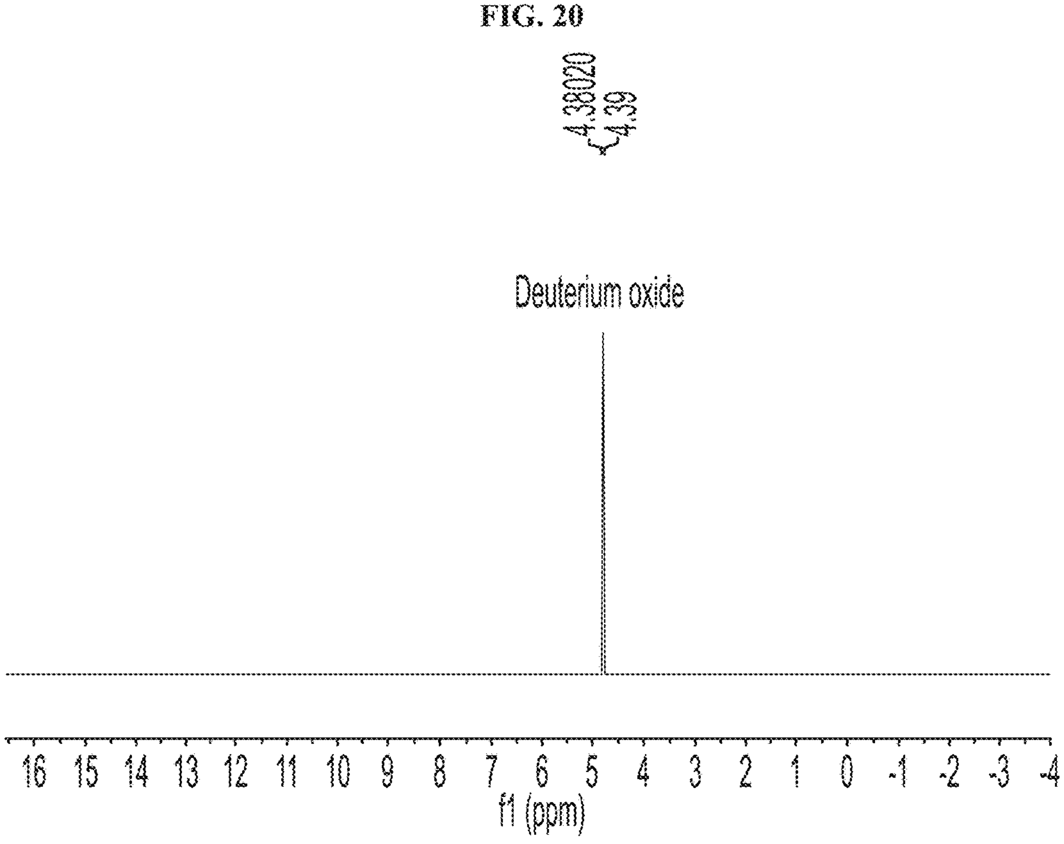
FIG. 20 provides a $^1H$ NMR spectrum of the $D_2O$ supernatant after a cross-linked $Q_I$ blend of (1+1.0 wt % 2SP) that was soaked in $D_2O$ for 24 h at RT to probe for any leaching of unreacted 1 or 2SP from the film.

To determine that no monomer 2 was leaching from the polymerized film, a previously acid-treated $Q_I$ polymer film was suspended in deuterated water (pH=ca. 5) and vortexed at 150 rpm for 24 h. An aliquot of the solution was taken and $^1H$ NMR analysis of it suggested no leaching of either unreacted 1 or 2 from the polymer film had occurred (FIG. 20). Interestingly, after removing the $Q_I$ polymer film from the $D_2O$, its appearance had reverted to its pre-acid-treated state (i.e., the uncharged spiropyran (SP) form). The same film was then suspended in water, the solution was acidified to pH ca. 0 with 0.422 M aq. HBr, and vortexed at 150 rpm for 24 h. The aqueous solution was decanted, and the film was removed and dried with a KimWipe. The appearance of the film had once again returned to its vibrant-orange HBr protonated-merocyanine state (2M–HBr), indicating that the spiropyran-merocyanine conversion is reversible when the films are suspended in solution.

Gyroid-Phase Network Pore Diameter Calculations

Due to the monomer leaching experiments showing no loss of material upon swelling, the spiropyran-based monomer dopant was assumed to be part of the cross-linked film and was counted as part of the occupied volume fraction of the unit cell. The gyroid pore diameter calculations that follow are derived from previously published procedures. Hexagonal and lamellar phase boundaries of monomer blends of (1+2) are assumed to be identical to neat monomer 1. An additional assumption of note is that the gyroid is of a consistent shape regardless of small deviations in mass from sample-to-sample. Mass percentages used in samples observed in the study (N=12) were shown as (87.5±0.5) wt % monomer blend.

To calculate the pore size of the double gyroid network, the molecular volume of the material was first calculated using the molecular weight of the organic portion of the cross-linkable surfactant, the density of the material, and Avogadro's number. Note that this is a 0.3% change from the case of pure monomer 1, which is 0.77 $nm^3$. From this point on, all lattice parameters are considered constants unless otherwise noted.

$$\text{Acidified} \rightarrow v = \frac{MW}{\rho N_{avo}} = \frac{(0.01(542.83) + 0.99(419.72))}{\rho N_{avo}} = 0.777\ \text{nm}^3 \quad \text{(Eq. 1)}$$

-continued $$\text{Neutral} \rightarrow v = \frac{MW}{\rho N_{avo}} = \frac{(0.01(541.83) + 0.99(419.72))}{\rho N_{avo}} = 0.777\ \text{nm}^3 \quad \text{(Eq. 2)}$$

After the calculation of the volume fraction, the value of the cross-section area of the molecule is calculated from the lamellar phase lattice parameter and the volume fraction of that lamellar phase (a=3.31 nm, φ=0.9045).

$$A_n = \frac{2v}{a_{lamellar}\phi_{mem}} = 0.5191\ \text{nm}^2 \quad \text{(Eq. 3)}$$

The radius of the hexagonal cylinders was calculated by the lattice parameter (a=4.87 nm, φ=0.6785).

$$r = \sqrt{\frac{\sqrt{3}\,\phi_{mem}a_{hex}^2}{2\pi}} = 2.106\ \text{nm} \quad \text{(Eq. 4)}$$

The estimation of the surfactant-water interface is predicted as the ratio of the molecular volume of the radius of the hexagonal cylinders.

$$A_{interface} = \frac{2v}{r} = 0.7379\ \text{nm}^2 \quad \text{(Eq. 5)}$$

After this, a constant molecular volume within the neutral surface area is assumed. This corresponds to the lipid bilayer, otherwise seen as the diene tails of the three blend materials. It is estimated as the ratio of the lamellar and hexagonal cross-sectional areas multiplied by the molecular volume.

-continued $$\left[\frac{a_{gyroid}^3 - 2A_0a_{gyroid}^2 z\left(1 + \frac{2\pi\chi}{3A_0a_{gyroid}^2}z^2\right)}{v_n}\right]$$

Figure 12:
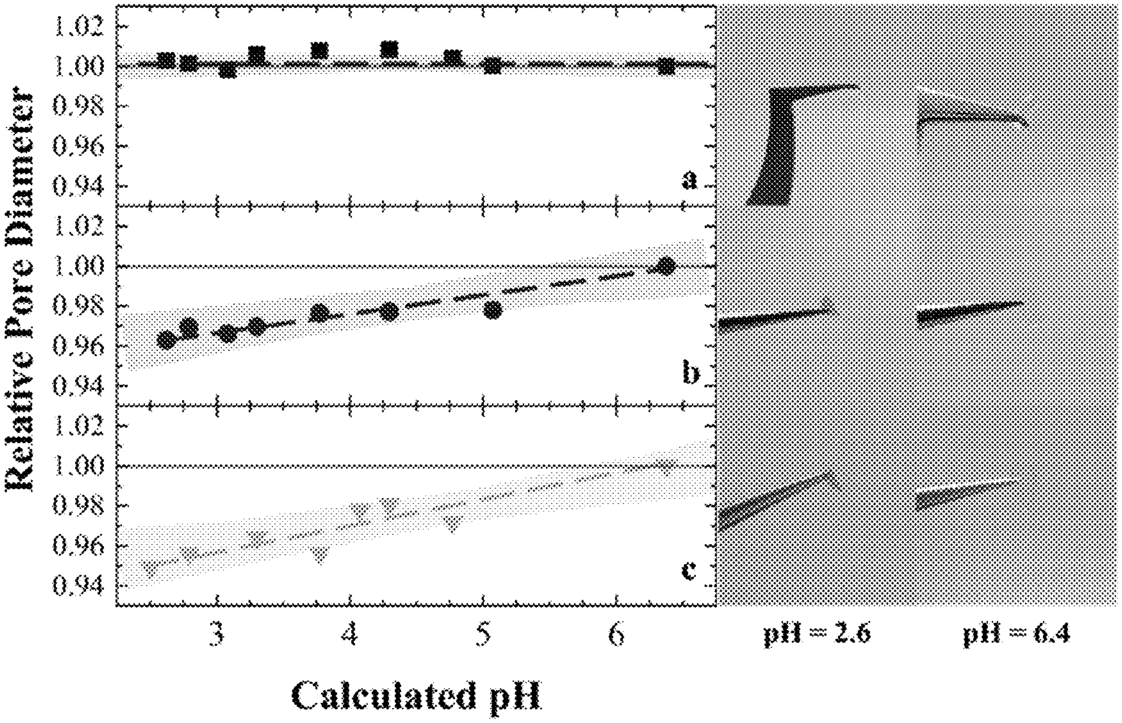
FIG. 12 provides a response plot depicting the change in calculated relative pore diameter (based on observed unit cell lattice parameter changes) as a function of calculated pH, and corresponding photos of films exposed to low pH (ca. 2.6) and neutral pH (ca. 6.4) for: (a) an undoped gyroid polymer film of 1; (b) a gyroid polymer film with 0.8 wt % 2; and (c) a gyroid polymer film with 1.2 wt % 2. Shaded areas in the plot represent the 95% confidence band. pH was calculated through volumetric addition of 0.422 M aq. HBr, with an instrumental random error of ±0.05 μL. Pore diameter calculations are described elsewhere herein. Photos are of different pieces of the same original film exposed to various concentrations of acid.

The standard error of the slope was then calculated for each plot shown in FIG. 12. For undoped gyroid films, the standard error of the slope was: $1.07\times10^{-3}$; for films with 0.8 wt % 2, the standard error of the slope was: $1.15\times10^{-3}$; for films with 1.2 wt % 2, the standard error of the slope was: $2.15\times10^{-3}$.

Procedure for Measuring Water Vapor Transport Rate Through a Bulk Gyroid Film of Cross-Linked (1+2) as a Function of Liquid Water Reservoir pH Film samples were pinned to the cap of a 2.5-mL scintillation vial with the cap inset removed. The cap was screwed back on, with cutout of the inset serving to seal the film without damaging the film. If a good seal was not obtained by this pinning method, epoxy was used to further fill in the gaps of the vial. The vials were placed in a desiccator with Drierite® and sealed for a period of approximately 2 weeks at room temperature (RT) (22° C.), with mass measurements occurring every 24 h. Colorimetric and mass-loss changes were on the order of 24-96 h to reach steady-state. Each day, the instantaneous mass loss was recorded through the vials, and the desiccator was sealed again. Each film thickness was measured using a digital micrometer, and the instantaneous mass transport rates were calculated and compared against the rate for an open vial of the same solvent. Films were checked using PLM through 45° polarized light for excess birefringence indicative of a pinhole leak. Leaking samples, when corrected for area of vapor diffusion, showed vapor diffusion rates statistically similar to those of open cells.

Example 1: Monomer Synthesis (E)-N-(3-methacrylamidopropyl)-N,N-dimethyloctadeca-15,17-dien-1-aminium bromide (Monomer 1)

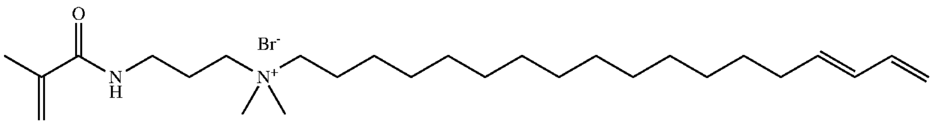 [SMILES: C=C/C=C/CCCCCCCCCCCCCC[N+](C)(C)CCCNC(=O)C(=C)C ; [Br-]]

$$v_n = v\left(\frac{A_n}{A_{interface}}\right)^2 = 0.3845\ \text{nm}^3 \quad \text{(Eq. 6)}$$

Next, the pore size of the laid gyroid structure is minimized, which is consistent with the space group observed in the gels described herein. The constants of the Ia3d space group are ($A_0$=3.091, χ=−8). A minimization operation is then performed to find the radius of the pore channel, and this is doubled to obtain the pore diameter. The calculated diameter is then compared across the acidification conditions to yield the plots shown in FIG. 12.

$$\frac{2A_0a_{gyroid}^2}{A_n}\left(1 + \frac{2\pi\chi}{A_0a_{gyroid}^2}z^2\right) = \quad \text{(Eq. 7)}$$

18-Bromooctadeca-1,3-diene (1.9979 g, 6.0658 mmol, 1.0000 equiv.), N-3-(dimethylamino)propylmethacrylamide (1.1360 g, 6.6725 mmol, 1.1000 equiv.), and 3-4 crystals of 3,5-di-tert-4-butylhydroxytoluene were dissolved in $CH_3CN$ (10 mL) in a 25-mL amber Schlenk flask equipped with a stir bar. The solution was stirred at 70° C. for 24 h in the dark. The contents of the Schlenk flask were cooled to room temperature and precipitated from $Et_2O$ (200 mL) in a Dry Ice-acetone bath. The precipitate was filtered immediately and dried in vacuo to give monomer 1 as a white solid (2.6491 g, 87%). $^1$H NMR (300 MHz, DMSO-$d_6$): δ 8.06 (t, J=5.8 Hz, 1H), 6.39-6.20 (m, 1H), 6.11-5.96 (m, 1H), 5.79-5.65 (m, 1H), 5.67 (td, J=1.9, 1.0 Hz, 1H), 5.35 (p, J=1.6 Hz, 1H), 5.15-5.02 (m, 1H), 5.01-4.90 (m, 1H), 3.21 (ddd, J=19.0, 9.7, 4.9 Hz, 6H), 2.99 (s, 6H), 2.03 (q, 1H), 1.86 (dd, J=1.6, 0.9 Hz, 3H), 1.61 (s, 2H), 1.39-1.21 (m, 14H). $^{13}$C NMR (75 MHz, DMSO-$d_6$): δ 167.64, 139.75, 137.23, 135.29, 130.88, 119.28, 115.09, 62.84, 50.12, 35.91, 31.88, 29.03, 28.99, 28.85, 28.60, 28.58, 28.52, 25.77, 22.46, 21.65, 18.61. FTIR (neat): 3224, 2917, 2849, 1656, 1619, 1531, 1467, 1318, 1212, 1070, 1003, 912, 803, 720 $cm^{-1}$. Calc. for $C_{27}H_{51}BrN_2O$: C, 64.91; H, 10.29; N, 5.61. Found: C, 64.68; H, 10.26; N, 5.58.

N-(3-Methacrylamidopropyl)-N,N-dimethylhexadecan-1-aminium bromide (Monomer 1b)

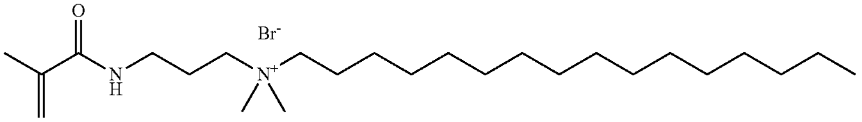 [SMILES: C=C(C)C(=O)NCCC[N+](C)(C)CCCCCCCCCCCCCCCC ; [Br-]]

1-Bromohexadecane (8.0000 g, 0.026200 mol, 1.0000 equiv.), N-3-(dimethylamino)propylmethacrylamide (4.9068 g, 0.028821 mol, 1.1000 equiv.), and 3-4 crystals of 3,5-di-tert-4-butylhydroxytoluene were dissolved in $CH_3CN$ (50 mL) in a 100-mL amber Schlenk flask equipped with a stir bar. The solution was stirred at 70° C. for 24 h in the dark. The contents of the Schlenk flask were cooled to room temperature and precipitated from $Et_2O$ (200 mL) in a Dry Ice-acetone bath. The precipitate was filtered immediately and dried in vacuo to give monomer 1b as a white solid (8.1317 g, 65%). $^1H$ NMR (300 MHz, DMSO-$d_6$): δ 8.08 (t, J=5.8 Hz, 1H), 5.69 (dd, J=1.5, 0.9 Hz, 1H), 5.35 (p, J=1.5 Hz, 1H), 3.30-3.11 (m, 6H), 3.00 (s, 6H), 1.93-1.76 (m, 4H), 1.61 (s, 2H), 1.24 (s, 25H), 0.91-0.80 (m, 3H). $^{13}C$ NMR (75 MHz, DMSO-$d_6$): δ 167.63, 139.73, 119.27, 62.84, 60.90, 50.12, 35.90, 31.27, 29.04, 28.99, 28.94, 28.80, 28.69, 28.51, 25.77, 22.43, 22.08, 21.64, 18.60, 13.94. FTIR (neat): 3378, 2918, 2850, 1653, 1612, 1530, 1465, 1334, 1220, 1067, 970, 923, 809, 720 $cm^{-1}$. Calc. for $C_{25}H_{51}BrN_2O$: C, 63.14; H, 10.81; N, 5.89.

(E)-1',3',3'-trimethyl-6-(octadeca-15,17-dien-1-yloxy)spiro[chromene-2,2'-indoline](2SP)

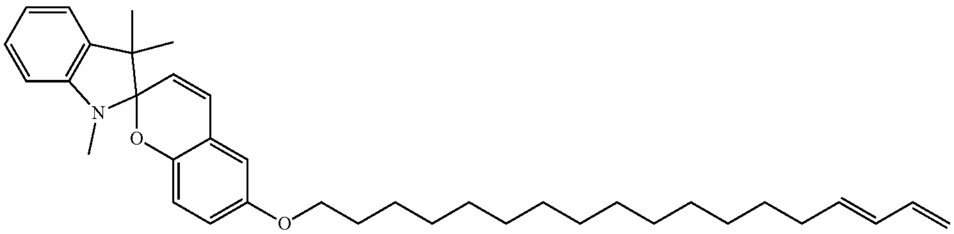 [SMILES: C=C/C=C/CCCCCCCCCCCCCCOc1ccc2c(c1)C=CC1(O2)N(C)c2ccccc2C1(C)C]

18-Bromooctadeca-1,3-diene (0.6175 g, 1.875 mmol, 1.100 equiv.), K2CO3 (1.178 g, 8.523 mmol, 5.002 equiv.) and 1',3',3'-trimethyl-6-hydroxyspiro(2H-1-benzopyran-2,2'-indoline) (0.5000 g, 1.704 mmol, 1.000 equiv.) were suspended in DMF (40 mL) in a 125-mL Schlenk flask equipped with a stir bar. The solution was stirred at 80° C. for 20 h in the dark. The contents of the Schlenk flask were cooled to RT and diluted in a mixture of EtOAc and deionized (DI) $H_2O$ (100 mL each). The organic phase was separated, and the aqueous phase was extracted with EtOAc (3x75 mL). The combined EtOAc extracts were extracted with DI $H_2O$ (2×100 mL), saturated aq. $NH_4Cl$ (2×100 mL), and brine (2×100 mL). The combined EtOAc extracts were dried over anhydrous MgSO4, filtered through a pad of celite, and concentrated by rotary evaporation to afford the product as a light-brown solid (0.8342 g, 90%). $^1H$ NMR (300 MHz, $CDCl_3$): δ=7.22-7.03 (m, 2H), 6.88-6.76 (m, 2H), 6.70-6.58 (m, 3H), 6.51 (dd, J=0.87, 7.68 Hz, 1H), 6.40-6.23 (m, 1H), 6.11-5.97 (m, 1H), 5.81-5.61 (m, 2H), 5.14-4.90 (m, 2H), 3.88 (t, J=6.57 Hz, 2H), 2.72 (s, 3H), 2.07 (q, J=7.06 Hz, 2H), 1.73 (p, 2H), 1.52-1.21 (m, 29H), 1.16 (s, 3H). $^{13}C$ NMR (75 MHz, $CDCl_3$): δ=137.52, 135.83, 130.96, 129.48, 127.68, 121.62, 120.30, 119.18, 119.12, 116.07, 115.58, 114.70, 112.37, 106.87, 77.36, 68.83, 51.74, 32.71, 29.81, 29.75, 29.65, 29.56, 29.34, 29.09, 26.22, 26.00, 20.39. FTIR ($cm^{-1}$, neat): 2915, 2848, 1610, 1487, 1461, 1252, 1185, 1021, 1001, 961, 741. UV-visible peak maxima (nm, in 1:1 (v/v) acetone/$CH_2Cl_2$): 300, 337. HRMS (m/z, ESI) [M+H]+ calcd: 542.3998; found: 542.4001. Anal. calcd for $C_{37}H_{51}NO_2$: C, 82.02, H, 9.49; N, 2.59; found: C, 81.76; H, 9.80; N, 2.53.

2-((E)-2-hydroxy-5-(((E)-octadeca-15,17-dien-1-yl)oxy)styryl)-1,3,3-trimethyl-3H-indol-1-ium bromide (2M–HBr)

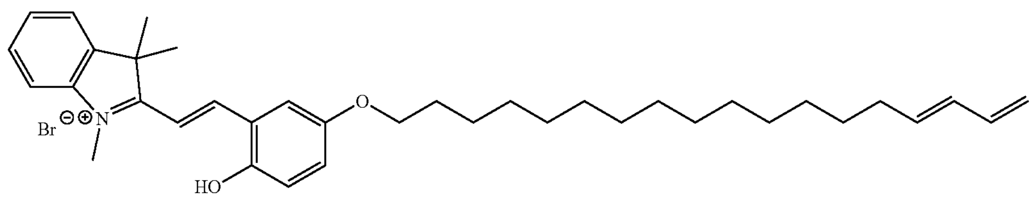 [SMILES: C=C/C=C/CCCCCCCCCCCCCCOc1ccc(O)c(/C=C/C2=[N+](C)c3ccccc3C2(C)C)c1 ; [Br-]]

Monomer 2SP (0.1072 g, 0.1979 mmol, 1.000 equiv.) was dissolved in a minimal amount of acetone. An equimolar amount of 0.422 M aq. HBr solution (0.4688 mL, 0.1978 mmol, 1.000 equiv.) was added. Upon addition of acid, the light brown solution changed to a vibrant orange-red and a precipitate was formed. $CH_2Cl_2$ was added until all solids were dissolved yielding a clear red solution. The solution was allowed to evaporate overnight at RT. The residual powder was then dried in vacuo to give 2M–HBr as a vibrant orange-red powder. Note: HBr was chosen as the strong acid used to promote the acidochromic switch of 2SP to 2M–HBr to ensure only bromide counterions were present in the samples (i.e., no anion mixtures) for the NMR and blending studies with 1. $^1$H NMR (300 MHz, DMSO-$d_6$): δ=10.64 (s, 1H), 8.48 (d, J=16.42 Hz, 1H), 7.99-7.77 (m, 2H), 7.79-7.54 (m, 4H), 7.12 (dd, J=2.96, 9.02 Hz, 1H), 6.97 (d, J=9.01 Hz, 1H), 6.44-6.20 (m, 1H), 6.12-5.93 (m, 1H), 5.81-5.63 (m, 1H), 5.18-4.85 (m, 2H), 4.10 (s, 3H), 3.99 (t, J=6.35 Hz, 2H), 2.14-1.98 (m, 2H), 1.75 (s, 8H), 1.24 (s, 24H). 13C NMR (75 MHz, DMSO-$d_6$): δ=152.01, 137.24, 135.31, 130.88, 115.10, 68.20, 51.84, 34.30, 31.89, 29.03, 28.82, 28.60, 26.03, 25.60. IR (cm$^{-1}$, neat): 3034, 2919, 2851, 1580, 1524, 1498, 1476, 1308, 1162, 1002, 898, 776. UV-visible peak maxima (nm, in 1:1 (v/v) acetone/$CH_2Cl_2$): 378, 474. HRMS (m/z, ESI) [M]+ calcd: 542.3998; found, 542.4001. Anal. calcd for $C_{37}H_{52}NO_2Br$: C, 71.36; H, 8.42; N, 2.25; found: C, 71.37; H, 8.53; N, 2.21.

Figure 5:
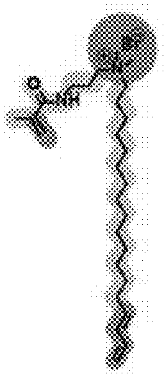
FIG. 5 shows chemical structures of cross-linkable monomer 1, non-cross-linkable monomer 1b, and commercial cross-linker DDMA, according to various embodiments.
Figure 5:
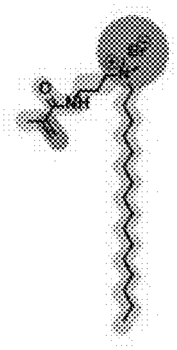
Figure 5:
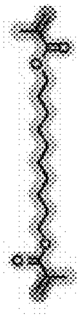

Example 2: Design and Characterization of a Single Head/Single Tail Q-Phase Polymer Monomer Monomer 1 was synthesized by reacting N-[3-(dimethylamino)propyl]methacrylamide with 18-bromooctadeca-1,3-diene in $CH_3CN$ at 70° C. in a one-step $S_N2$ reaction. After purification, the structure and purity of 1 were verified by $^1$H NMR, $^{13}$C NMR, FT-IR, and elemental analyses. The design of 1 was based on a non-cross-linkable cationic monomer with a single methacrylamide group near the head that was recently found to form a Q phase with aqueous solutions (i.e., monomer 1b, see FIG. 3A and FIG. 5). By replacing the long alkyl tail on this monomer with a polymerizable diene tail, an intrinsically cross-linkable analogue was generated. The diene tail system was chosen because of its similarity in shape and hydrophobic character to regular n-alkyl tails compared to tail systems with bulkier or more polar polymerizable moieties, thereby increasing the probability of retaining the Q phase of the original monomer. Additionally, 1 can also form other LLC mesophases such as lamellar and hexagonal.

Figure 1:
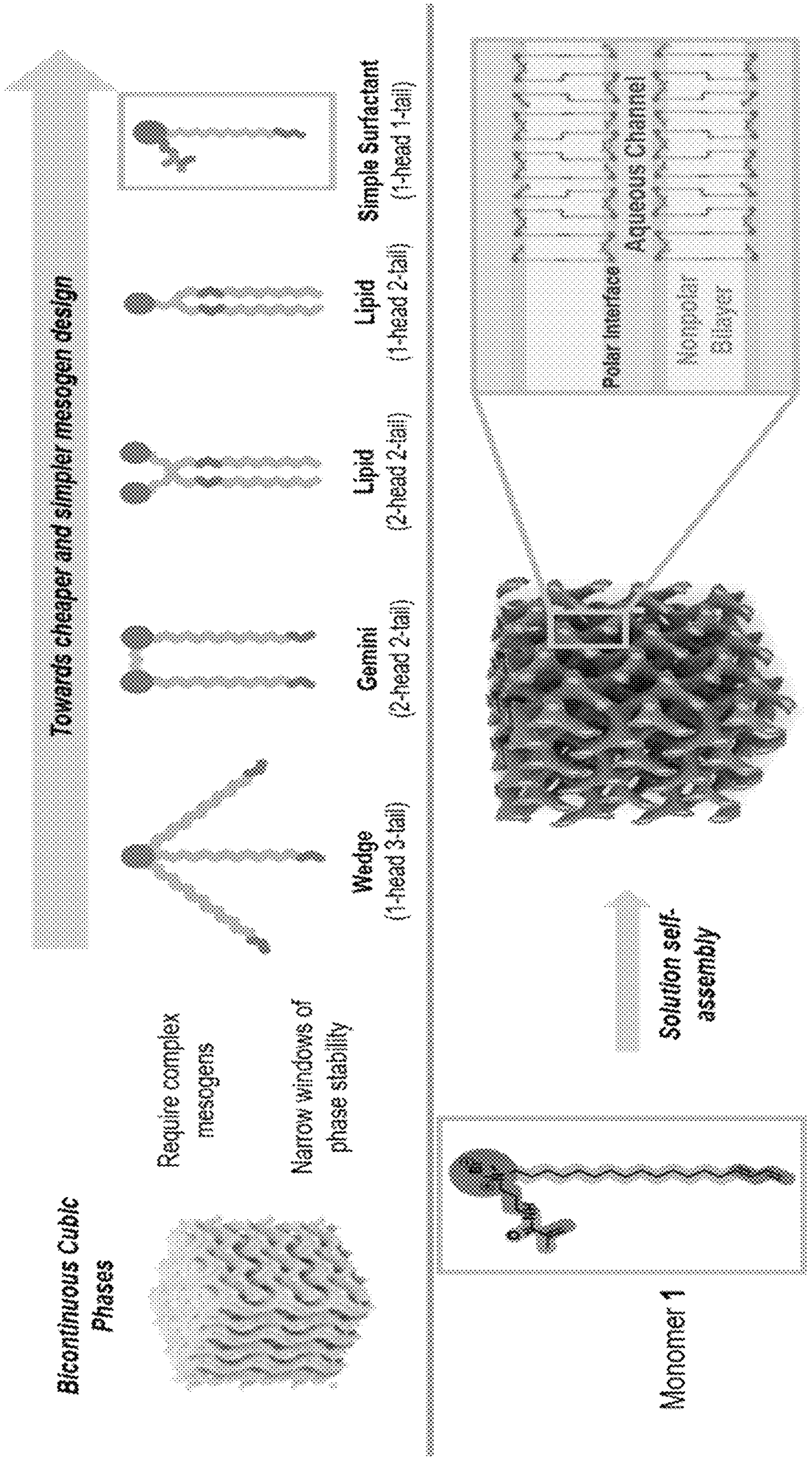
FIG. 1 provides a schematic of double-gyroid Q phase and typical cross-linkable LLC monomer architectures that form Q phases (i.e., hydrophilic headgroup, hydrophobic tail, and polymerizable group). The design of monomer 1, as well its self-assembly into a nanoporous, normal-type, double-gyroid network, are also depicted therein.
Figure 2A:
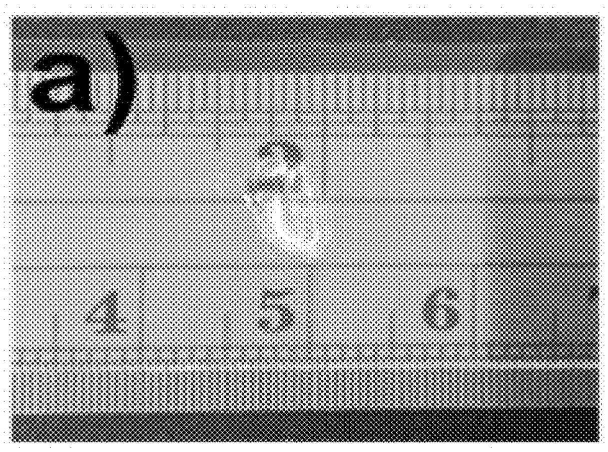
FIGS. 2A-2C provide photos of monomer gyroid mesophase of 1, water, and photo-initiator (FIG. 2A), dry polymer film of cross-linked gyroid phase of 1 (FIG. 2B), and the same polymer film of 1 after 30-min water immersion (FIG. 2C).
Figure 2B:
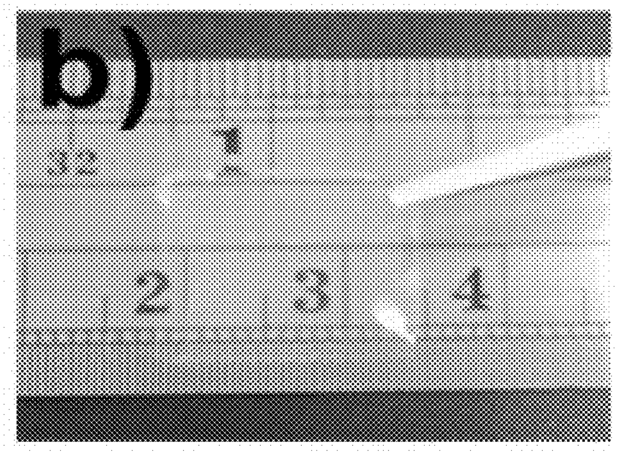
Figure 2C:
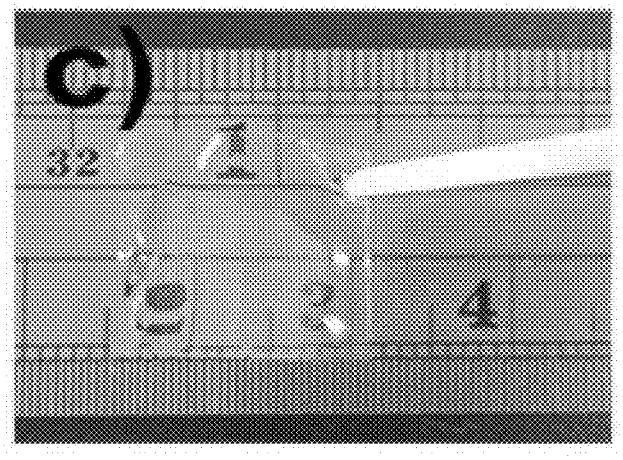
Figure 2D:
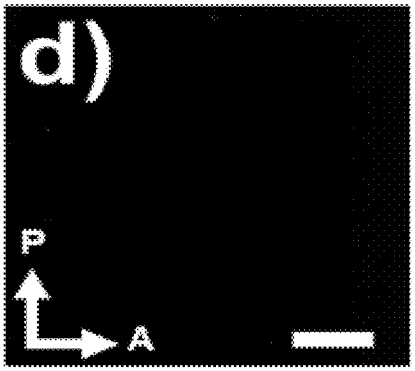
FIGS. 2D-2E provide POM micrographs of monomer mesophase (FIG. 2D) and dry polymer film observed between crossed polarizers (FIG. 2E); scale bar=100 μm.
Figure 2E:
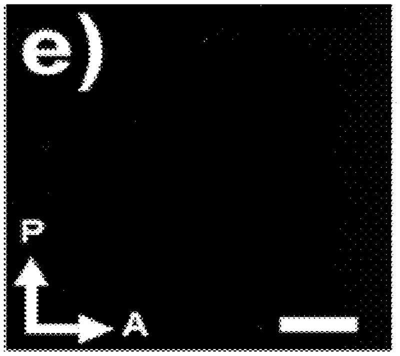

A Q phase was obtained at room temperature at a composition of 87.5/11.5/1.0 (w/w/w) monomer 1/water/2,2-dimethylpropiophenone (DMPA, a radical photo-initiator). Polymer films with retention of the Q-phase structure (typical thicknesses between 50-150 μm) were obtained by photo-cross-linking the monomer mesophase with UV light under $N_2$ purge for ca. 3 h (FIGS. 2A-2C). The monomer mesophase and the resulting polymer films exhibited dark POM images, consistent with the optically isotropic character of Q phases (FIGS. 2D-2E).

Figure 2F:
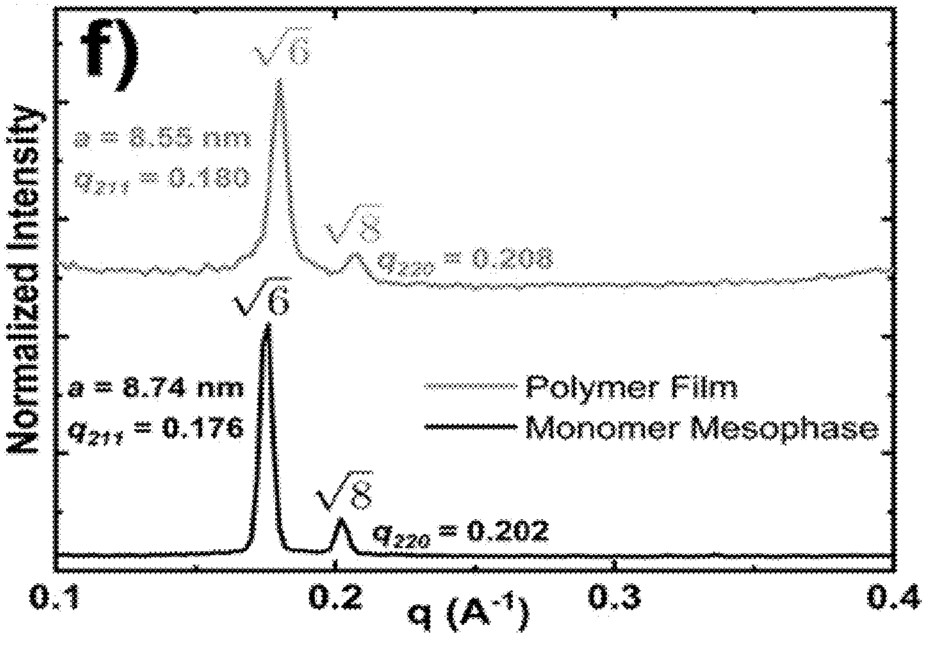
FIG. 2F provides a SAXS spectra of gyroid mesophase (bottom) and polymer (top) of 1.
Figure 6A:
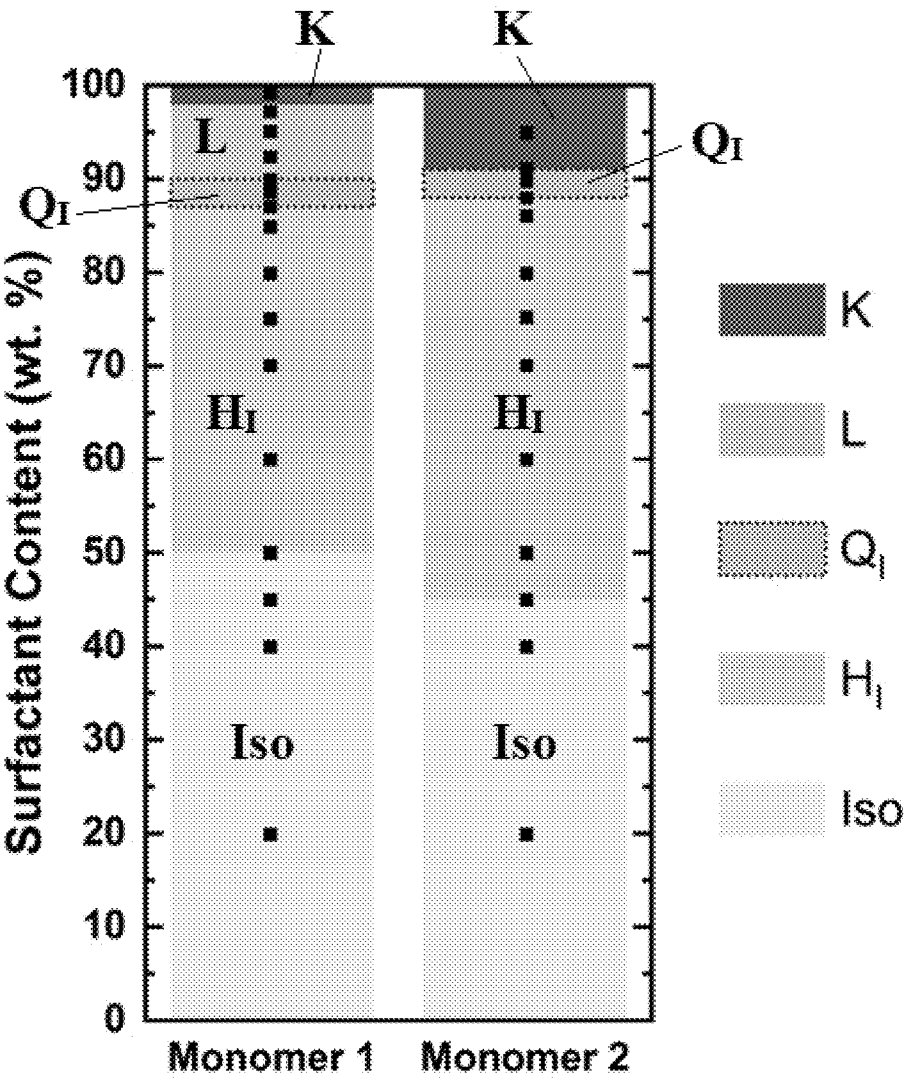
FIGS. 6A-6B show binary phase diagrams of aqueous mixtures of monomer 1 and of monomer 1b at room temperature (22-25° C.), as approximately determined from POM analysis. Typical POM textures for micellar/isotropic (Iso), normal hexagonal ($H_I$), normal bicontinuous cubic ($Q_I$), lamellar (L), and crystal phases (K) are shown. (Note: The H and Q phases observed for monomer 1+water were assigned as Type I (i.e., normal) phases based on their position on the water-excessive side of an observed central L phase. On occasion, co-existence of phases was observed at the estimated phase boundaries. Black squares indicate compositions where mesophase determination was made via POM.
Figure 6B:
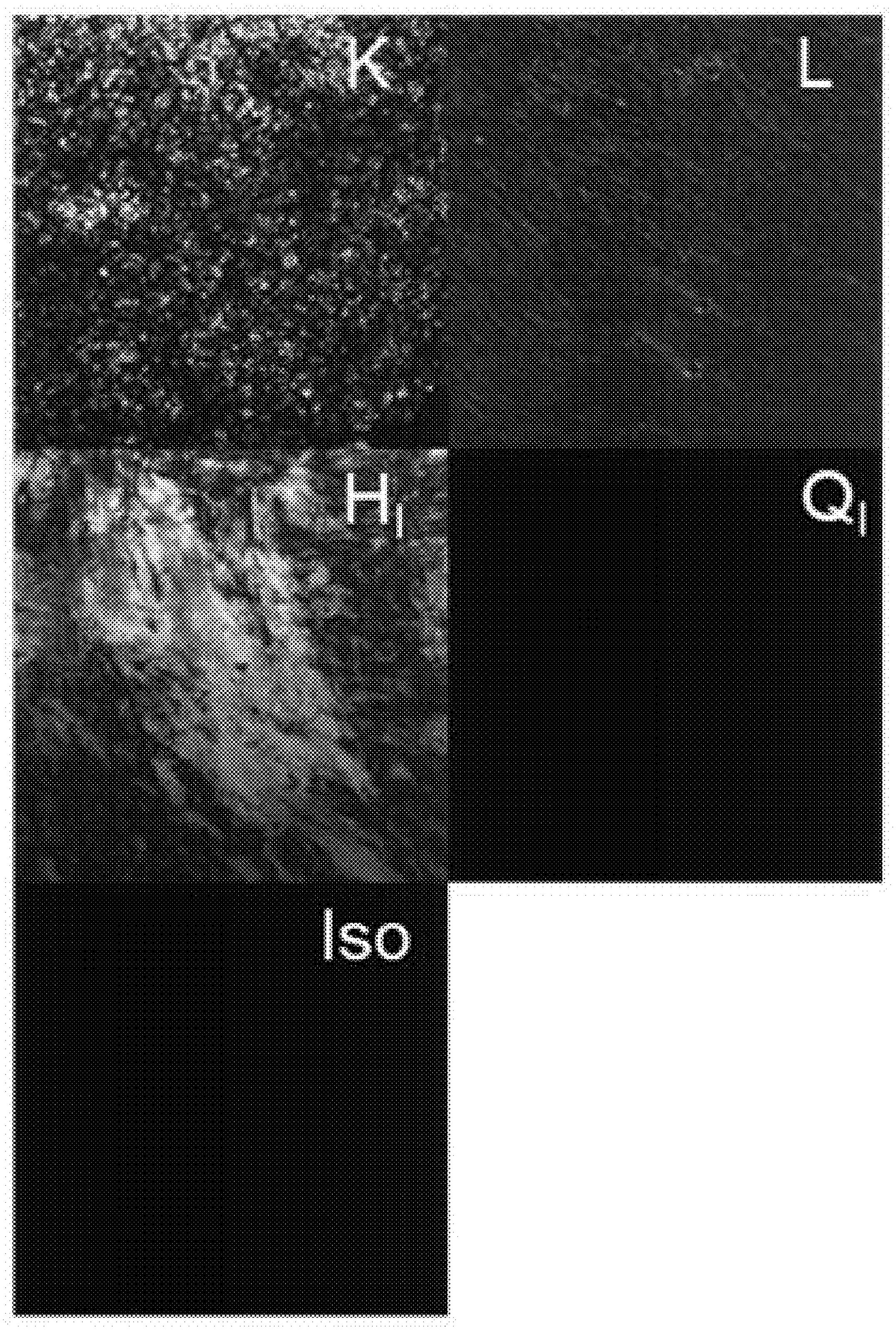
Figure 7A:
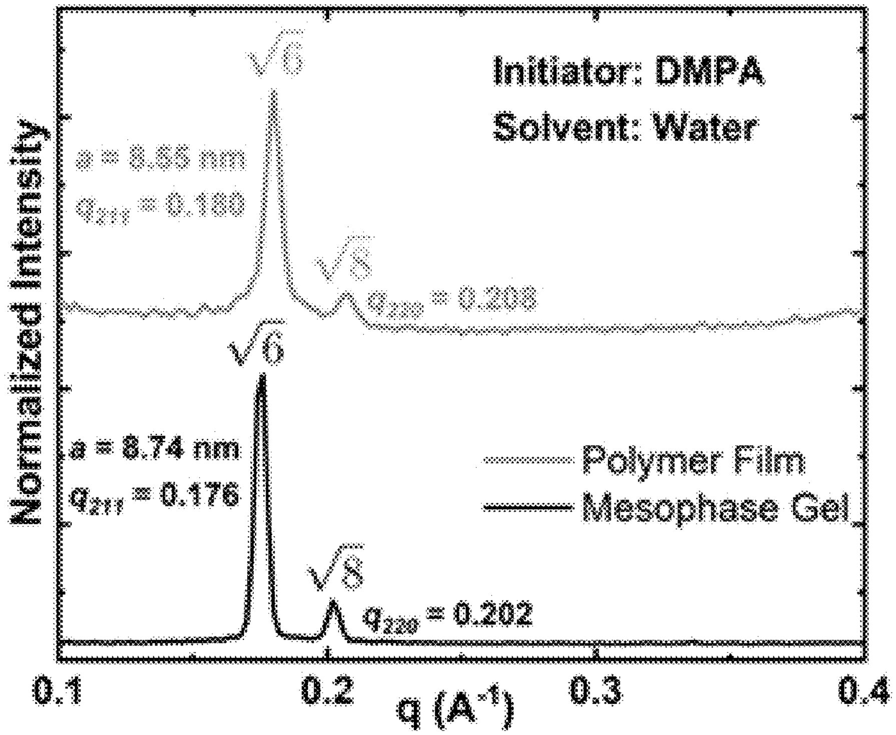
FIGS. 7A-7D show SAXS (FIGS. 7A-7B) and FTIR (FIG. 7C-7D) data for double-gyroid polymer films of 1 formulated with water (FIG. 7A and FIG. 7C) and 0.1 M aq. LiCl (FIG. 7B and FIG. 7D), with 1 wt % DMPA photoinitiator used for both solvents. For both solvents, FTIR spectra show that the diene tails exhibit quantitative conversion (disappearance of peak at 1001 $cm^{-1}$ and appearance of a peak at 965 $cm^{-1}$). The polymer made from the 0.1 M aq. LiCl-based Q phase exhibits higher conversion of the methacrylamide headgroups (peak magnitude at 1636 $cm^{-1}$) than the corresponding water-based polymer material.
Figure 7B:
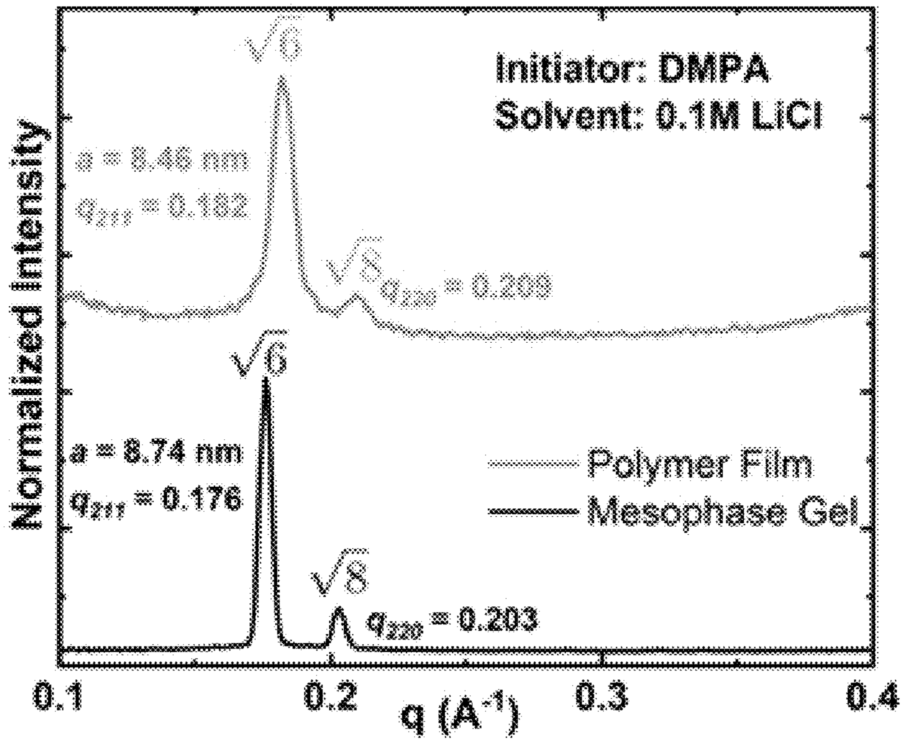
Figure 7C:
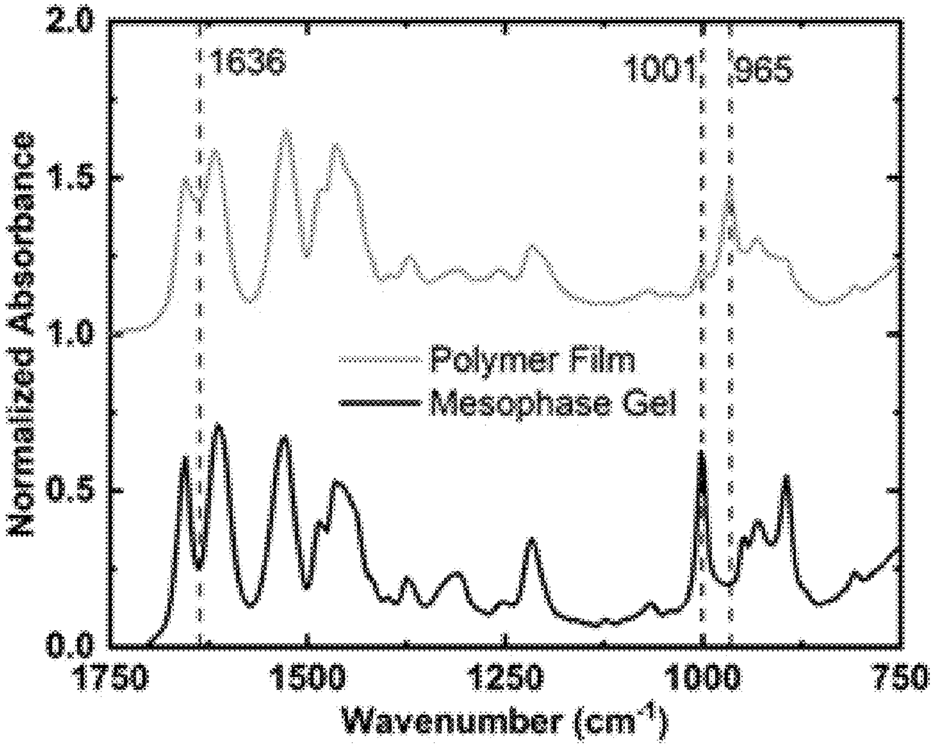
Figure 7D:
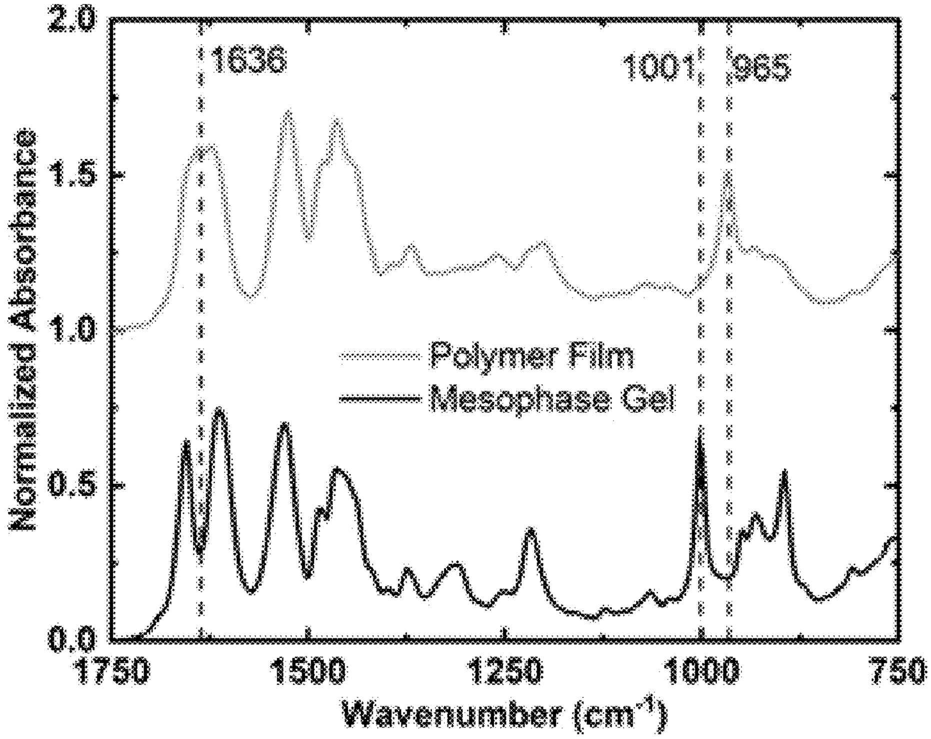
Figure 8A:
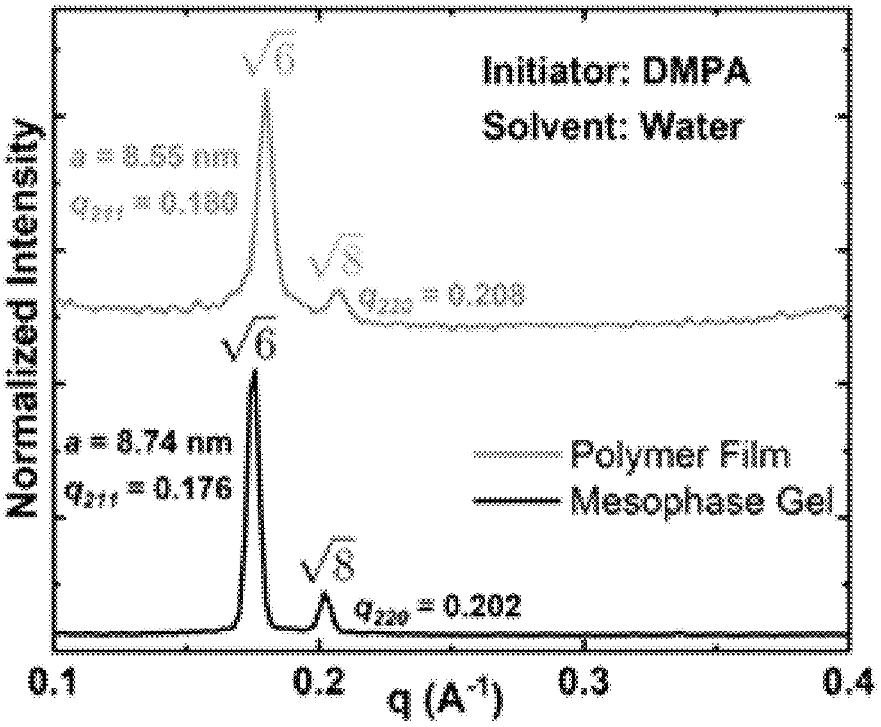
FIGS. 8A-8D shows SAXS (FIGS. 8A-8B) and FTIR data (FIGS. 8C-8D) for double-gyroid polymer films of 1 formulated with water (FIG. 8A and FIG. 8C) and separately with 0.1 M aq. LiCl (FIG. 8B and FIG. 8D), with 1 wt % HHMP photo-initiator used for both solvent systems. In both cases, the diene tail groups and methacrylamide headgroups show near-quantitative conversion in the FTIR spectra.
Figure 8B:
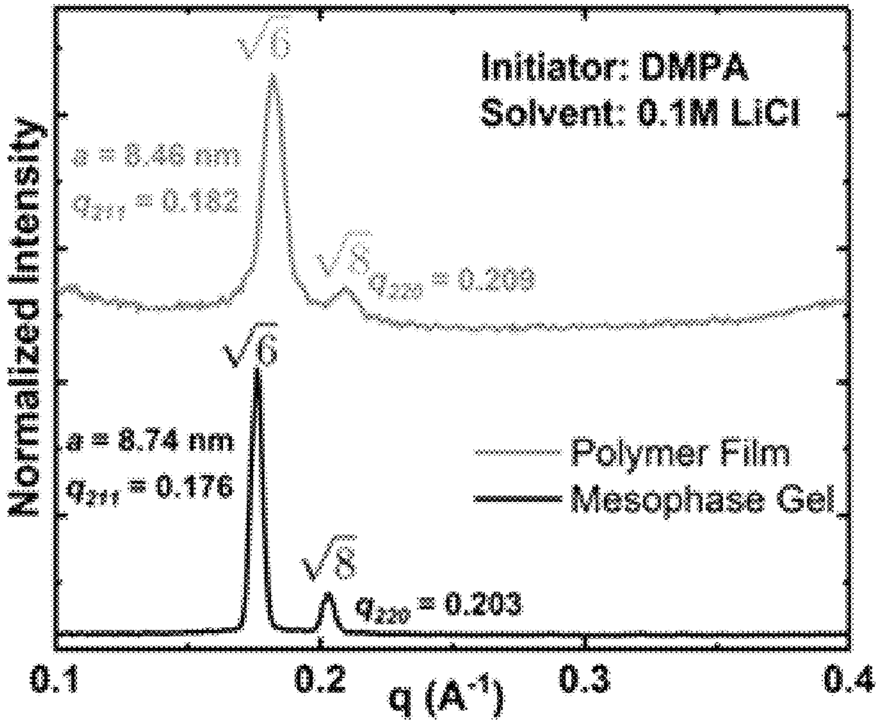
Figure 8C:
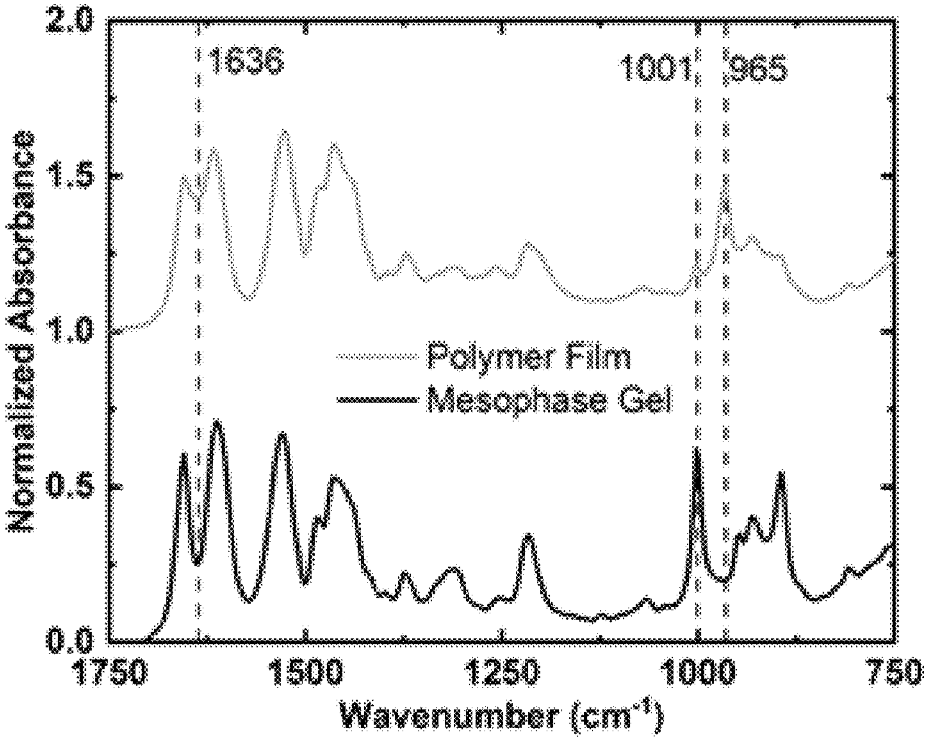
Figure 8D:
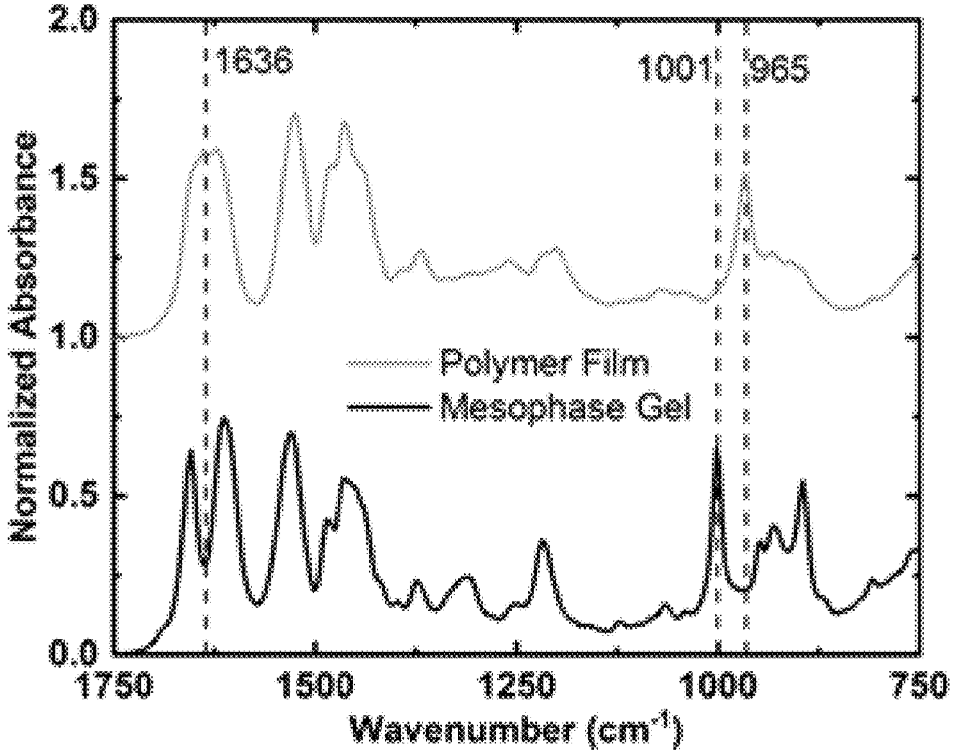

SAXS spectra of the mesophase and polymer films (FIG. 2F) display the characteristic peaks associated with the (211) and (220) planes of the double-gyroid structure (space group Ia3d), appearing at normalized scattering vector ratios of 1:√(4/3) (i.e., √8:√6). From these q-values, the lattice parameter a of the monomer mesophase and polymerized films was calculated to be 8.74 and 8.55 nm, respectively. No evidence of lattice swelling (i.e., change in a) was seen in dry vs. wet polymer films (FIGS. 6A-6B).

Figure 3A:
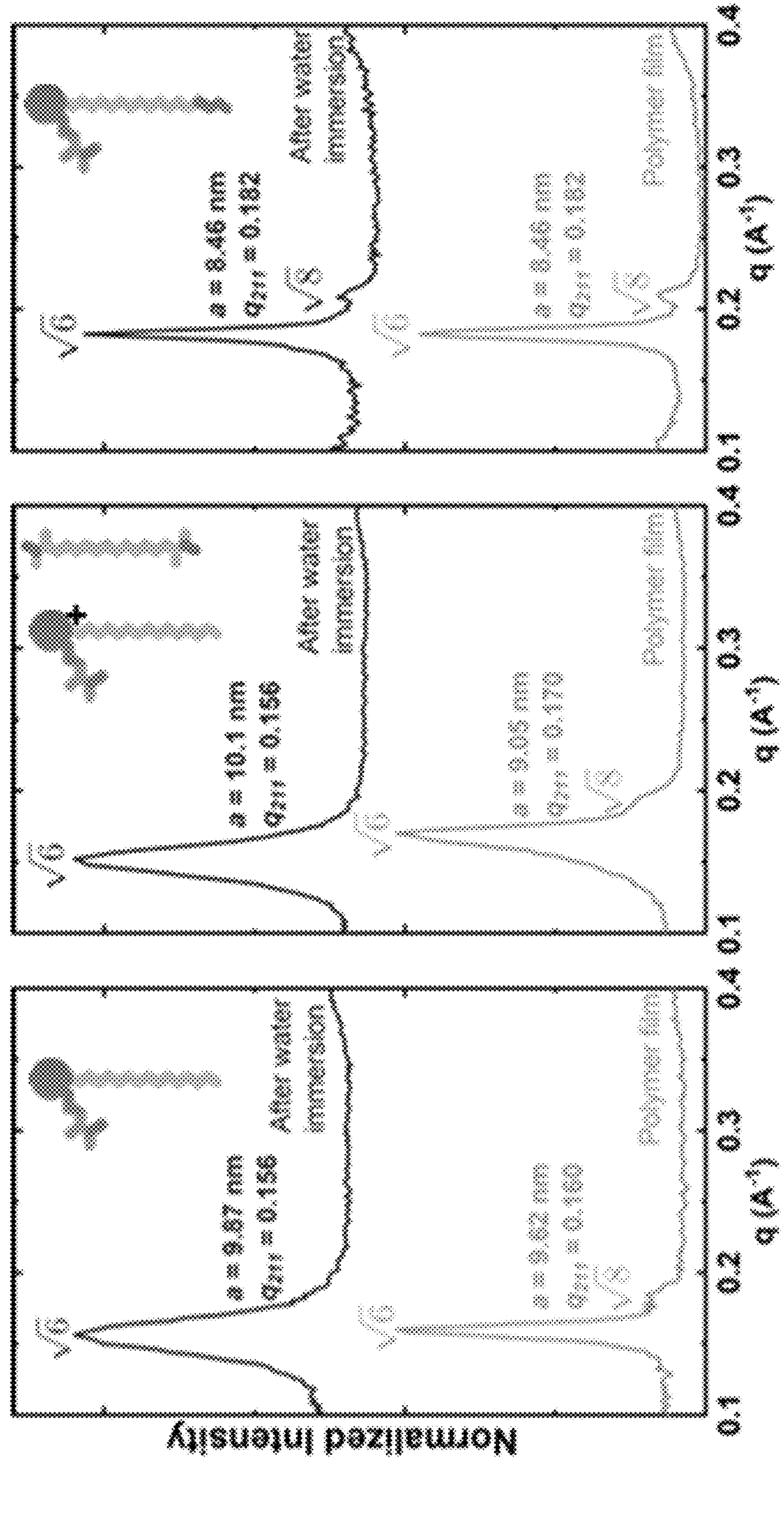
FIGS. 3A-3B provide SAXS plots (FIG. 3A) comparing degree of retention of double-gyroid phase after 24 h of water immersion for polymer films made from monomer 1b (left); monomer 1b+DDMA cross-linker (center); and monomer 1 (right); and SAXS plots summarizing the stability of the gyroid nanostructure in monomer 1-derived polymers at elevated temperatures, as well as in various solvent environments (at room temperature) (FIG. 3B).
Figure 3B:
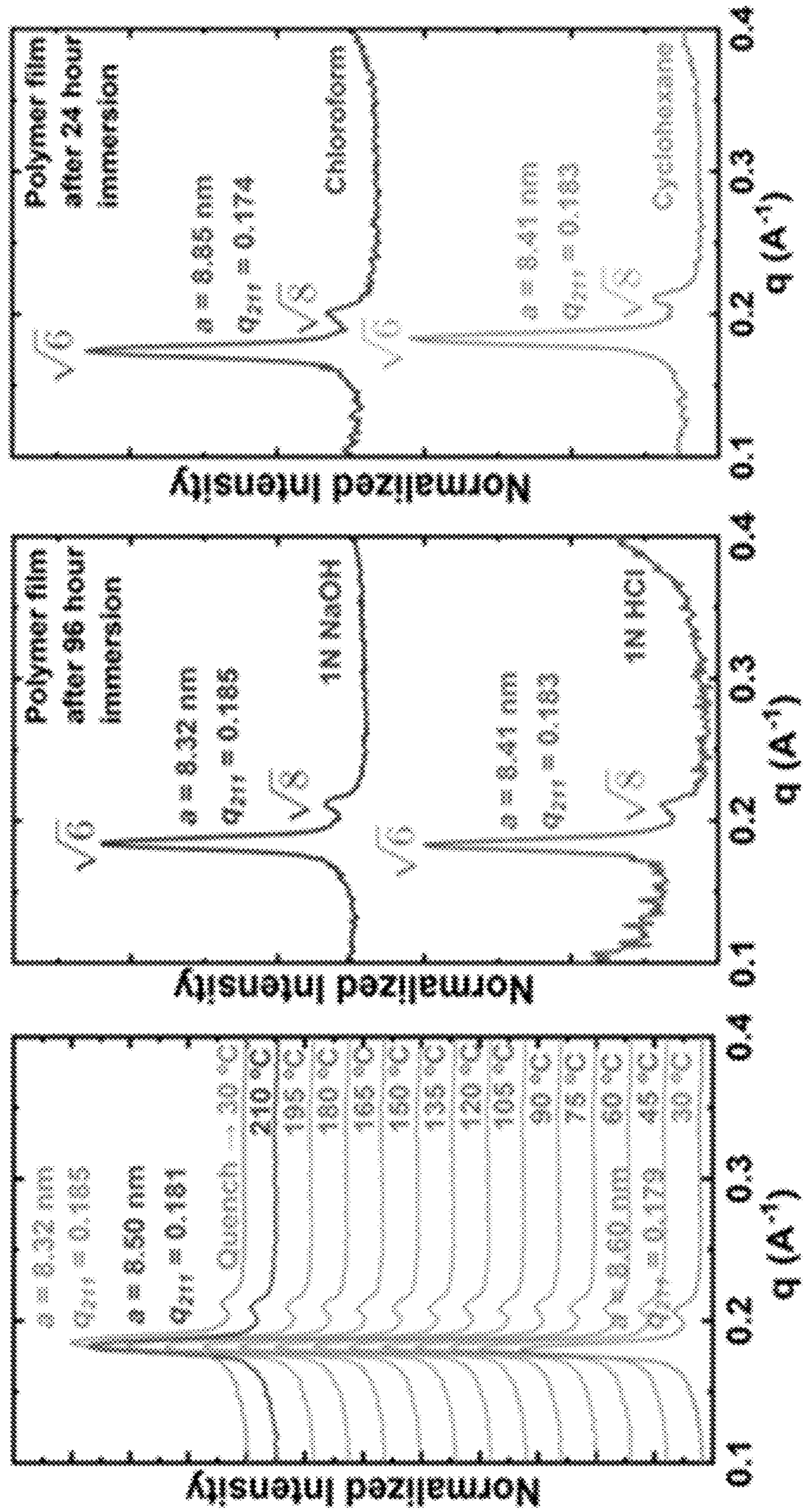

The fabrication of a Q-phase nanostructured polymer film does not always guarantee stability of the Q-phase microstructure at the molecular level. The novel structural motif of 1, with two chain-addition polymerizable groups at opposite ends of the molecule, affords significantly more Q-phase stability when polymerized than monomer 1b, a similar Q-phase-forming monomer with only one polymerizable group or the combination of 1b and an added bifunctional cross-linker (1,10-decanediol dimethacrylate (DDMA)). FIG. 3A compares the SAXS spectra of Q-phase films made from 1b (left), 1b+DDMA (center), and 1 (right) after water immersion for ca. 24 h. In both cases involving 1b, the SAXS spectra show successful retention of the gyroid phase upon cross-linking. However, after water immersion of these gyroid polymer films, SAXS analysis shows disappearance or significant diminishment of the (220) (i.e., √8) peak, along with an increase in the primary peak width and a larger value of the lattice parameter, consistent with partial or total loss of the double-gyroid nanostructure. Speculatively, this loss of structure upon water exposure may originate from a combination of leaching of monomers that were not cross-linked to the polymer matrix, and molecular scale rearrangement for monomers linked only at a single site. In contrast, the polymer film made from intrinsically cross-linkable 1 exhibited negligible difference in the SAXS traces of as-made and water-immersed films, indicating the Q-phase structure is much more robustly locked-in at the molecular level. Further testing of the polymer films confirmed that the gyroid polymers are stable to at least 210° C., and that they maintain their structure even after prolonged immersion in aqueous acid and base, as well as in organic and halogenated organic solvents (FIG. 3B). While there are prior reports of cross-linked gyroid structures produced from LLC monomers with more-complex structures, we are unaware of LLC-derived nanostructured polymers with the remarkable thermal and chemical/solvent stability demonstrated here.

Preliminary studies also show that the methacrylamide and diene groups in the hydrophilic vs. hydrophobic regions of the monomer can be initiated non-selectively, or with some degree of selectivity for one reactive group over the other, with retention of the Q phase. When water was used to form the Q phase of 1 with DMPA as a hydrophobic photo-initiator, FTIR analysis showed that the diene tails were largely polymerized, but only a small fraction of the methacrylamide groups near the head was converted. However, when a 0.1 M aq. LiCl solution was used to form the phase instead of pure water, near-quantitative conversion of both the head and tail polymerizable groups was achieved (FIGS. 7A-7D). It has been hypothesized that the increase in ionic strength of the aqueous phase may reduce the ability of the methacrylamides near the water/organic interface to reside near the aqueous phase, forcing them to reside more in the hydrophobic regions where the hydrophobic DMPA initiator and diene tails are located for more effective initiation of both groups.

The use of 2-hydroxy-4'-(2-hydroxyethoxy)-2-methylpropiophenone (HHMP), an uncharged, water-soluble radical photo-initiator, showed complete conversion of both the head and tail polymerizable groups (FIGS. 8A-8D), probably because its organic yet hydrophilic nature allows it to partition between the aqueous and organic domains and initiate groups residing in or near both. In each case, SAXS confirmed Q phase retention after partial or near-complete photopolymerization. Prior work on selective initiation of LLC monomers with two different polymerizable groups has only been demonstrated in vesicles for proof-of-concept, and selective polymerization in a Q phase is unprecedented. Although completely independent initiation of one reactive group over the other has not been achieved yet, these results suggest that it may be possible to alter the mechanical properties of gyroid films of 1 by controlling the degree of polymerization in the head vs. tail regions.

The nanoporous nature of the cross-linked gyroid polymers makes them natural candidates for applications such as selective adsorption and nanofiltration (NF). These applications have been pursued in other polymerized LLC phases, but the gyroid morphology is particularly valued because of its continuous percolated nature. The solvent and thermal stability of the cross-linked gyroid polymers suggest that they could be of interest in a wide range of selective transport applications, ranging from aqueous and organic solvent NF, to ion-conduction in ambient or harsh environments such as Li-ion batteries or alkaline fuel cells, respectively.

Figure 4A:
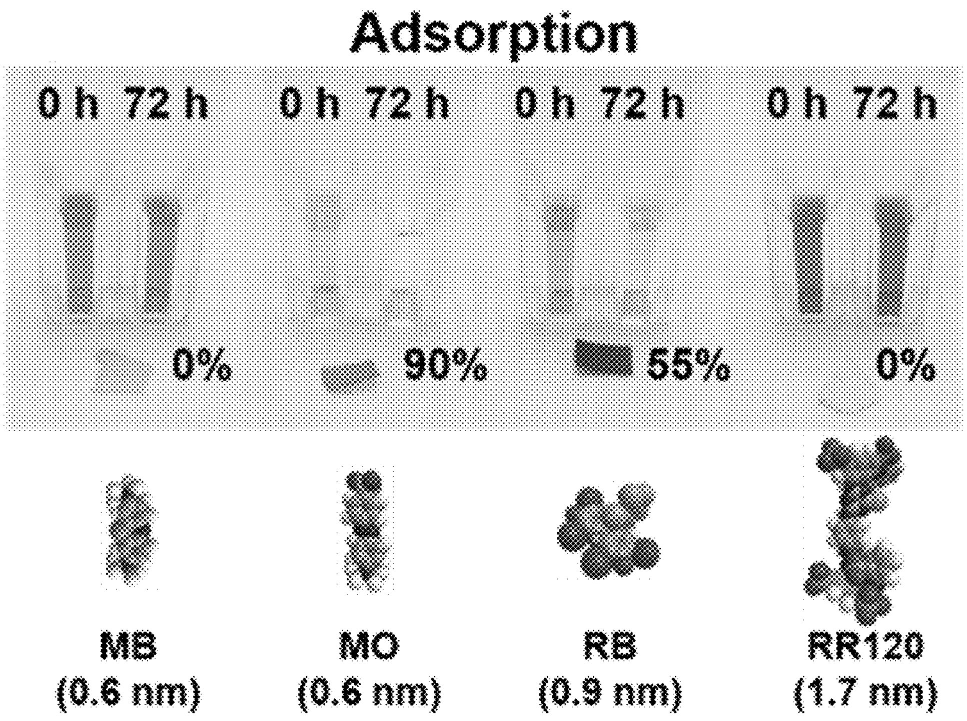
FIGS. 4A-4B provide photos of uptake of charged dyes into gyroid polymers (FIG. 4A), wherein the rejection of small cationic Methylene Blue (MB) and large anionic Reactive Red 120 (RR120) indicates the polymers have charge- and size-based selectivity; and a photo of Vitamin B12 (VB12) feed (F) and permeate (P) obtained from pressure-driven filtration of gyroid polymer membranes of 1, indicating 98% solute rejection (FIG. 4B).
Figure 4B:
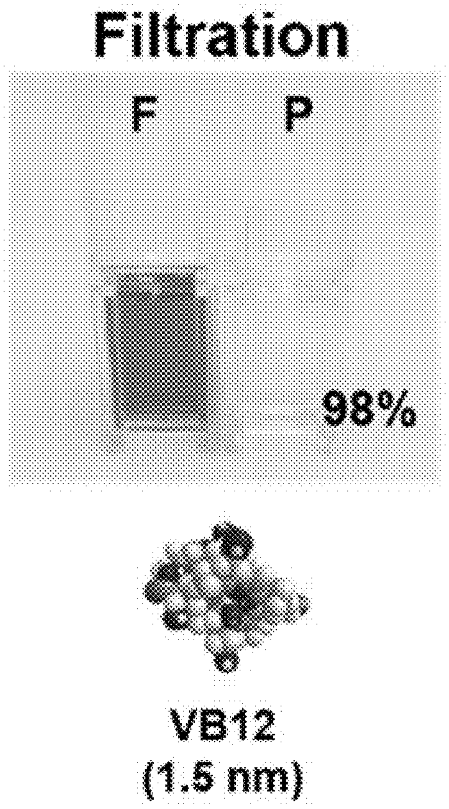

The theoretical pore size of the aqueous channels separating the intertwined gyroid structures was estimated as ca. 1.5 nm, and the specific surface area is estimated to be in the ca. 500 $m^2$ $g^{-1}$ range. FIG. 4A summarizes the uptake of various charged dyes into Q-phase polymer films of 1 immersed into aq. dye solutions for 72 h. The solute sizes reported are the calculated geometric mean dimensions of the molecules. The films showed no discernible uptake of Methylene Blue (MB), which at 0.6 nm is smaller than the estimated aqueous channel size. This rejection is likely due to electrostatic repulsion between this cationic dye and the positively charged interior surfaces of the membrane pores due to the quaternary ammonium group on the surfactant. In contrast, the negatively charged dyes Methyl Orange (MO, 0.6 nm), Rose Bengal (RB, 0.9 nm), and Reactive Red 120 (RR120, 1.7 nm) were taken up by the polymer, but the amount adsorbed is a function of the size of the dye. The lack of discernible uptake of RR120 suggests that it is simply too large to enter the channels of the polymer, despite favourable electrostatic attraction. These results qualitatively indicate that the pore size lies between 0.9 and 1.7 nm. This range of length scales is of interest for NF, as recently demonstrated in other LLC-based membranes. FIG. 4B shows a photograph of the permeate from the pressure-driven filtration of a Vitamin B12 feed (VB12, 1.5 nm) through a ca. 100-μm-thick gyroid polymer film of 1. The near-complete (98%) rejection of uncharged VB12 suggests that the effective pore size is in the range of 1.5 nm, consistent with the estimate from SAXS data. The thickness-normalized permeability of the films is roughly 0.1 L $m^{-2}$ $h^{-1}$ $bar^{-1}$ μm, which agrees well with previously reported NF data on cross-linked Q-phase films with similar pore sizes but made using more-complex LLC monomers.

Example 3: Design and Characterization of a Functional Q-Phase Polymer Monomer Intrinsically cross-linkable LLC monomer 1 was chosen as the gyroid-phase forming monomer because of its relatively simple and modular synthesis and because of the high thermal and chemical/solvent stability of the cross-linked network that it forms. Because of these features, a spiropyran-based derivative of 1 (i.e., monomer platform 2) was chosen as an initial design target for a functional Q-phase monomer, or as a functional monomer dopant for blending into the Q phase of 1, since spiropyran-merocyanine switching in response to various stimuli is well researched. Monomer 2SP was synthesized by reacting 1',3',3'-trimethyl-6-hydroxyspiro(2H-1-benzopyran-2,2'-indoline) with 18-bromooctadeca-1,3-diene in a solution of $K_2CO_3$ and $HCON(CH_3)_2$ at 80° C. via an $S_N2$ reaction. After purification, the structure and purity of 2SP were verified by $^1H$ NMR, $^{13}C$ NMR, FT-IR, UV-visible, HRMS, and elemental analyses, as described elsewhere herein. The acidochromic conversion of 2SP to 2M–HBr was achieved by dissolving 2SP in an 1:1 (v/v) solution of acetone:DCM and adding an equimolar amount of 0.422 M aq. HBr solution. The structure and purity of 2M–HBr were verified by $^1H$ NMR, $^{13}C$ NMR, FT-IR, UV-visible, HRMS, and elemental analyses, as described elsewhere herein. The 1,3-diene polymerizable tail was chosen for the spiropyran-based monomers to maintain compatibility with the polymerizable diene tail of 1.

Unfortunately, preliminary phase screening of 2SP and 2M–HBr did not reveal any relevant LLC phase behavior. The lack of LLC behavior echoes the general difficulty in designing novel Q-phase-forming LLC monomers. Previous studies have shown that blending and co-polymerization of functionalized non-LLC-phase-forming monomers with LLC monomers of similar structure can yield functional polymer networks with the desired phase. However, the formation of functionalized cross-linkable LLC blends using this approach has only been demonstrated to be possible with the $H_{II}$ phase. Q-phase-forming monomers have been blended with co-monomers to tune the Q-phase window, but there is yet to be an example in which a functional co-monomer is blended with a Q-phase monomer to yield a Q-phase material with functional properties outside of basic molecular sieving.

Despite the lack of LLC phase behavior from monomers 2SP and 2M–HBr, various blends of 1 and these two forms of 2 were prepared with a goal of evenly distributing the spiropyran-based monomer throughout the resulting gyroid LLC phase with retention of the spiropyran functional group's chromic sensitivity. Because gyroid phases were obtained with blends of both (1+2SP) and (1+2M–HBr), these monomeric blends are referenced herein as (1+2) for brevity.

It was found that 0.5-1.2 wt % of 2 with respect to 1 formed a stable gyroid phase at a composition of 87.5/11.5/

1.0 (w/w/w) monomer blend (1+2)/water/2,2-dimethoxy-2-phenylacetophenone (DMPA, a radical photo-initiator) at room temperature (22° C.). Polymer films with retention of the gyroid structure (typical thicknesses between 50-150 μm) were obtained by radically photo-cross-linking the monomer mesophase with 365-nm UV light under $N_2$ purge for ca. 3 h at room temperature. FT-IR spectroscopy confirmed the near-complete conversion of the polymerizable groups (FIG. 16). The monomer mesophase and resulting cross-linked polymer films exhibited uniformly dark images under polarized light microscopy (PLM) analysis, consistent with the optically isotropic nature of Q phases. Small-angle X-ray scattering (SAXS) spectra of the monomer mesophase and cross-linked films revealed the characteristic $\sqrt{6}:\sqrt{8}$ relative Bragg peak locations associated with a gyroid-type Q phase (FIG. 11E). Temperature stability studies on the polymer films of these (1+2) blends indicated that the cross-linked gyroid phase is stable up to 120° C. with no distinct changes to the lattice parameter beyond a small amount of temperature-induced drying (FIG. 17). Unlike the colorless materials formed with just monomer 1, the monomer mesophases and polymer films of (1+2)/described herein are slightly colored (e.g., very pale yellow to very pale orange) due to the added spiropyran-based dopant monomer.

Figure 18:
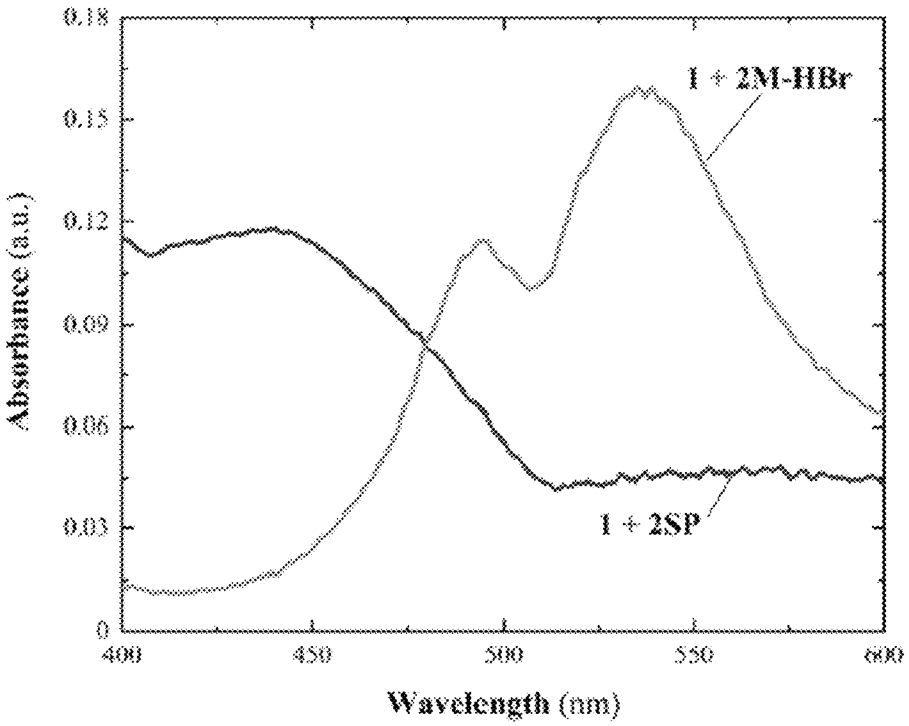
FIG. 18 provides a graph depicting typical UV-visible absorption spectra of a cross-linked bulk gyroid-phase film of (1+2) before and after exposure to aq. HBr solution. The full conversion of the spiropyran group (2SP) to the protonated-merocyanine form (2M–HBr) occurs after treatment with aq. HBr.
Figure 19A:
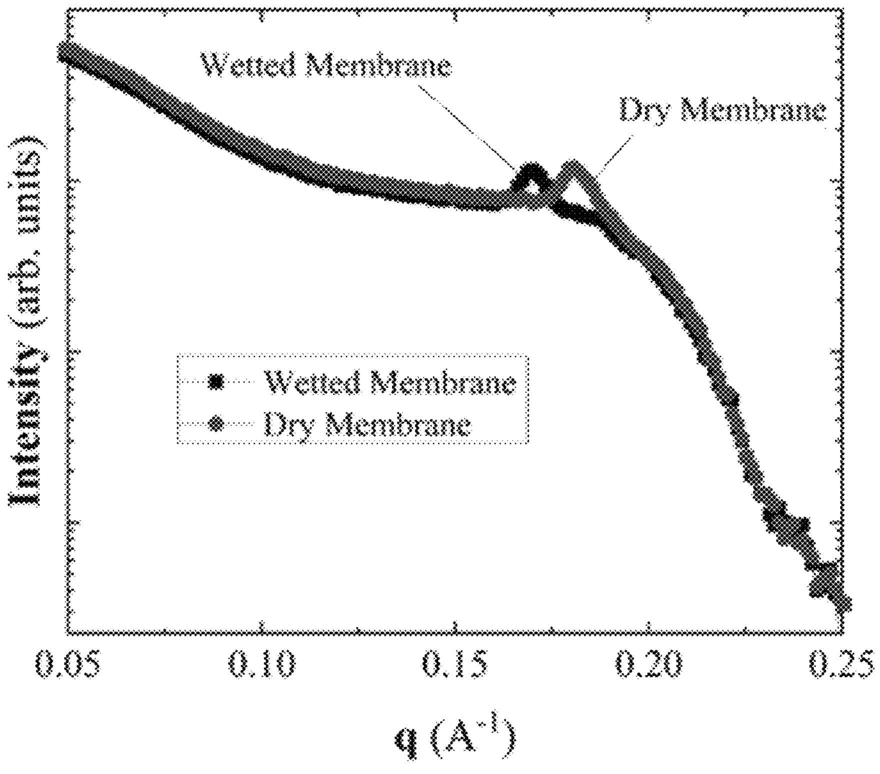
FIGS. 19A-19B provide SAXS spectra of a cross-linked gyroid-type $Q_I$ film of (1+2) with no 0.422 M aq. HBr treatment (FIG. 19A) and the same film after being treated with 0.422 M aq. HBr (FIG. 19B); all spectra were measured under non-vacuum, ambient conditions.
Figure 19B:
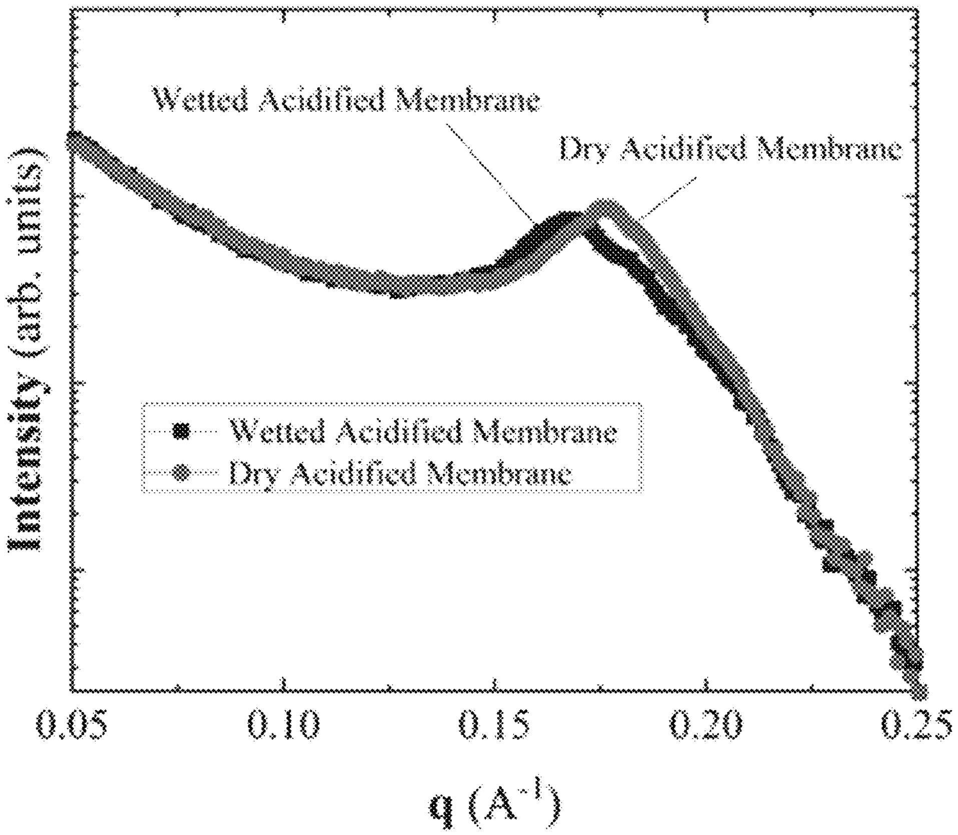

The spiropyran-doped gyroid-phase polymer films described above were initially treated with aq. acid as the chromic stimulus. Acid exposure was the first choice of stimulus due to the excellent acid stability of cross-linked gyroid films of 1 and the availability of commercial aq. HBr solutions. Also, the use of HBr would not result in counter-anion mixtures with the Br− ions on monomers 1 and 2, which would complicate structural analysis. Upon soaking the spiropyran-doped films in aq. solutions of varying pH, UV-vis analysis confirmed effectively complete conversion of the 2SP units to their 2M–HBr form in the films (FIG. 18). In addition, SAXS analysis confirmed retention of the gyroid nanostructure, with slight lattice swelling (i.e., an increase in unit cell parameter, a) observed in the wet vs. dry polymer films (FIGS. 19A-19B).

Despite the evidence of lattice swelling upon exposure to aq. HBr solution, $^1$H NMR studies of the polymer films soaked in $D_2O$ (FIG. 20) revealed no leaching of 2 from the bulk cross-linked network, thus indicating that 2 was successfully cross-linked within the bulk polymer film. Previous studies of gyroid-phase polymer films of 1 revealed no lattice swelling. Without wishing to be bound by theory, the lattice swelling of the present system is likely due to the presence of the spiropyran dopant monomer. It has been proposed that the otherwise densely cross-linked network is interrupted by the addition of non-cross-linking monomer 2, the diene tail of which will only polymerize within the hydrophobic domains of the formed gyroid phase.

This implies that around the hydrophilic domains (i.e., water nanopores) where the spiropyran moiety is likely situated, there is greater free volume since the spiropyran headgroup is not covalently linked to the walls of the hydrophilic domains. Due to the increased free volume near the hydrophilic pores, this system shows promise for functional behavior depending on the chemical state that the spiropyran monomer is in (i.e., 2SP vs. 2M–HBr) in response to an external stimulus (e.g., acid).

Example 4: Effect of Spiropyran Acidochromism on the Gyroid Unit Cell of Cross-Linked (1+2)

Figure 11A:
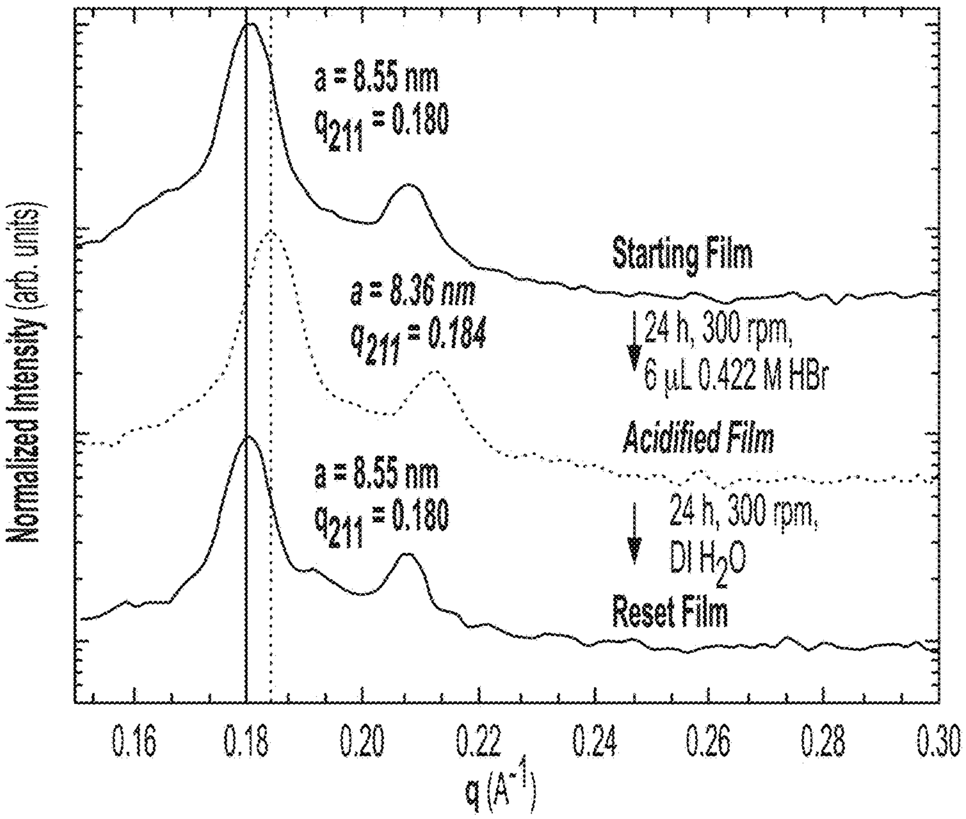
FIG. 11A provides a SAXS spectra depicting the stimulus response of gyroid-phase polymer films of (1+2) to external aqueous solution pH with retention of the overall gyroid phase. A reversible shift in a was observed between gyroid-phase films soaked in neutral pH vs. acidic pH.
Figure 11B:
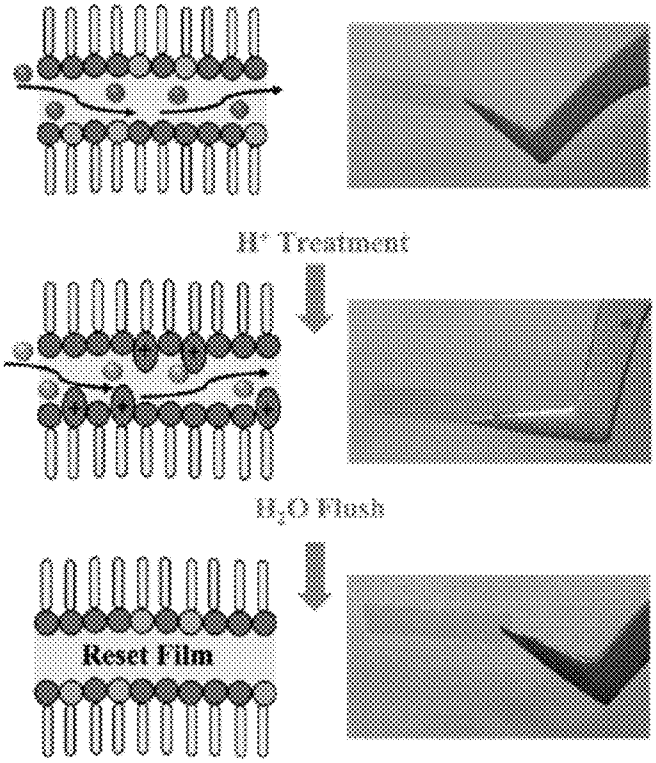
FIG. 11B provides a schematic representation and photos of a cross-linked gyroid film pre-acidification, post-acidification, and neutralization ($H^+$ ions and water molecules are depicted, with curved arrows indicating direction of solvent/ion flow).
Figure 21:
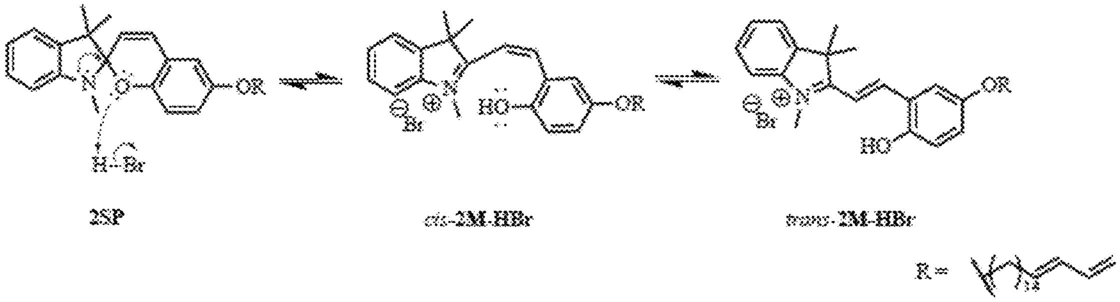
FIG. 21 provides a scheme depicting the general mechanism of the acid-promoted shift from 2SP to 2M–HBr with aq. HBr solution. Note that the cis-2M–HBr isomer may equilibrate with the trans-2M–HBr isomer, but that the trans-isomer is the most stable form.

External stimuli can effectively mediate the chromic switching of the spiropyran-based monomer but are expected to have little impact on the overall integrity of the cross-linked material. Since the 2M–HBr form has a positive charge and may possess various open-form states (FIG. 21), it was expected that the environment of the aqueous domains of the nanoporous gyroid material would change upon exposure to acid. An excess of 0.422 M aq. HBr was used to promote the acidochromic shift of 2SP to 2M–HBr in a cross-linked gyroid-phase film suspended in solution. SAXS analysis revealed that the crosslinked films not only maintained the gyroid structure upon acidification but also exhibited a fully reversible change in their unit cell dimensions upon neutralization of the solution pH (FIGS. 11A-11B). Furthermore, the cross-linked films exhibited reversible color changes upon acidification and neutralization of their external solution pH (i.e., from pale yellow to vibrant red and the reverse, respectively).

After confirming the stability of the gyroid phase during repeated acid exposure, the overall effect of calculated external solution acid concentration on the calculated relative pore diameter of the gyroid network was explored. Different pieces of the same original polymer film were exposed to various concentrations of acid and then analyzed by SAXS and photographed. A clear dependence of the calculated pore diameter on the acidity of the solution is observed (FIG. 12). For gyroid polymer films made with 0.8 wt % or 1.2 wt % of monomer 2, at the most acidic pH studied the calculated relative pore diameter change was approximately 5.0% smaller than the original calculated pore diameter. The rate of change of pore diameter with pH is dependent on the amount of 2 present in the system. In the absence of 2, the pore size is insensitive to pH. However, for films with 0.8 and 1.2 wt % loading of 2, the pore size shows a slope of 0.85 and 1.2 per pH unit increase, respectively. The differences in these coefficients are statistically meaningful.

Example 5: Changes in Water Vapor Transport Through Bulk Gyroid Films of Cross-Linked (1+2)

The reversible response of the cross-linked gyroid unit cell under acidic conditions, coupled with an estimated shrinkage of 4.5-5.5% in calculated relative pore diameter, suggested that water vapor transport rates could be meaningfully affected by varying solution pH. Similar transitions have been observed in the construction of devices for acid vapor pH identification, although none have been embedded within a nanoporous gyroid LLC network.

Figure 13A:
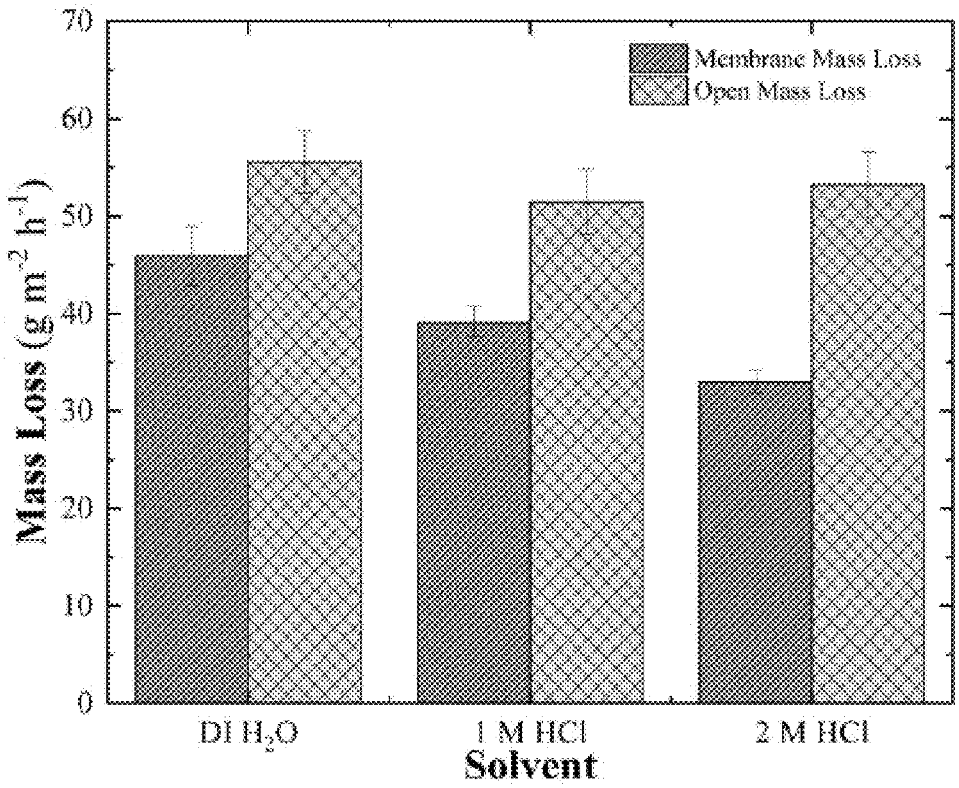
FIG. 13A provides a bar graph depicting instantaneous mass flow rates (N=10-14) at room temperature (22° C.) for film vapor cells in a desiccator filled with Drierite®, compared to cells that were left open (i.e., open vials). Thicknesses of the bulk gyroid polymer films of (1+2) tested in each experiment: DI $H_2O$: 0.135 μm; 1 M aq. HCl: 0.140 μm; 2 M aq. HCl: 0.138 μm. Error bars represent ±1 standard deviation.
Figure 13B:
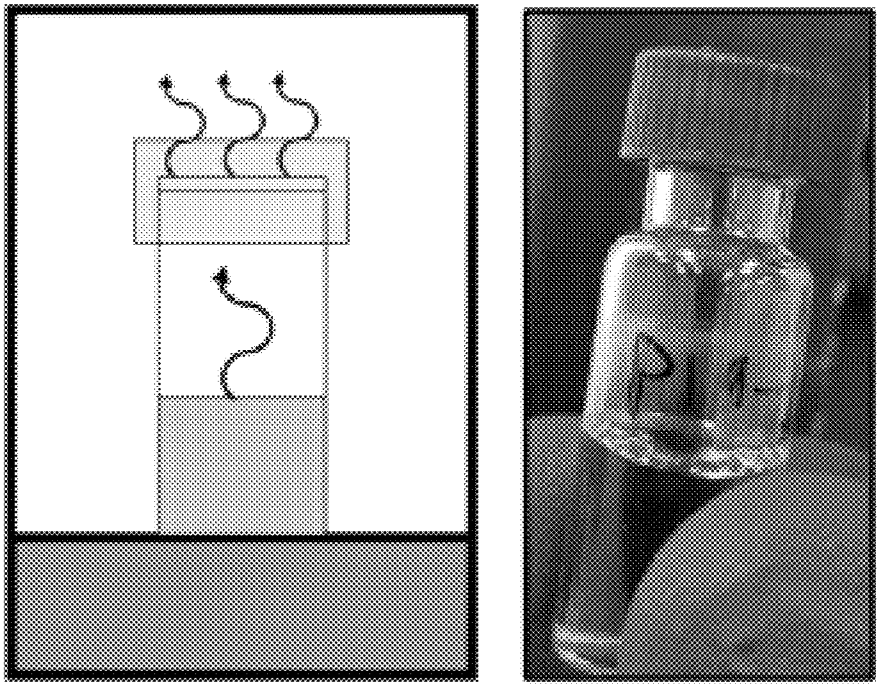
FIG. 13B provides a schematic representation of the experimental setup for vapor transport experiments.
Figure 13C:
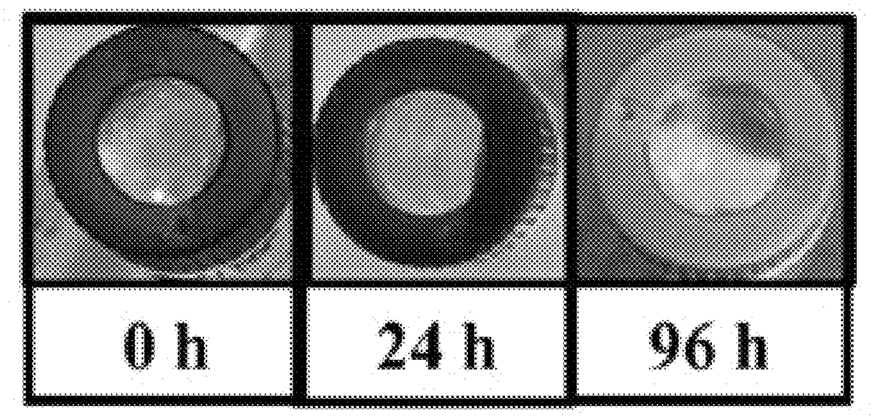
FIG. 13C provides images of film during the course of the experiment with 2 M aq. HCl (0 h), wherein the first observation of significant color change in film occurred at 24 h, and a steady state occurred at 96 h.
Figure 22:
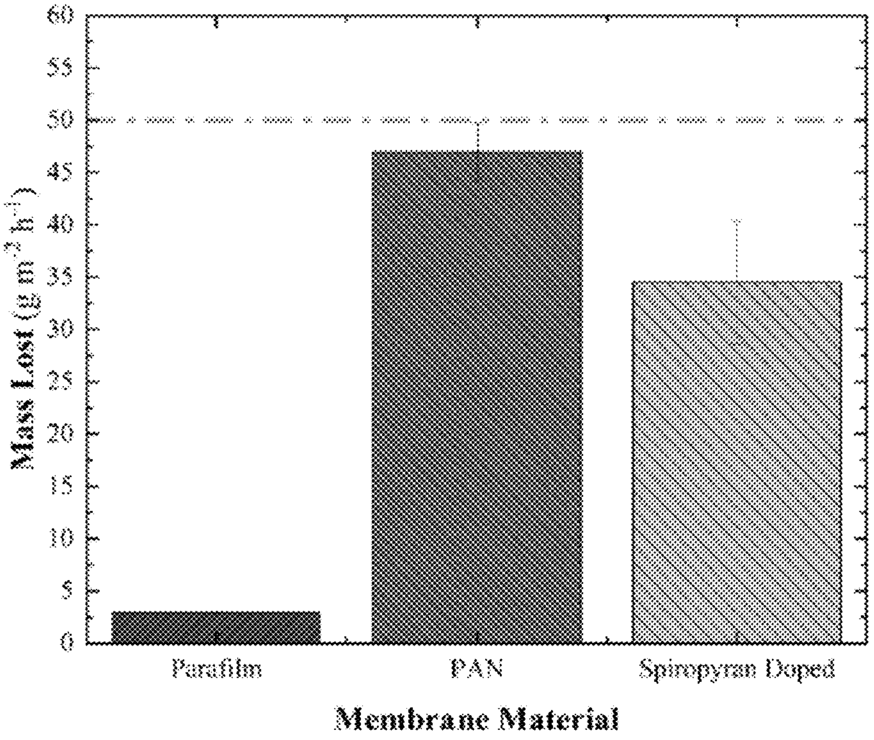
FIG. 22 provides a bar graph depicting room-temperature water mass-loss rates for film vapor cells in a desiccator filled with Drierite® comparing spiropyran-doped films against commercial membranes. The dashed line indicates the open-cell rate of ca. 50 g $m^{-2}$ $h^{-1}$ under the test conditions. Thicknesses of each film material were: bulk hydrophobic Parafilm™=22 μm; PAN supported on porous PET=177 μm composite membrane total thickness, 94 μm for the PAN active top layer (Sterlitech); and bulk spiropyran-doped gyroid film=99 μm. Error bars represent ±1 standard deviation.

Pieces of a gyroid film containing 0.8 wt % 2 were sealed over the top of a glass-vial cell above a solution containing varying concentrations of aq. HCl. The rate of water vapor transport through the bulk films was then measured by observing the mass loss in the liquid reservoir over a period of two weeks at room temperature (22° C.). Each film was also checked to ensure the absence of pinhole defects. Pure de-ionized (DI) water (0 M HCl) and two aq. HCl solutions (1 M, and 2 M HCl) were chosen to indicate the most significant color changes in the films, which signified reaching a steady state by the films changing to a deep red color in the case of acidified samples. FIGS. 13A-13C show that for the aq. acidic solutions studied, the open-vial (i.e., no membrane film) water vapor loss rates were all similar (within statistical significance). However as the acid concentration increased, the steady-state vapor mass loss rate through the cells capped with spiropyran-doped films decreased. Specifically, non-acidic water vapor was lost at 83.0% of the rate for an open vial; 1 M aq. HCl vapor was lost at 76.1% of that for an open vial; and 2 M aq. HCl vapor was lost at 54.3% of that for an open vial. These water mass loss rates are competitive with commercially available, microporous supported membranes, such as polyacrylonitrile (FIG. 22). The decrease in evaporation rate with respect to acid concentration is larger than expected for an approximate 4-5% decrease in calculated pore diameter for an Ia3d gyroid space group. Upon exposure to low-pH water vapor, all the 2SP groups in the film will have reacted to their 2M–HBr form. It has been hypothesized that further electrostatic interactions may also be taking place between the 2M–HBr groups in the films and the HCl in the water vapor, further slowing diffusion once a steady state is reached. In summary, these spiropyran-doped gyroid networks can effectively transport water vapor, act as a color indicator for acid in the permeating water vapor, and alter the vapor transport rate as a function of the water vapor acidity.

Example 6: Preliminary Studies of UV-Light-Mediated Pb2+ Ion Uptake in Bulk Gyroid Films of Cross-Linked (1+2)

Figure 14A:
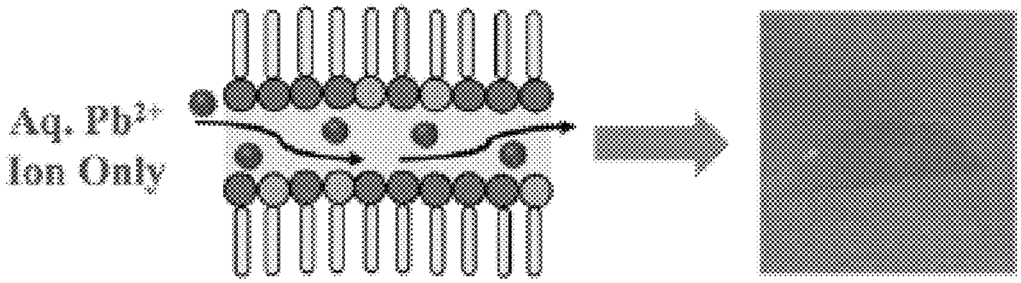
FIGS. 14A-14D provide schematics and photos of gyroid polymer films of (1+2) depicting: a lack of merocyanine formation upon exposure to aq. $Pb^{2+}$ ions and water only (FIG. 14A); lack of merocyanine formation upon exposure to UV light and water only (FIG. 14B); merocyanine formation upon exposure to aq. $Pb^{2+}$ ions, UV light, and water (FIG. 14C); and SAXS spectra (FIG. 14D) confirming retention of the gyroid phase in the polymer films upon exposure to the combinations of stimuli in the experiments of FIGS. 14A-14C.
Figure 14B:
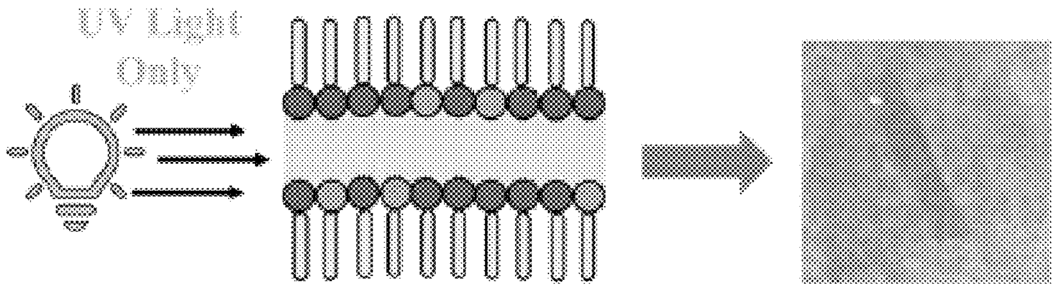
Figure 14C:
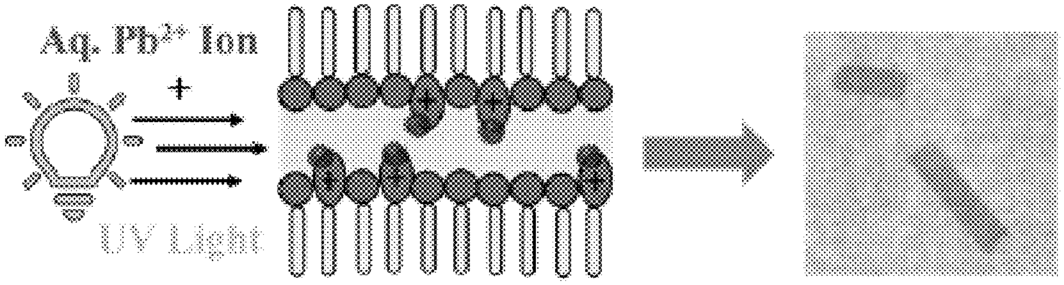
Figure 14D:
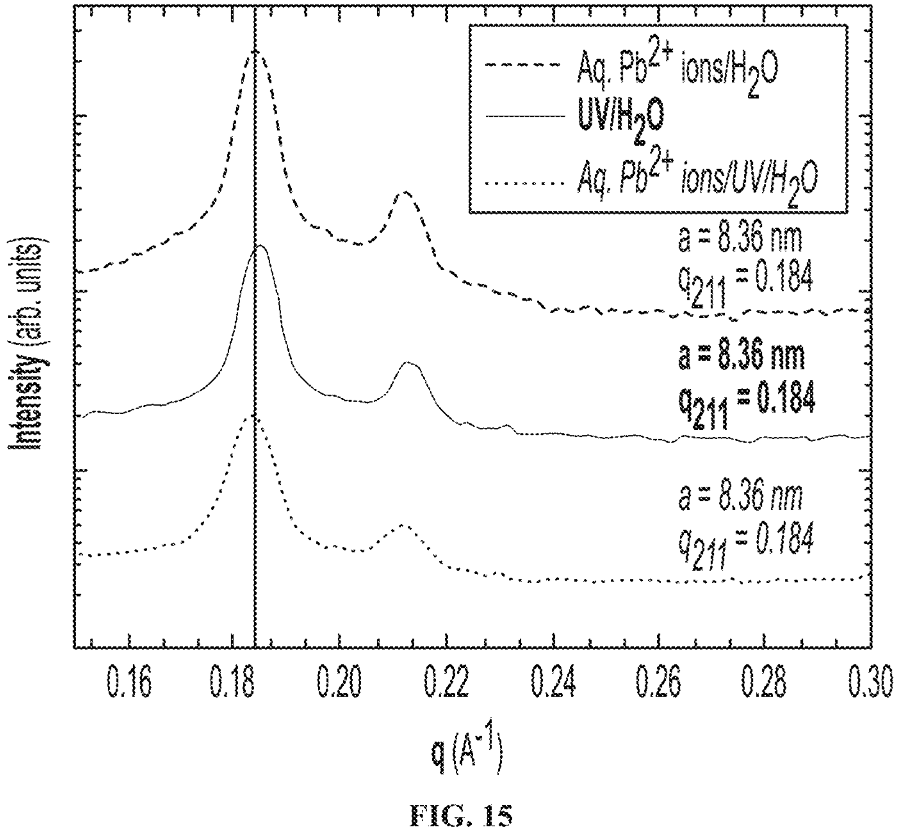
Figure 15:
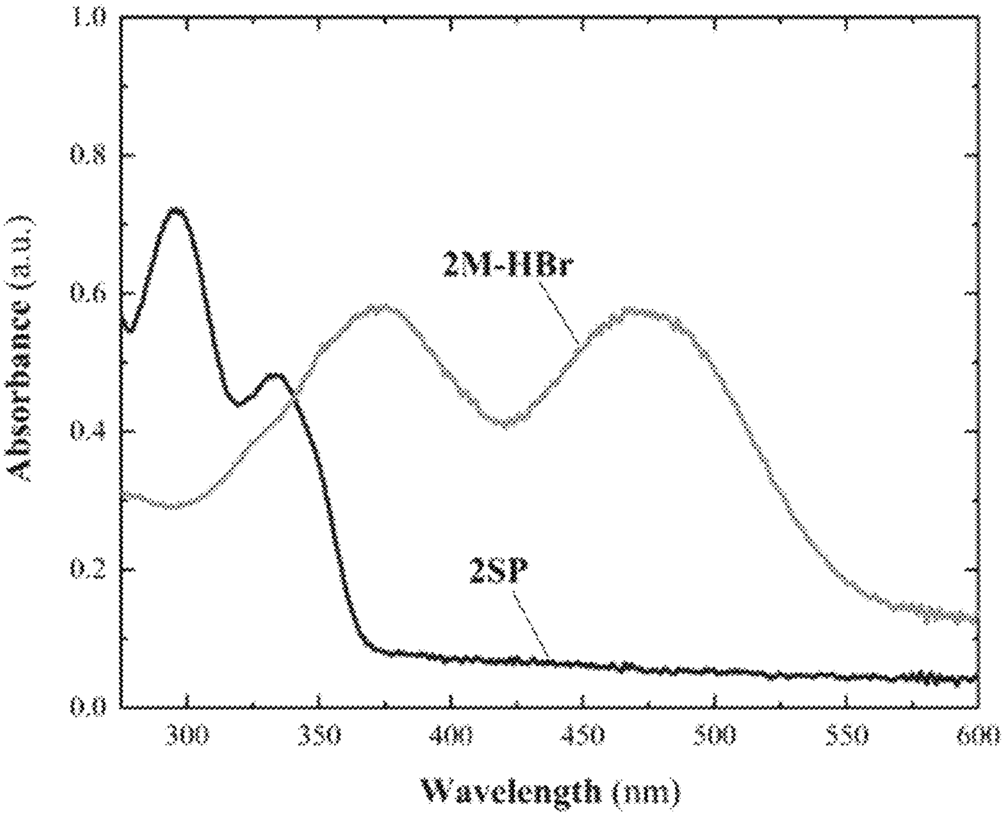
FIG. 15 provides a graph depicting the UV-visible absorption spectra of monomer 2SP and separately monomer 2M–HBr dissolved in 1:1 (v/v) acetone/$CH_2Cl_2$.

Spiropyran groups are also known to undergo UV-light-induced isomerization to the zwitterionic, non-protonated merocyanine form (i.e., 2M for monomer 2), without need for added acid. The colored merocyanine form can also isomerize back to the uncharged spiropyran form upon irradiation with visible light. The zwitterionic merocyanine isomer has been incorporated onto a range of materials and used for metal ion chelation, amino acid transport, or simple logic gate operations. Based on these prior studies, an initial study was designed to probe for a chromic response of the gyroid polymer films of (1+2) upon exposure to aq. $Pb^{2+}$ ions and UV light (FIGS. 14A-14D). The merocyanine coloration was only observed when a piece of the spiropyran-doped gyroid polymer was soaked in water, exposed to aq. $Pb^{2+}$ ions, and subjected to 365-nm light for 5 h at 22° C. $Pb^{2+}$ ions were chosen because literature studies have shown that $Pb^{2+}$ ions have the highest binding affinity to the phenolate unit on the merocyanine isomer. Control experiments revealed that UV light exposure or aq. $Pb^{2+}$ ions alone were not enough to trigger an observable chromic response in the gyroid films of (1+2). Furthermore, FIG. 14D shows that the gyroid phase of the films was retained in each case. Despite prolonged exposure of these films to DI $H_2O$ and intense visible light irradiation, the merocyanine coloration was not observed to revert to the colorless spiropyran form. These results indicate that upon UV irradiation, this spiropyran-based nanoporous material acts as an effective trap for $Pb^{2+}$ ions and the tightly bound $Pb^{2+}$ ions stabilize the generated merocyanine form within the bulk polymer.

Enumerated Embodiments

The following exemplary embodiments are provided, the numbering of which is not to be construed as designating levels of importance:

Embodiment 1 provides a composition comprising a compound of Formula (I), or a solvate, stereoisomer, or salt thereof:

(I)

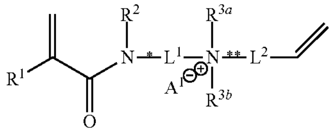

wherein:

$R^1$ is selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^2$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^{3a}$ and $R^{3b}$ are each independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^1$ is selected from the group consisting of optionally substituted $C_1$-$C_{10}$ alkylenyl and optionally substituted $C_2$-$C_{10}$ alkenylenyl;

$L^2$ is selected from the group consisting of optionally substituted $C_1$-$C_{100}$ alkylenyl and optionally substituted $C_2$-$C_{100}$ alkenylenyl; and $A^1$ is a counter anion.

Embodiment 2 provides composition of embodiment 1, wherein at least one of the following applies:

(a) $R^1$ is $CH_3$;
(b) $R^2$ is H;
(c) $R^{3a}$ and $R^{3b}$ are each independently $CH_3$;
(d) $L^1$ is *—$CH_2CH_2CH_2$—;
(e) $L^2$ is **—$(CH_2)_{14}CH{=}CH$—; and
(f) $A^1$ is bromide.

Embodiment 3 provides the composition of any one of embodiments 1, wherein the compound of Formula (I) is:

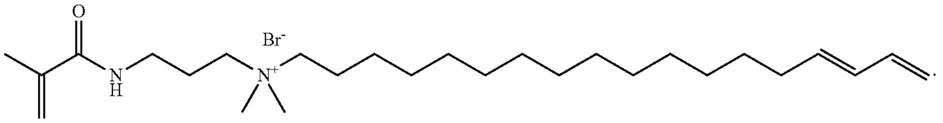 [SMILES: C=C/C=C/CCCCCCCCCCCCCC[N+](C)(C)CCCNC(=O)C(=C)C ; [Br-]]

Embodiment 4 provides the composition of any one of embodiments 1, wherein the compound of Formula (I) comprises about 80% to about 90% of the composition by weight (w/w %).

Embodiment 5 provides the composition of any one of embodiments 1, wherein the composition further comprises a solvent, optionally wherein the solvent is water.

Embodiment 6 provides the composition of any one of embodiments 5, wherein the solvent comprises about 5% to about 15% of the composition by weight (w/w %).

Embodiment 7 provides the composition of any one of embodiments 5, wherein the solvent is water and the compound of Formula (I) and the water have a ratio selected from the group consisting of about 87.5:11.5, 88:11, and 84:11 by weight.

Embodiment 8 provides the composition of any one of embodiments 1, wherein the composition further comprises at least one compound selected from the group consisting of:

(a) a compound of Formula (IIa), or solvate, stereoisomer, or salt thereof:

(IIa)

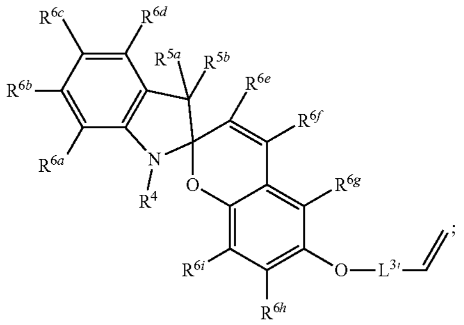

and (b) a compound of Formula (IIb), or solvate, stereoisomer, or salt thereof:

(IIb)

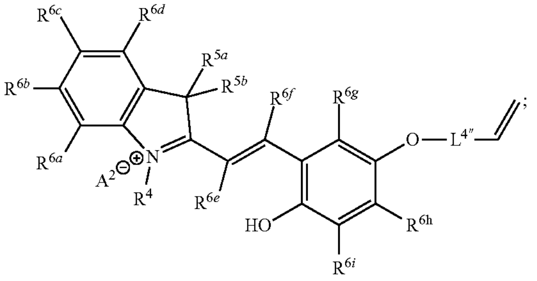

wherein:

each occurrence of $R^4$ is selected from the group consisting of H, optionally substituted $C_1$-$C_6$ alkyl, optionally substituted $C_3$-$C_8$ cycloalkyl, optionally substituted $C_2$-$C_8$ heterocycloalkyl, optionally substituted $C_6$-$C_{10}$ aryl, and optionally substituted $C_5$-$C_{10}$ heteroaryl;

each occurrence of $R^{5a}$ and $R^{5b}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

each occurrence of $R^{6a}$, $R^{6b}$, $R^{6c}$, $R^{6d}$, $R^{6e}$, $R^{6f}$, $R^{6g}$, $R^{6h}$, and $R^{6i}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^3$ and $L^4$ are each independently selected from the group consisting of optionally substituted $C_1$-$C_{100}$ alkylenyl and optionally substituted $C_2$-$C_{100}$ alkenylenyl; and $A^2$ is a counter anion.

Embodiment 9 provides the composition of any one of embodiments 8, wherein at least one of the following applies:

(a) $R^4$ is $CH_3$;

(b) $R^{5a}$ and $R^{5b}$ are each independently $CH_3$;

(c) $R^{6a}$, $R^{6b}$, $R^{6c}$, $R^{6d}$, $R^{6e}$, $R^{6f}$, $R^{6g}$, $R^{6h}$, and $R^{6i}$ are each independently H;

(d) $L^3$ is $-(CH_2)_{14}CH{=}CH$-';

(e) $L^4$ is $-(CH_2)_{14}CH{=}CH$-"; and (f) $A^2$ is bromide.

Embodiment 10 provides the composition of any one of embodiments 8, wherein at least one of the following applies:

(a) the compound of Formula (IIa) is:

(IIa)

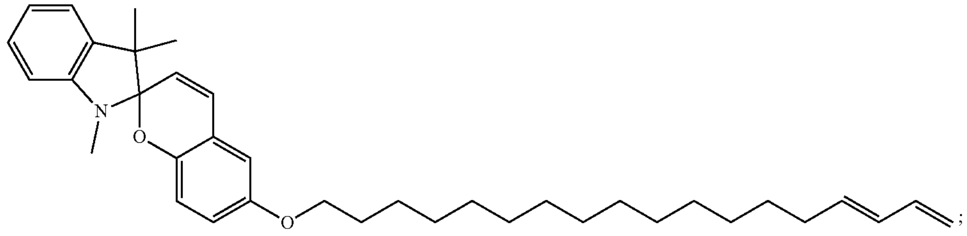

and (b) the compound of Formula (IIb) is:

(IIb)

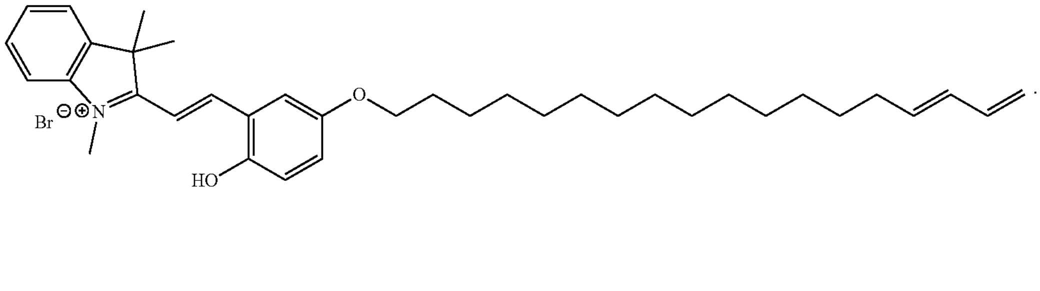

Embodiment 11 provides the composition of any one of embodiments 8, wherein at least one of the following applies:

(a) the compound of Formula (IIa) and Formula (IIb) each independently comprise about 0.1% to about 5% of the composition by weight (w/w %);

(b) the compound of Formula (I) and the compound of Formula (IIa), Formula (IIb), or mixture thereof have a ratio of about 86.5:1 by weight (w/w %).

Embodiment 12 provides a polymer composition comprising a polymerized product of the composition of any one of embodiments 1-11.

Embodiment 13 provides polymer composition of embodiment 12, wherein the polymer comprises a plurality of nanoholes.

Embodiment 14 provides the composition of any one of embodiments 12-13, wherein the polymer comprises an aqueous lyotropic liquid crystal (LLC) phase comprising a gyroid bicontinuous cubic (Q-phase) morphology.

Embodiment 15 provides polymer composition comprising the polymerized product of the composition of any one of embodiments 1-11, wherein the polymer composition comprises the reaction product of two or more compounds selected from the group consisting of the compound of Formula (I), the compound of Formula (IIa), and the compound of Formula (IIb), wherein each of the following apply:

(a) a covalent bond is formed between at least one alkene of a first compound of Formula (I) and at least one alkene of a second compound of Formula (I);

(b) a covalent bond is formed between at least one alkene of the compound of Formula (I) and at least one alkene of the compound of Formula (IIa) or the compound of Formula (IIb).

Embodiment 16 provides the polymer composition of embodiment 15, wherein the polymer composition is responsive to external stimuli, wherein at least one of the following applies:

(a) the external stimuli is at least one selected from the group consisting of pH changes, UV irradiation, and/or $Pb^{2+}$ ions; and (b) the response is selected from the group consisting of changes in color and changes in unit cell dimensions.

Embodiment 17 provides a method of preparing the polymer composition of any one of embodiments 1-16, the method comprising:

(a) contacting the compound of Formula (I) and a photoinitiator in the presence of a solvent to provide a gyroid mesophase gel; and (b) irradiating the gyroid mesophase gel with UV light.

Embodiment 18 provides the method of embodiment 17, wherein at least one of the following applies:

(a) the photoinitiator is selected from the group consisting of 2,2-dimethoxy-2-phenylacetophenone (DMPA) and 2-hydroxy-4'-(2-hydroxyethoxy)-2-methylpropiophenone (HHMP);

(b) the solvent is water; and (c) the compound of Formula (I), photoinitiator, and solvent have a ratio of about 87.5:11.5:1, 88:11:1, and 84:11:1 by weight (w/w %).

Embodiment 19 provides a method of preparing the polymer composition of any one of embodiments 1-15, the method comprising:

(a) contacting the compound of Formula (I); the compound of Formula (IIa), Formula (IIb), or a mixture thereof; and a photoinitiator in the presence of a solvent to provide a gyroid mesophase gel; and (b) irradiating the gyroid mesophase gel with UV light.

Embodiment 20 provides the method of embodiment 19, wherein at least one of the following applies:

(a) the photoinitiator is selected from the group consisting of 2,2-dimethoxy-2-phenylacetophenone (DMPA) and 2-hydroxy-4'-(2-hydroxyethoxy)-2-methylpropiophenone (HHMP);

(b) the solvent is water; and (c) the compound of Formula (I), the compound of Formula (IIa), Formula (IIb), or a mixture thereof, photoinitiator, and solvent have a ratio of about 86.5:1:11.5:1 by weight (w/w %).

The terms and expressions employed herein are used as terms of description and not of limitation, and there is no intention in the use of such terms and expressions of excluding any equivalents of the features shown and described or portions thereof, but it is recognized that various modifications are possible within the scope of the embodiments of the present application. Thus, it should be understood that although the present application describes specific embodiments and optional features, modification and variation of the compositions, methods, and concepts herein disclosed may be resorted to by those of ordinary skill in the art, and that such modifications and variations are considered to be within the scope of embodiments of the present application.

What is claimed is:

1. A composition comprising a compound of Formula (I), or a solvate, stereoisomer, or salt thereof:

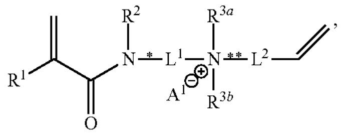

(I)

wherein:

$R^1$ is selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^2$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^{3a}$ and $R^{3b}$ are each independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^1$ is selected from the group consisting of optionally substituted $C_1$-$C_{10}$ alkylenyl and optionally substituted $C_2$-$C_{10}$ alkenylenyl;

$L^2$ is selected from the group consisting of optionally substituted $C_2$-$C_{100}$ alkylenyl and optionally substituted $C_2$-$C_{100}$ alkenylenyl;

$A^1$ is a counter anion, wherein at least one of the following applies:

(a) $R^1$ is $CH_3$;

(b) $R^2$ is H;

(c) $R^{3a}$ and $R^{3b}$ are each independently $CH_3$;

(d) $L^1$ is $*—CH_2CH_2CH_2—$;

(e) $L^2$ is $**—(CH_2)_{14}CH═CH—$; and (f) $A^1$ is bromide.

2. The composition of claim 1, wherein the compound of Formula (I) is:

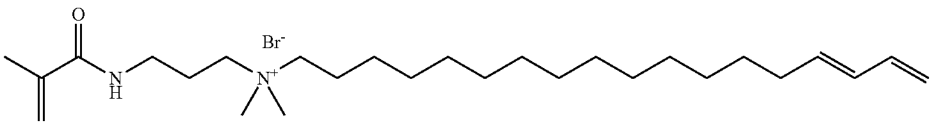
.

3. The composition of claim 1, wherein the compound of Formula (I) comprises about 80% to about 90% of the composition by weight (w/w %).

4. The composition of claim 1, wherein the composition further comprises a solvent, optionally wherein the solvent is water.

5. The composition of claim 4, wherein the solvent comprises about 5% to about 15% of the composition by weight (w/w %).

6. The composition of claim 4, wherein the solvent is water and the compound of Formula (I) and the water have a ratio selected from the group consisting of about 87.5:11.5, 88:11, and 84:11 by weight.

7. The composition of claim 1, wherein the composition further comprises at least one compound selected from the group consisting of:

(a) a compound of Formula (IIa), or solvate, stereoisomer, or salt thereof:

(IIa)

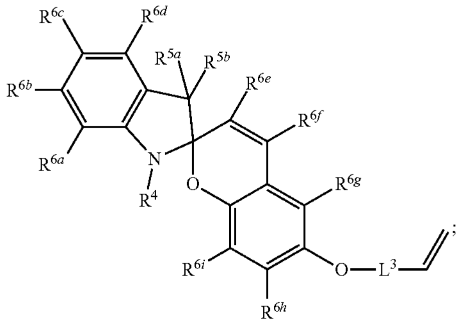
;

and (b) a compound of Formula (IIb), or solvate, stereoisomer, or salt thereof:

(IIb)

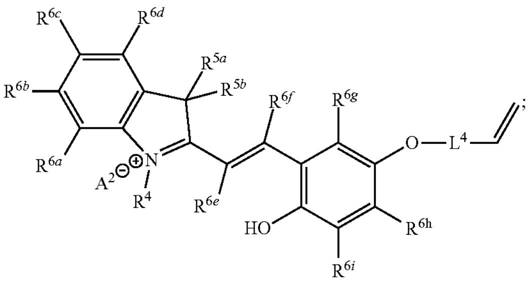
;

wherein:

each occurrence of $R^4$ is selected from the group consisting of H, optionally substituted $C_1$-$C_6$ alkyl, optionally substituted $C_3$-$C_8$ cycloalkyl, optionally substituted $C_2$-$C_8$ heterocycloalkyl, optionally substituted $C_6$-$C_{10}$ aryl, and optionally substituted $C_5$-$C_{10}$ heteroaryl;

each occurrence of $R^{5a}$ and $R^{5b}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

each occurrence of $R^{6a}$, $R^{6b}$, $R^{6c}$, $R^{6d}$, $R^{6e}$, $R^{6f}$, $R^{6g}$, $R^{6h}$, and $R^{6i}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^3$ and $L^4$ are each independently selected from the group consisting of optionally substituted $C_1$-$C_{100}$ alkylenyl and optionally substituted $C_2$-$C_{100}$ alkenylenyl; and $A^2$ is a counter anion.

8. The composition of claim 7, wherein at least one of the following applies:

(a) $R^4$ is $CH_3$;

(b) $R^{5a}$ and $R^{5b}$ are each independently $CH_3$;

(c) $R^{6a}$, $R^{6b}$, $R^{6c}$, $R^{6d}$, $R^{6e}$, $R^{6f}$, $R^{6g}$, $R^{6h}$, and $R^{6i}$ are each independently H;

(d) $L^3$ is $-(CH_2)_{14}CH{=}CH$-';

(e) $L^4$ is $-(CH_2)_{14}CH{=}CH$-"; and (f) $A^2$ is bromide.

9. The composition of claim 7, wherein at least one of the following applies:

(a) the compound of Formula (IIa) is:

(IIa)

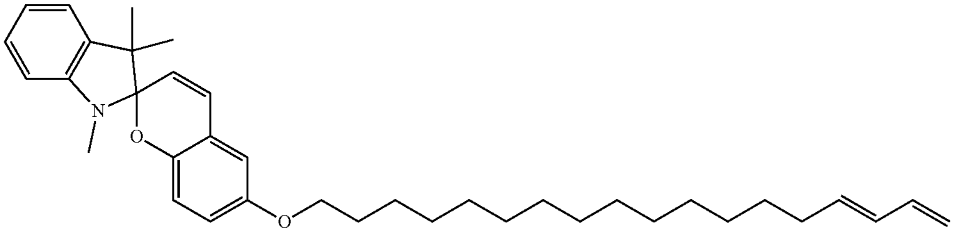

;

and (b) the compound of Formula (IIb) is:

(IIb)

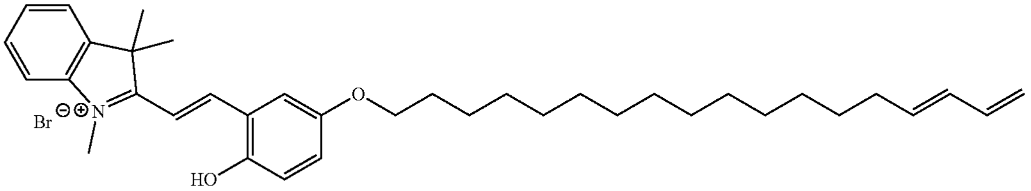

.

10. The composition of claim 7, wherein at least one of the following applies:

(a) the compound of Formula (IIa) and Formula (IIb) each independently comprise about 0.1% to about 5% of the composition by weight (w/w %);

(b) the compound of Formula (I) and the compound of Formula (IIa), Formula (IIb), or mixture thereof have a ratio of about 86.5:1 by weight (w/w %).

11. A polymer composition comprising a polymerized product of the composition of claim 1.

12. The polymer composition of claim 11, wherein the polymer comprises a plurality of nanoholes.

13. The composition of claim 11, wherein the polymer comprises an aqueous lyotropic liquid crystal (LLC) phase comprising a gyroid bicontinuous cubic (Q-phase) morphology.

14. A polymer composition comprising the polymerized product of the composition of claim 7, wherein the polymer composition comprises the reaction product of two or more compounds selected from the group consisting of the compound of Formula (I), the compound of Formula (IIa), and the compound of Formula (IIb), wherein each of the following apply:

(a) a covalent bond is formed between at least one alkene of a first compound of Formula (I) and at least one alkene of a second compound of Formula (I);

(b) a covalent bond is formed between at least one alkene of the compound of Formula (I) and at least one alkene of the compound of Formula (IIa) or the compound of Formula (IIb).

15. The polymer composition of claim 14, wherein the polymer composition is responsive to external stimuli, wherein at least one of the following applies:

(a) the external stimuli is at least one selected from the group consisting of pH changes, UV irradiation, and/or $Pb^{2+}$ ions; and (b) the response is selected from the group consisting of changes in color and changes in unit cell dimensions.

16. A method of preparing a polymer composition, the method comprising:

(a) contacting the compound of Formula (I), or a solvate, stereoisomer, or salt thereof, and a photoinitiator in the presence of a solvent to provide a gyroid mesophase gel; and (b) irradiating the gyroid mesophase gel with UV light, wherein the compound of Formula (I) has the structure:

(I)

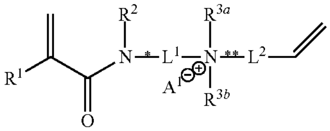

, wherein:

$R^1$ is selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^2$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^{3a}$ and $R^{3b}$ are each independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^1$ is selected from the group consisting of optionally substituted $C_1$-$C_{10}$ alkylenyl and optionally substituted $C_2$-$C_{10}$ alkenylenyl;

$L^2$ is selected from the group consisting of optionally substituted $C_2$-$C_{100}$ alkylenyl and optionally substituted $C_2$-$C_{100}$ alkenylenyl;

$A^1$ is a counter anion, wherein at least one of the following applies:

(a) $R^1$ is $CH_3$;

(b) $R^2$ is H;

(c) $R^{3a}$ and $R^{3b}$ are each independently $CH_3$;

(d) $L^1$ is *—$CH_2CH_2CH_2$—;

(e) $L^2$ is **—$(CH_2)_{14}CH{=}CH$—; and (f) $A^1$ is bromide.

17. The method of claim 16, wherein at least one of the following applies:

(a) the photoinitiator is selected from the group consisting of 2,2-dimethoxy-2-phenylacetophenone (DMPA) and 2-hydroxy-4'-(2-hydroxyethoxy)-2-methylpropiophenone (HHMP);

(b) the solvent is water; and (c) the compound of Formula (I), photoinitiator, and solvent have a ratio of about 87.5:11.5:1, 88:11:1, and 84:11:1 by weight (w/w %).

18. A method of preparing a polymer composition, the method comprising:

(a) contacting a compound of Formula (I), or a solvate, stereoisomer, or salt thereof, with at least one compound independently selected from the group consisting of a compound of Formula (IIa) and a compound of Formula (IIb)), or a solvate, stereoisomer, or salt thereof; and a photoinitiator in the presence of a solvent to provide a gyroid mesophase gel; and (b) irradiating the gyroid mesophase gel with UV light, wherein each of the following apply:

(a) a covalent bond is formed between at least one alkene of a first compound of Formula (I) and at least one alkene of a second compound of Formula (I);

(b) a covalent bond is formed between at least one alkene of the compound of Formula (I) and at least one alkene of the compound of Formula (IIa) or the compound of Formula (IIb), wherein the compound of Formula (I) has the structure:

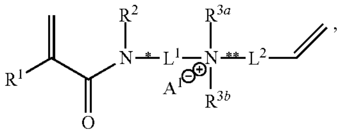

(I)

wherein:

$R^1$ is selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^2$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$R^{3a}$ and $R^{3b}$ are each independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^1$ is selected from the group consisting of optionally substituted $C_1$-$C_{10}$ alkylenyl and optionally substituted $C_2$-$C_{10}$ alkenylenyl;

$L^2$ is selected from the group consisting of optionally substituted $C_1$-$C_{100}$ alkylenyl and optionally substituted $C_2$-$C_{100}$ alkenylenyl;

$A^1$ is a counter anion, wherein at least one of the following applies to the compound of Formula (I):

(a) $R^1$ is $CH_3$;

(b) $R^2$ is H;

(c) $R^{3a}$ and $R^{3b}$ are each independently $CH_3$;

(d) $L^1$ is *—$CH_2CH_2CH_2$—;

(e) $L^2$ is **—$(CH_2)_{14}CH{=}CH$—; and (f) $A^1$ is bromide;

wherein the compound of Formula (IIa) has the structure:

(IIa)

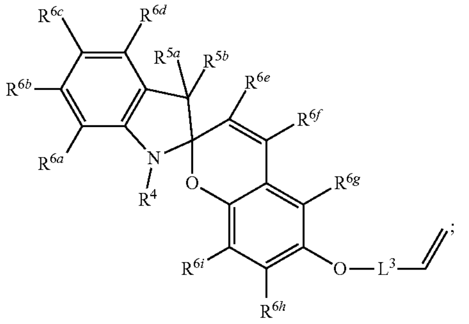

wherein the compound of Formula (IIb) has the structure:

(IIb)

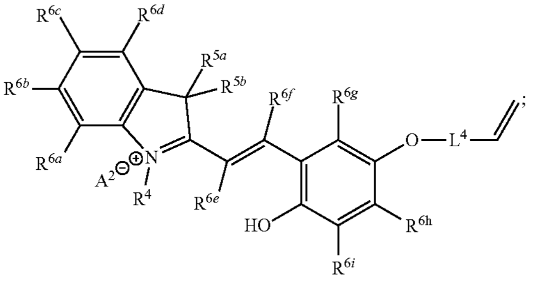

wherein:

each occurrence of $R^4$ is selected from the group consisting of H, optionally substituted $C_1$-$C_6$ alkyl, optionally substituted $C_3$-$C_8$ cycloalkyl, optionally substituted $C_2$-$C_8$ heterocycloalkyl, optionally substituted $C_6$-$C_{10}$ aryl, and optionally substituted $C_5$-$C_{10}$ heteroaryl;

each occurrence of $R^{5a}$ and $R^{5b}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

each occurrence of $R^{6a}$, $R^{6b}$, $R^{6c}$, $R^{6d}$, $R^{6e}$, $R^{6f}$, $R^{6g}$, $R^{6h}$, and $R^{6i}$ is independently selected from the group consisting of hydrogen, halogen, CN, $NO_2$, optionally substituted $C_1$-$C_6$ alkyl, optionally substituted $C_1$-$C_6$ alkoxy, optionally substituted $C_6$-$C_{10}$ aryl, and optionally substituted $C_5$-$C_{10}$ heteroaryl;

$L^3$ and $L^4$ are each independently selected from the group consisting of optionally substituted $C_1$-$C_{100}$ alkylenyl and optionally substituted $C_2$-$C_{100}$ alkenylenyl; and $A^2$ is a counter anion.

19. The method of claim 18, wherein at least one of the following applies:

(a) the photoinitiator is selected from the group consisting of 2,2-dimethoxy-2-phenylacetophenone (DMPA) and 2-hydroxy-4'-(2-hydroxyethoxy)-2-methylpropiophenone (HHMP);

(b) the solvent is water; and (c) the compound of Formula (I), the compound of Formula (IIa), the compound of Formula (IIb), or a mixture thereof, photoinitiator, and solvent have a ratio of about 86.5:1:11.5:1 by weight (w/w %).

* * * * *